(12) United States Patent
Goldberg et al.

(10) Patent No.: US 12,295,879 B1
(45) Date of Patent: May 13, 2025

(54) TONGUE EMBRACING ORAL RETENTION DEVICE AND METHOD OF MANUFACTURE

(71) Applicants: Howell Goldberg, Parkland, FL (US); Daniel A. Zabaleta, Cooper City, FL (US)

(72) Inventors: Howell Goldberg, Parkland, FL (US); Daniel A. Zabaleta, Cooper City, FL (US)

(*) Notice: Subject to any disclaimer, the term of this patent is extended or adjusted under 35 U.S.C. 154(b) by 681 days.

(21) Appl. No.: 17/503,684

(22) Filed: Oct. 18, 2021

Related U.S. Application Data

(63) Continuation-in-part of application No. 15/997,637, filed on Jun. 4, 2018, now Pat. No. 11,147,706, which
(Continued)

(51) Int. Cl.
*A61F 5/56* (2006.01)
*A61C 9/00* (2006.01)
(Continued)

(52) U.S. Cl.
CPC ............ *A61F 5/566* (2013.01); *A61C 9/0006* (2013.01); *A61C 9/0053* (2013.01);
(Continued)

(58) Field of Classification Search
CPC ... A61F 5/56; A61F 5/566; A61C 7/08; A61C 5/90; A61M 16/0488; A61M 16/049; A61M 16/0493; A61M 16/0605
See application file for complete search history.

(56) References Cited

U.S. PATENT DOCUMENTS

| 4,169,473 A | 10/1979 | Samelson |
|---|---|---|
| 5,318,043 A | 6/1994 | Burr et al. |

(Continued)

FOREIGN PATENT DOCUMENTS

| CA | 2373407 A1 | 8/2002 |
|---|---|---|
| CA | 3073969 A1 | 3/2019 |

OTHER PUBLICATIONS

Link: https://www.rochesteradvanceddentistry.com/tongue-stabilizing-device/; Date unknown.
(Continued)

*Primary Examiner* — Keri J Nelson
(74) *Attorney, Agent, or Firm* — Allen D. Hertz, P.A.; Allen D. Hertz

(57) ABSTRACT

A tongue attachment assembly includes a sheath designed for attachment to a patient's tongue using a vacuum. An accessory attachment feature comprising a groove located between a flange and the distal end of the body of the sheath. Vacuum can be drawn through a valve or an external vacuum source. The tongue attachment assembly can be adapted for any of a variety of applications by selecting an appropriate accessory and attaching the accessory to the sheath by the accessory attachment feature. Accessories can include a sleep apnea attachment, a gas delivery mask retention attachment, and the like. The tongue attachment assembly can be fabricated by replicating a shape of a patient's tongue as a portion of a mold, then using the mold to generate the tongue attachment assembly. The tongue mold can be obtained by a scanning process or an impression or casting process.

21 Claims, 43 Drawing Sheets

Related U.S. Application Data is a continuation-in-part of application No. 14/703,858, filed on May 4, 2015, now Pat. No. 10,206,809, which is a continuation-in-part of application No. 13/609,754, filed on Sep. 11, 2012, now abandoned, which is a continuation-in-part of application No. 12/883,156, filed on Sep. 15, 2010, now Pat. No. 8,261,748.

(60) Provisional application No. 62/514,837, filed on Jun. 3, 2017.

(51) Int. Cl.
  *A61M 16/00* (2006.01)
  *A61M 16/20* (2006.01)
(52) U.S. Cl.
  CPC ........ *A61M 16/0003* (2014.02); *A61M 16/20* (2013.01); *A61M 2210/0643* (2013.01)

(56) References Cited

U.S. PATENT DOCUMENTS

| | | |
|---|---|---|
| 5,373,859 A | 12/1994 | Forney |
| 5,465,734 A | 11/1995 | Alvarez |
| 5,566,683 A | 10/1996 | Thornton |
| 5,649,540 A | 7/1997 | Alvarez et al. |
| 5,921,241 A | 7/1999 | Belfer |
| 6,422,243 B1 | 7/2002 | Daram |
| D461,240 S | 8/2002 | Dort |
| 6,634,359 B1 * | 10/2003 | Rudy, Jr. ............ A61M 16/0493 128/207.14 |
| 6,877,513 B2 | 4/2005 | Scarberry et al. |
| 7,607,439 B2 | 10/2009 | Li |
| 7,946,292 B2 | 5/2011 | Dort |
| 8,037,886 B2 | 10/2011 | Sotos et al. |
| 8,931,486 B2 | 1/2015 | Halstrom |
| 9,492,310 B2 | 11/2016 | Makower et al. |
| 9,956,111 B2 | 5/2018 | Togliatti |
| 11,096,821 B2 | 8/2021 | Hofmeyr |
| 2003/0234022 A1 | 12/2003 | Belfer |
| 2009/0078276 A1 | 3/2009 | Dort |
| 2009/0217931 A1 | 9/2009 | Davies |
| 2010/0154802 A1 | 6/2010 | Fuselier |
| 2015/0114403 A1 | 4/2015 | Togliatti |
| 2018/0243124 A1 | 8/2018 | Togliatti |
| 2018/0360692 A1 | 12/2018 | Sieffert |
| 2021/0045910 A1 | 2/2021 | Hofmeyr |

OTHER PUBLICATIONS

Link: https://na.aveotsd.com/; 1999.

* cited by examiner

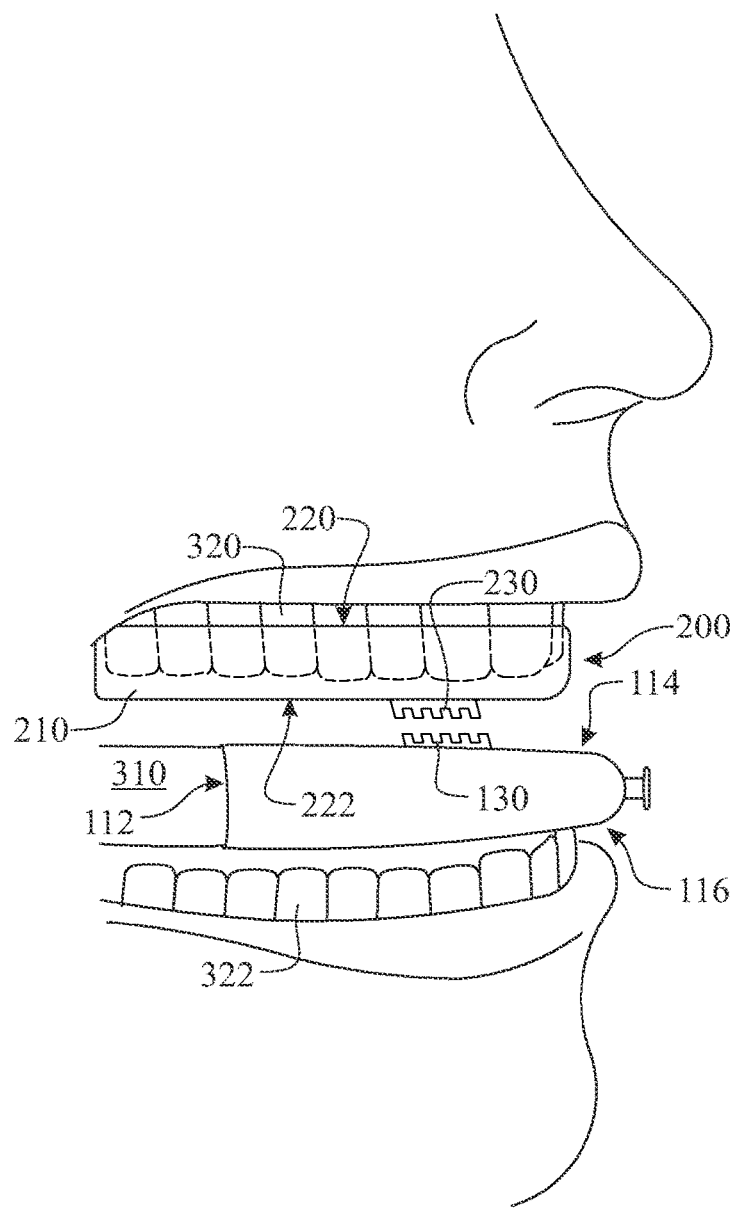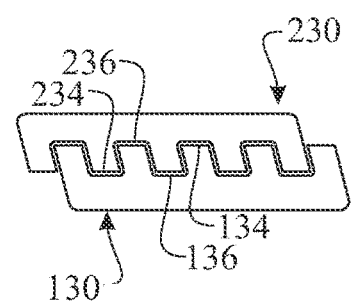
FIG. 11
FIG. 12

TONGUE EMBRACING ORAL RETENTION DEVICE AND METHOD OF MANUFACTURE

RELATED APPLICATIONS

This Non-Provisional Utility Patent Application is:
(A) a Continuation-In-Part (CIP) of U.S. Non-Provisional Utility patent application Ser. No. 15/997,637, filed on Jun. 4, 2018 (Scheduled to issue as U.S. Pat. No. 11,147,706 on Oct. 19, 2021),
wherein Ser. No. 15/997,637 is a Continuation-In-Part (CIP) of U.S. Non-Provisional Utility patent application Ser. No. 14/703,858, filed on May 4, 2015 (Now Issued as U.S. Pat. No. 10,206,809 on Feb. 19, 2019),
wherein U.S. Non-Provisional Utility patent application Ser. No. 14/703,858 is a Continuation-In-Part (CIP) claiming the benefit of U.S. Non-Provisional Utility patent application Ser. No. 13/609,754, filed on Sep. 11, 2012,
wherein U.S. Non-Provisional Utility patent application Ser. No. 13/609,754 is a Continuation-In-Part (CIP) claiming the benefit of U.S. Non-Provisional patent application Ser. No. 12/883,156, filed on Sep. 15, 2010 (Now Issued as U.S. Pat. No. 8,261,748 on Sep. 11, 2012),
(B) wherein U.S. Non-Provisional Utility patent application Ser. No. 15/997,637 is a Non-Provisional Utility patent application claiming the benefit of U.S. Provisional Patent Application Ser. No. 62/514,837, filed on Jun. 3, 2017,
(C) all of which are incorporated herein in their entireties. Regarding co-pendency: Jun. 3, 2018 falls on a Sunday. Therefore, co-pendency is extended through Monday, Jun. 4, 2018.

FIELD OF THE INVENTION

The present disclosure relates to an oral medical apparatus used for multiple purposes. More particularly, the oral medical apparatus comprises an attachment feature carried by a tongue engaging sheath. Any of a variety of accessories is supported by the attachment feature, wherein each accessory provides a function such as prevention of snoring and sleep apnea, retention of an upper or lower lip, positioning of a tongue, and the like.

BACKGROUND OF THE INVENTION

The present invention provides an oral medical apparatus used in the prevention of snoring and sleep apnea. Snoring is the vibration of respiratory structures and the resulting sound due to obstructed air movement when a human breathes during sleep. Generally, the uvula and soft palate are the anatomical structures that cause the sound of snoring if a human's tongue drops to the back of their mouth during sleep.

Sleep apnea is a sleep disorder characterized by having one or more pauses in breathing, or shallow breaths during sleep, and is typically accompanied by snoring. Each pause or cessation is generally referred to as an apnea, and can last from a few seconds to minutes. Additionally, each apnea may occur from five to thirty or more times per hour of sleep. Although most humans do experience some level of sleep apnea during their lifetime, a relatively smaller percentage (approximately 20%) of humans, suffer with chronic, severe sleep apnea. A combination of factors causes sleep apnea or snoring. One factor is the relaxation of muscle tone that results from sleep. Another factor is the vibration of soft, collapsible tissue surrounding the human airway, which causes snoring.

There are several snoring control devices known in the art. These devices provide for reception of the tongue in a hollow tongue-retained holder. One problem presented by these devices, however, is the inadequate fit between the tongue-retained holder and the user's tongue. In particular, the device determines the position of the tongue. Consequently, a relatively long tongue is not properly or comfortably accommodated within the socket. Different sized devices or custom fabricated devices can be provided to help overcome this shortcoming, wherein the variety and custom fit devices are provided at a higher cost.

Another known device provides a tongue sleeve configured for reception and retention of the outer extent of the user's tongue, and includes a shield shaped to be received and retained outside of the user's lip, as well as a component that allows the user to attach and adjust the shield to the tongue sleeve. This component permits for selective adjustment of the shield's position relative to the tongue, reducing snoring and airway obstruction.

Another device, known as the aveoTSD, provides suction between the device and the user's tongue. This suction prevents the tongue from moving toward the back of the mouth, thereby, keeping the airway open during sleep to prevent snoring. This device is known to slip and some wearer's have felt that it is uncomfortable.

During a dental or other oral medical procedure, it is desirous to retain the patient's lip and/or tongue in a desired position.

Oral devices are commonly designed to be dedicated to a single function. More specifically, tongue sleeves are used in conjunction with a respective teeth attachment component for sleeve apnea. The tongue sleeve and the respective teeth attachment component are specifically designed to function with one another for a single use. What is desired is a system that is adaptable to a variety of applications.

Unfortunately, with all of the attempted improvements that have been made in sleep apnea prevention devices, there remains a need for a device that is more comfortable to wear and provides more effective results.

Additionally, there are benefits to creating a series of accessories for a variety of applications based upon the use of a tongue embracing member.

BRIEF SUMMARY OF THE INVENTION

The present disclosure is generally directed to a sleep apnea control device, the device comprising:
a tongue attachment subassembly comprising:
a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, and
a sheath interlock member extending outward from the dorsal side of the sheath; and
a maxilla attachment subassembly comprising:
a maxilla tray shaped to conform to and removably engage with an individual's upper dental arch, the maxilla tray defined having an engagement side and an interlock side, and
a tray interlock member extending from the interlock side of the maxilla tray and positioned to interlock with the sheath interlock member, which, when interlocked, extends an individual's tongue during use.

In one aspect, the sheath interlock member is fabricated of a rigid material and the tongue attachment subassembly is fabricated of a pliant material.

In another aspect, the device further includes an air extraction system. An embodiment of the air extraction assembly is provided, which comprises an air extraction valve integrated into the tongue attachment subassembly, wherein the valve is in fluid communication with the tongue receiving cavity. The air extraction device may include an air extraction pipette in fluid communication with an air extraction bulb, where the air extraction pipette is in fluid communication with the air extraction valve to remove air from within the tongue receiving cavity. The air extraction device can be retained or integrated with the air extraction valve or removable therefrom.

In yet another aspect, the air extraction valve may be a separate component and assembled to the sheath.

In yet another aspect, the air extraction valve may be integrally fabricated with the sheath.

In yet another aspect, the sheath interlock member further comprises a sheath interlock ridge, and the tray interlock member further comprises a tray interlock ridge, the ridge having an interlock interface to removably engage the sheath interlock ridge and the tray interlock ridge.

In yet another aspect, the interlock interface is fabricated having a series of teeth and teeth-receiving receptacles.

In yet another aspect, the interlock teeth are disposed at an acute angle.

In yet another aspect, the tongue attachment subassembly further includes a tongue base clearance defined by a U-shaped recession in the ventral side, which extends inward from an opening of the tongue receiving cavity opening.

In yet another aspect, the tongue attachment subassembly is fabricated having a bladder formed within the main body walls, wherein the air extraction valve is provided in fluid communication with the bladder. The user extracts air from the bladder, securing the tongue attachment subassembly to the individual's tongue.

In yet another aspect, the sheath interlock member further comprises a sheath interlock array, and the tray interlock member further comprises a tray interlock array, wherein the sheath interlock array and the tray interlock array removably engage with one another in a manner enabling both lateral and longitudinal adjustments. In a preferred embodiment, the arrays comprise a series of interlocking pins and pin receiving cavities.

In a second embodiment, the present disclosure further comprises an accessory to be adapted to the tongue attachment subassembly to create a lip positioning appliance, the appliance comprising:
 a tongue attachment subassembly comprising:
  a sheath shaped to conform to a surface of an individual's tongue, the sheath having a tongue receiving cavity defining an opening for receiving the individual's tongue provided at a proximal end thereof, the sheath having an orientation defined by a dorsal side and a ventral side, and
  a sheath interlock member extending outward from the dorsal side of the sheath; and
 a maxilla lip retention subassembly comprising:
  a lip retention section having an arched shape to follow a contour of a patient's lip,
  a maxilla lip retention positioning arm extending from the lip retention section,
  a tray interlock member located at an attachment end of the maxilla lip retention positioning arm and located to interlock with the sheath interlock member, wherein when interlocked and installed, retains the lip retention section in engagement with an individual's lip, and
 a tray interlock member extending from the interlock side of the maxilla tray and positioned to interlock with the sheath interlock member, which, when interlocked, extends an individual's tongue during use.

In one aspect, the sheath interlock member can be adapted to a maxilla lip retention subassembly to retain a patient's maxilla lip and tongue in a desired position during a procedure.

In another aspect, the sheath interlock member and maxilla lip retention subassembly further comprising a longitudinally adjusting interface between the two members.

In yet another aspect, the sheath interlock member and maxilla lip retention subassembly further comprising a longitudinally adjusting interface between the two members. The longitudinal adjustment can be used to control the position of the patient's tongue during a procedure.

In yet another aspect, the sheath interlock member and maxilla lip retention subassembly the longitudinally adjusting interface between the two members is provided by a series of interconnecting elements. The feature can introduce lateral adjustments with a laterally arranged series of interconnecting elements.

In yet another aspect, the sheath interlock member and maxilla lip retention subassembly the longitudinally adjusting interface between the two members is provided by a series of pins and mating series of receptacles.

In yet another aspect, the sheath interlock member and maxilla lip retention subassembly the longitudinally adjusting interface between the two members is provided by a slideably engaging interface.

In yet another aspect, the sheath interlock member and maxilla lip retention subassembly the longitudinally adjusting interface between the two members is provided by slideably engaging interface comprising a rail slideably engaging with a mating channel. The engagement can include a locking mechanism to retain the rail in a longitudinal relation with the mating channel.

In yet another aspect, the sheath interlock member and maxilla lip retention subassembly the longitudinally adjusting interface between the two members is provided by slideably engaging interface comprising a first arm in slideable communication with a second arm. The two arms can be retained to one another using any inter-arm retaining feature. The inter-arm retaining feature can be integrated into either arm or provided as a separate component.

In yet another aspect, at least one of the sheath interlock member arm and maxilla lip retention subassembly arm can include a position locking feature, wherein the position locking feature can be a series of ridges, teeth, scalloping, and the like. The position locking feature would engage with a position retaining member to retain the axial position relation between the sheath interlock member arm and maxilla lip retention subassembly arm.

In yet another aspect, the sheath interlock member arm and maxilla lip retention subassembly arm can are provided in a parallel relationship with a primary plane of the tongue attachment subassembly bladder.

In yet another aspect, a sheath interlock member arm of the sheath interlock member is fabricated of a substantially rigid material, whereas the tongue embracing member is fabricated of a material having substantially elastic properties.

In yet another aspect, the sheath interlock member is assembled to the tongue embracing member by an overmolding process.

In yet another aspect, the sheath interlock member is assembled to the tongue embracing member by slideably inserting a sheath interlock member base of the sheath interlock member into a receiving channel formed in the exterior surface of the dorsal side of the tongue embracing member.

In yet another aspect, the receiving channel formed in the exterior surface of the dorsal side of the tongue embracing member includes a first channel segment and a second channel segment located opposite the first channel segment.

In yet another aspect, the receiving channel formed in the exterior surface of the dorsal side of the tongue embracing member includes a first channel segment and a second channel segment located opposite the first channel segment, wherein the first channel segment and the second channel segment are generally perpendicular to a longitudinal axis of the tongue embracing member.

In yet another aspect, the receiving channel formed in the exterior surface of the dorsal side of the tongue embracing member includes a first channel segment and a second channel segment located opposite the first channel segment, wherein the first channel segment and the second channel segment are parallel to one another.

In yet another aspect, the receiving channel formed in the exterior surface of the dorsal side of the tongue embracing member further comprises a third channel segment, wherein the third channel segment spans between like ends of the first channel segment and the second channel segment, wherein the first channel segment, the third channel segment and the second channel segment collectively form a "U" shaped channel.

In yet another aspect, the receiving channel is spaced from the exterior surface of the dorsal side of the tongue embracing member by a channel riser feature, wherein the channel riser feature reduces transfer of torsional and/or sheer forces from the sheath interlock member to the tongue embracing member. The reduction in transfer of forces reduces a potential scenario which can separate an interior surface of the tongue embracing member from the user's tongue, which can result in separation and dislodgement of the tongue embracing member from the user's tongue, resulting in an ineffective device.

In yet another aspect, the sheath interlock member arm and the maxilla lip retention subassembly arm are assembled positioning mating surfaces contacting or against one another.

In yet another aspect, at least one of the sheath interlock member arm and the maxilla lip retention subassembly arm is formed having a changing thickness defining a tapering distal or outer surface.

In yet another aspect, the changing thickness of the at least one of the sheath interlock member arm and the maxilla lip retention subassembly arm is linear along at least a portion of a length of the respective at least one arm.

In yet another aspect, the changing thickness of the at least one of the sheath interlock member arm and the maxilla lip retention subassembly arm forms a curved or arched surface along at least a portion of a length of the respective at least one arm.

In yet another aspect, a position retaining member at least partially circumscribes an external periphery defined by an assembly of the sheath interlock member arm and the maxilla lip retention subassembly arm. The position retaining member can be formed having a tubular rectangle shape, a tubular oblong shape, an elliptical shape, and the like, wherein the preferred shape would mimic the cross sectional shape of the assembly of the sheath interlock member arm and the maxilla lip retention subassembly arm. An interior distance spanning between an interior transverse or upper surface and an interior opposite transverse or lower surface of the position retaining member is sized enabling a sliding motion between the sheath interlock member arm and the maxilla lip retention subassembly arm when positioned at a location of the assembly having a narrow thickness and restraining any sliding motion between the sheath interlock member arm and the maxilla lip retention subassembly arm when positioned at a location of the assembly having a wider thickness.

In yet another aspect, the mating surfaces of the sheath interlock member arm and the maxilla lip retention subassembly arm are smooth.

In yet another aspect, the mating surfaces of the sheath interlock member arm and the maxilla lip retention subassembly arm are textured to increase a frictional force generated therebetween.

In yet another aspect, the mating surfaces of the sheath interlock member arm and the maxilla lip retention subassembly arm are co-planar.

In yet another aspect, the mating surfaces of the sheath interlock member arm and the maxilla lip retention subassembly arm include a series of mating mechanically engaging features.

In yet another aspect, the mating surfaces of the sheath interlock member arm and the maxilla lip retention subassembly arm include a series of mating mechanically engaging features, wherein (a) in a condition where the series of mating mechanically engaging features are engaged with one another, the sheath interlock member arm and the maxilla lip retention subassembly arm are restrained from a sliding motion therebetween and (b) in a condition where the series of mating mechanically engaging features are disengaged or separated from one another, the sheath interlock member arm and the maxilla lip retention subassembly arm are capable of a sliding or linear repositioning motion between one another.

In yet another aspect, a position retaining member can be positioned against external surfaces of the sheath interlock member arm and the maxilla lip retention subassembly arm at a position having a thickness that is approximately equal to an distance between opposite, internal transverse surfaces of the position retaining member to retain engagement between mating mechanically engaging features, thus retaining an axial relationship between the sheath interlock member arm and the maxilla lip retention subassembly arm.

In yet another aspect, the mating surfaces of the sheath interlock member arm and the maxilla lip retention subassembly arm include a series of mating mechanically engaging features comprising a series of peaks and valleys.

In yet another aspect, the mating surfaces of the sheath interlock member arm and the maxilla lip retention subassembly arm include a series of mating mechanically engaging features comprising a series of peaks and valleys, wherein the peaks and valleys are linear and spatially arranged.

In yet another aspect, the mating surfaces of the sheath interlock member arm and the maxilla lip retention subassembly arm include a series of mating mechanically engaging features comprising a series of peaks and valleys, wherein are linear, oriented substantially parallel to one another, and spatially arranged.

In yet another aspect, the mating surfaces of the sheath interlock member arm and the maxilla lip retention subassembly arm include a series of mating mechanically engaging features comprising a series of peaks and valleys, wherein the peaks and valleys are linear, oriented substantially perpendicular to a longitudinal axis of each arm, and spatially arranged.

In yet another aspect, the mating surfaces of the sheath interlock member arm and the maxilla lip retention subassembly arm include a series of mating mechanically engaging features comprising a series of peaks and valleys, wherein the peaks and valleys are linear and equally spaced arranged.

In yet another aspect, at least one of the sheath interlock member arm and the maxilla lip retention subassembly arm further comprises a position retaining member retention feature.

In yet another aspect, at least one of the sheath interlock member arm and the maxilla lip retention subassembly arm further comprises a position retaining member retention feature, wherein the position retaining member retention feature is a boss or other outwardly extending feature located proximate a distal end of the associated arm.

In yet another aspect, the maxilla lip retention subassembly comprises a lip retention feature. The lip retention feature can formed in any suitable shape for comfortably retaining the patient's maxilla lip.

In yet another aspect, the lip retention feature is fabricated inclusive of a pliant material. The pliant material may be silicone, nylon, rubber, plastic, wax, and the like.

In yet another aspect, the lip retention feature can be shaped to engage with a gum line of the patient.

In yet another aspect, the tongue embracing member comprises an air extraction valve.

In yet another aspect, the air extraction valve includes a valve seal that opens outward from a sealing feature.

In yet another aspect, the sealing feature is a flange circumscribing an interior circumference of an air extraction tube comprising the air extraction valve.

In yet another aspect, the air extraction valve includes a valve seal that pivotally opens outward from the sealing feature.

In yet another aspect, the valve seal is in operational communication with a valve operational handle.

In yet another aspect, the valve operational handle is operated by a mechanical interference with a feature and/or surface of a bulb air extraction tube of an air extraction device.

In yet another aspect, the valve operational handle includes at least one of a magnet and a magnetically attracting material and the bulb air extraction tube of an air extraction device comprises a mating at least one of a magnet and a magnetically attracting material, thus resulting in a magnetic attraction between the two elements. The magnetic attraction draws the valve seal into a closed or sealed configuration when the bulb air extraction tube of the air extraction device is slideably removed from the tongue embracing member air extraction tube.

In yet another aspect, at least one of the valve operational handle and the valve seal is in operational communication with a biasing element. The biasing element can be any form of a biasing element, including a coil spring, a cantilever spring, and the like.

In yet another aspect, the bulb air extraction tube further comprises a lead in feature, wherein one exemplary lead in feature is chamfered interior surface.

In yet another aspect, the bulb air extraction tube further comprises a valve insertion stop seat, wherein the valve insertion stop seat limits the sliding motion between the tongue embracing member air extraction tube and the interior surface of the bulb air extraction tube of the air extraction device.

In yet another aspect, the valve insertion stop seat is formed as an internal ridge at least partially circumscribing the interior surface of the bulb air extraction tube of the air extraction device.

In yet another aspect, the tongue embracing member air extraction tube includes an air extraction valve clearance, providing a clearance for the valve flap when the valve flap is rotated into an open configuration.

In yet another aspect, a vacuum formed within the tongue embracing member retains the valve flap in a closed configuration.

In yet another aspect, a sheath tongue sealing ridge is formed along at least a portion of a contacting circumferential surface of an interior surface of the tongue embracing member.

In yet another embodiment, the present disclosure further comprises a tongue attachment subassembly comprising:
- a sheath having a body shaped to conform to a surface of an individual's tongue, the sheath having an orientation defined by a proximal end and a distal end;
- a tongue receiving cavity extending inward from an opening in the proximal end of the sheath, the tongue receiving cavity having a size and a shape for receiving and engaging with the individual's tongue;
- a vacuum passageway passing through the distal end of the sheath into the tongue receiving cavity; and
- an accessory attachment feature comprising a groove located between a flange and the distal end of the body of the sheath.

In a second aspect, the tongue attachment subassembly further comprises a check valve integrally provided with the vacuum passageway.

In another aspect, the check valve is provided in a form of a duck bill valve. The duckbill valve comprising a flexible upper member and a flexible lower member mating at a slit. An applied vacuum draws the flexible upper member and the flexible lower member towards one another, sealing the slit.

In yet another aspect, the duck bill valve is integrally formed with the vacuum passageway.

In yet another aspect, the accessory attachment groove and the accessory attachment flange are annular in shape.

In yet another aspect, the accessory attachment groove and the accessory attachment flange are formed along a neck segment of the check valve.

In another aspect, the accessory attachment feature comprises groove and a flange, the groove being located between the flange and the distal end of the body of the sheath.

In yet another aspect, the tongue attachment subassembly further comprises a tongue protection insert located within the vacuum passageway.

In yet another aspect, the tongue protection insert comprises an insert interior flange located at an interior end of a tubular body. The tubular body is preferably sized and shaped for insertion into and sealing against an interior surface of the vacuum passageway of the sheath.

In yet another aspect, the tongue protection insert comprises at least one small vacuum passage orifice.

In yet another aspect, the tongue protection insert comprises a plurality of small, spatially arranged, vacuum passage orifices.

In yet another aspect, the insert interior flange is formed having a concave shaped tongue contacting surface.

In yet another aspect, the tubular body is cylindrically shaped.

In yet another aspect, the insert interior flange further comprises an orientation feature.

In yet another aspect, the insert interior flange further comprises an orientation feature, wherein the orientation feature is provided to properly align the concave shaped tongue contacting surface and the adjacent interior surface of the sheath.

In yet another aspect, the tongue protection insert comprises a central passageway extending from an inlet end thereof to the insert interior flange.

In yet another aspect, vacuum communication is provided through the tongue protection insert central passageway and small vacuum passage orifice(s).

In yet another aspect, the tongue protection insert comprises a central passageway extending from an inlet end thereof to an insert interior flange.

In yet another aspect, the tongue protection insert further comprises an exterior sealing flange, the exterior sealing flange being located proximate the inlet end of the tubular body.

In yet another aspect, the tongue attachment subassembly is designed for easy removal of the check valve.

In yet another aspect, the tongue attachment subassembly is designed for easy removal of the check valve by shearing the check valve from the vacuum passageway.

In yet another aspect, the tongue attachment subassembly is designed for easy removal of the check valve by shearing the check valve from the vacuum passageway along an outward surface of the accessory attachment flange.

In yet another embodiment, the present disclosure further comprises an assembly for treatment of sleep apnea, the assembly comprising:
  a tongue attachment subassembly including:
    a sheath having a body shaped to conform to a surface of an individual's tongue, the sheath having an orientation defined by a proximal end and a distal end;
    a tongue receiving cavity extending inward from an opening in the proximal end of the sheath, the tongue receiving cavity having a size and a shape for receiving and engaging with the individual's tongue;
    a vacuum passageway passing through the distal end of the sheath into the tongue receiving cavity; and
    an accessory attachment feature; and
  a tongue position retention subassembly comprising:
    a tongue position retention body,
    a face engaging surface formed on the tongue position retention body, and
    a tongue position retention bracket assembly clip adapted to support the tongue position retention body and engage with the accessory attachment feature,
    the tongue position retention subassembly being assembled to the tongue attachment subassembly by assembling the tongue position retention bracket assembly clip and the accessory attachment feature to one another.

In another aspect, the tongue position retention body is formed having an "S" shape.

In yet another aspect, the tongue position retention body is formed having a concave "S" shape.

In yet another aspect, the tongue position retention body is designed to engage with at least one of lips of a patient and a chin of the patient.

In yet another aspect, the tongue position retention body is designed to engage with cheeks of the patient.

In yet another aspect, the tongue position retention bracket assembly clip is formed having a "C" shape engaging surface, wherein the clip is sized and shaped to mate with the accessory attachment feature groove and seat against the accessory attachment feature flange.

In yet another aspect, the "C" shaped tongue position retention bracket assembly clip further comprises a clip retention feature formed on at least one end of the "C" shaped engaging surface of the clip.

In yet another aspect, the tongue position retention subassembly further comprises a valve guard.

In yet another aspect, the valve guard is formed having a generally "C" shape extending outward from an exterior surface of the tongue position retention body.

In another aspect, in use, the tongue attachment subassembly is secured to a tongue of a patient by slipping the sheath over the tongue and applying a vacuum to the sheath through the vacuum passageway, the face engaging surface of the position retention bracket assembly is placed against face of a patient, and the position retention bracket assembly is assembled to the tongue attachment subassembly by assembling the tongue position retention bracket assembly clip and the accessory attachment feature to one another.

In yet another aspect, a tongue compression component can be used in conjunction with the tongue attachment subassembly.

In yet another aspect, the tongue compression component includes an upper tongue compression arm, a lower tongue compression arm, and an assembly clip.

In yet another aspect, the tongue compression component includes an upper tongue compression arm, a lower tongue compression arm, and an assembly clip formed having a "C" shape engaging surface, wherein the clip is sized and shaped to mate with the accessory attachment feature groove and seat against the accessory attachment feature flange.

In yet another aspect, the upper tongue compression arm and the lower tongue compression arm are formed as cantilevered elements extending rearward from the tongue compression component assembly clip.

In yet another aspect, the upper tongue compression arm and the lower tongue compression arm are formed as cantilevered elements having a convex contacting surface and a concave exposed surface.

In yet another aspect, the upper tongue compression arm and the lower tongue compression arm are spaced to apply a compression force upon the tongue attachment subassembly. The spacing is such to apply a suitable compression force upon the dorsal side and ventral side of the tongue.

In yet another aspect, the compression force applied by the tongue compression component is provided to retain a patient's tongue in a natural shape. When worn, the tongue attachment subassembly could tend to draw the tongue into a rounded shape. The tongue compression component restores the tongue to the tongue's natural oval shape.

In yet another aspect, the tongue compression component is utilized in accordance with the following steps:
  installing a tongue compression component onto a tongue attachment subassembly, sliding the tongue attachment subassembly onto a patient's tongue, and extracting air from the tongue attachment subassembly.

In yet another aspect, the tongue compression component is utilized in accordance with the following additional steps:

adjusting the tongue compression component for comfort.

In yet another aspect, the tongue compression component is utilized in accordance with the following additional steps:

selecting a properly sized tongue compression component for use.

In yet another aspect, the tongue compression component is utilized in accordance with the following additional steps:

adjusting the tongue compression component to become the proper size for use.

In yet another aspect, the adjusting process can be accomplished by heating the tongue compression component (fabricated of a plastic, nylon, or the like) and adjusting an angle of each of the cantilevered arms.

In yet another aspect, the tongue compression component can further include at least one tooth locating projection; each at least one tooth locating projection extending outward from the exposed surface of at least one of the upper tongue compression arm and the lower tongue compression arm.

In yet another aspect, the tongue compression component can further include at least one pair of teeth locating projections; each teeth locating projection of the pair of teeth locating projections extending outward from the exposed surfaces of the respective upper tongue compression arm and the respective lower tongue compression arm. The pair of teeth locating projections is preferably in substantial axial registration with one another.

In yet another aspect, the tongue compression component can further include at least two pairs of teeth locating projections; each pair of teeth locating projection of the two pair of teeth locating projections extending outward from the exposed surfaces of the respective upper tongue compression arm and the respective lower tongue compression arm. The pair of teeth locating projections is preferably in substantial axial registration with one another. Adjacent teeth locating projections of each pair of teeth locating projections are spaced from one another to receive a patient's tooth or teeth.

In yet another aspect, a variety of tongue compression components, each tongue compression component can be offered having a different distance from the assembly clip for the teeth locating projections, wherein the position of the teeth locating projections locates the tongue position respective to the teeth.

In yet another aspect, the tongue compression component is designed where each tongue compression arm having a convex contacting surface, where an apex of the convex surface is positioned rearward of an end of the tongue.

In yet another aspect, the tongue compression component assembly clip has a thickness or a dimension spanning between a first flange engaging surface and a second flange engaging surface is substantially proximate a dimension spanning between a first flange surface and a second flange surface defining the interlock coupling groove.

In yet another aspect, the thickness of the tongue compression component assembly clip can be reduced to a dimension that is shorter than the span of the interlock coupling groove. The oral appliance assembly can further include a spacer having a thickness that is the difference between the thickness of the tongue compression component assembly clip and the span of the interlock coupling groove. The spacer and the tongue compression component assembly clip can have a like shape and size.

In yet another aspect, the arrangement can employ a plurality of spacers, where the sum of the thicknesses of the plurality of spacers equals the difference between the thickness of the tongue compression component assembly clip and the span of the interlock coupling groove. The positioning of the teeth engaging tongue compression component would be adjusted by varying a placement of the spacer or plurality of spacers.

In yet another aspect, the spacer can be inserted between the tongue compression component assembly clip and the forward or outer flange surface within the interlock coupling groove, positioning the teeth engaging tongue compression component rearward.

In yet another aspect, the spacer can be inserted between the tongue compression component assembly clip and the rearward or inner flange surface within the interlock coupling groove, positioning the teeth engaging tongue compression component forward.

In yet another aspect, a position of the accessory can be adjusted by inserting one or more spacers between at least one of:

(a) between the first flange engaging surface of the accessory clip body and the respective first flange surface of the tongue attachment assembly, and (b) between the second flange engaging surface of the accessory clip body and the respective second flange surface of the tongue attachment assembly.

In yet another aspect, a orbital tongue shaping device can be used for sleep apnea, where the orbital tongue shaping device is formed in a loop, including a generally linear dorsal segment having a slight arch between a forward edge and a rearward edge, a tightly arched left side segment, a generally linear ventral segment having a slight arch between the forward edge and the rearward edge, and a tightly arched left side segment, each segment being contiguous with an adjacent segment.

In yet another aspect, at least one of the segments of the orbital tongue shaping device can be shaped having a convex surface formed on a contacting surface and a concave surface formed on an exposed surface.

In yet another aspect, an opposite pair of the segments of the orbital tongue shaping device can be shaped having a convex surface formed on a contacting surface and a concave surface formed on an exposed surface.

In yet another aspect, all four segments of the orbital tongue shaping device can be shaped having a convex surface formed on a contacting surface and a concave surface formed on an exposed surface.

In yet another aspect, the dorsal segment and the ventral segment of the orbital tongue shaping device includes a leading edge wherein the leading edge is shaped having a central portion of a leading edge forward of each respective side region.

In yet another aspect, the leading edge has an arched shape, where a center of the arched shape extends forward of the body of the orbital tongue shaping device.

In yet another aspect, the trailing edge has an arched shape, where a center of the arched shape extends inward towards the body of the orbital tongue shaping device.

In yet another aspect, the dorsal segment and the ventral segment of the orbital tongue shaping device includes a trailing edge wherein the trailing edge is shaped having a central portion of the trailing edge forward of each respective side region.

In yet another aspect, the leading edge has an arched shape, where a center of the arched shape extends inward towards the body of the orbital tongue shaping device.

In yet another aspect, the trailing edge has an arched shape, where a center of the arched shape extends forward of the body of the orbital tongue shaping device.

In yet another aspect, the orbital tongue shaping device can be used independently or in conjunction with the tongue attachment subassembly.

In yet another aspect, the orbital tongue shaping device is of a size and shape to compress a patient's tongue in both a direction compressing a thickness of the tongue and a direction compressing a width of the tongue.

In yet another aspect, in use the orbital tongue shaping device compresses the patient's tongue in both a direction compressing a thickness of the tongue and a direction compressing a width of the tongue; the resulting reaction of the tongue is an expansion forward and an expansion in thickness of a segment of the tongue that is forward of the placement of the orbital tongue shaping device on the patient's tongue.

In yet another embodiment, the present disclosure further comprises an assembly for delivery of a gas, the assembly comprising:
  a tongue attachment subassembly including:
    a sheath having a body shaped to conform to a surface of an individual's tongue, the sheath having an orientation defined by a proximal end and a distal end;
    a tongue receiving cavity extending inward from an opening in the proximal end of the sheath, the tongue receiving cavity having a size and a shape for receiving and engaging with the individual's tongue;
    a vacuum passageway passing through the distal end of the sheath into the tongue receiving cavity; and
    an accessory attachment feature; and
  a mask retention subassembly comprising:
    a mask position retention body including a,
    a mask engaging surface formed on the mask position retention body, and
    a mask position retention bracket assembly clip adapted to support the mask position retention body and engage with the accessory attachment feature,
  the mask position retention subassembly being assembled to the tongue attachment subassembly by assembling the mask position retention bracket assembly clip and the accessory attachment feature to one another.

In another aspect, the tongue position retention body is formed having a pair of wings extending outward from a centrally located mask position retention bracket assembly clip.

In yet another aspect, each of the wings is formed having a convex curved exterior surface and a concave curved mask-contacting interior surface.

In yet another aspect, the tongue position retention body is designed to engage with a feature of a gas management mask.

In yet another aspect, the tongue position retention body is designed to engage an exterior surface of the gas management mask.

In yet another aspect, the mask position retention bracket assembly clip is formed having a "C" shape engaging surface, wherein the clip is sized and shaped to mate with the accessory attachment feature groove and seat against the accessory attachment feature flange.

In yet another aspect, the "C" shaped mask position retention bracket assembly clip further comprises a clip retention feature formed on at least one end of the "C" shaped engaging surface of the clip.

In yet another aspect, the mask position retention subassembly adequately supports the mask, exclusive of any additional securing elements (such as a strap and the like).

In yet another aspect, in use the orbital tongue shaping device compresses the patient's tongue in a first lateral direction, compressing a lateral thickness of the tongue; the resulting reaction of the tongue is an expansion forward and an expansion in vertical thickness of a segment of the tongue that is forward of the placement of the orbital tongue shaping device side regions on the patient's tongue, the orbital tongue shaping device dorsal segment and the ventral segment compressing the patient's tongue in a second vertical direction, vertically compressing the segment of the tongue that is forward of the placement of the orbital tongue shaping device side regions; the resulting reaction of the tongue is an expansion in lateral thickness in the segment of the tongue that is forward of the placement of the orbital tongue shaping device side regions, securing the orbital tongue shaping device on the tongue.

In yet another aspect, the orbital tongue shaping device can be made in an over-molding process, where the orbital tongue shaping device is fabricated of an internal rigid material and an external pliant material, where the internal rigid material provides structural support and the external pliant material provides patient comfort.

In regards to a method of fabrication a tongue attachment sheath of a tongue attachment assembly is fabricated in accordance with a method comprising steps of:
  obtaining a formation of a tongue of a patient;
  creating an interior portion of a mold from the obtained formation of the tongue of the patient;
  joining the interior portion of the mold and an exterior portion of the mold with one another forming a mold assembly; and
  fabricating the tongue attachment sheath using the mold assembly.

In a second aspect, the step of obtaining the formation of the tongue of the patient is accomplished using a scanning process.

In another aspect, the step of creating an interior portion of the mold from the obtained formation of the tongue of the patient is accomplished using a three-dimensional printing process.

In yet another aspect, the step of creating an interior portion of the mold from the obtained formation of the tongue of the patient is accomplished using a three-dimensional printing process.

In yet another aspect, the step of obtaining the formation of the tongue of the patient is accomplished using a casting process to create an impression.

In yet another aspect, the step of creating the interior portion of the mold from the obtained formation of the tongue of the patient is accomplished by taking a mold from the impression created by the casting process.

In yet another aspect, the method further comprises a step of integrating an air extraction passageway into the tongue attachment sheath.

In yet another aspect, the method further comprises a step of integrating a valve into the tongue attachment sheath, wherein the valve is in fluid communication with the air extraction passageway.

In yet another aspect, the method further comprises a step of forming a groove into the tongue attachment sheath.

In yet another aspect, the method further comprises a step of forming a groove into the tongue attachment sheath, wherein the groove circumscribes an air extraction passageway of the tongue attachment assembly enabling attachment of a secondary component in a direction that is substantially perpendicular to a longitudinal direction of the air extraction passageway.

In regards to another method of fabrication a tongue attachment sheath of a tongue attachment assembly is fabricated in accordance with a method comprising steps of:
  obtaining a digital model of a tongue of a patient;
  creating an interior surface shape of a tongue attachment sheath on a digital tongue sleeve model using the obtained digital model of the tongue of the patient;
  introducing an exterior surface shape of the tongue attachment sheath to the tongue sleeve model; and
  fabricating the tongue attachment sheath using the tongue sleeve model.

In yet another aspect, the step of obtaining the formation of the tongue of the patient is accomplished using a scanning process.

In yet another aspect, the step of fabricating the tongue attachment sheath is accomplished using a three-dimensional printing process.

In yet another aspect, the step of fabricating the tongue attachment sheath is accomplished using a three-dimensional printing process.

In yet another aspect, the step of obtaining the formation of the tongue of the patient is accomplished using a casting process to create an impression.

In yet another aspect, the step of creating an interior surface shape of a tongue attachment sheath on a digital tongue sleeve model using the obtained digital model of the tongue of the patient is accomplished by taking a mold from the impression created by the casting process and scanning the mold.

In yet another aspect, the method further comprises a step of integrating an air extraction passageway into the digital tongue sleeve model.

In yet another aspect, the method further comprises a step of integrating a valve into the digital tongue sleeve model, wherein the valve is in fluid communication with the air extraction passageway.

In yet another aspect, the method further comprises a step of forming a groove into the tongue attachment sheath.

In yet another aspect, the method further comprises a step of forming a groove into the tongue attachment sheath, wherein the groove circumscribes an air extraction passageway of the tongue attachment assembly enabling attachment of a secondary component in a direction that is substantially perpendicular to a longitudinal direction of the air extraction passageway.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, in which:

FIG. 11 presents a side elevation view of the apnea control device demonstrating proper positioning within an individual's mouth;

FIG. 12 presents a side elevation view of the tray interlock member engaged with the sheath interlock member;

FIG. 15 presents an isometric view of a dorsal side of a second exemplary tongue attachment member, the second exemplary tongue attachment member provides an attachment interface for any oral supporting device, including sleep apnea, a lip retention member, and the like;

FIG. 22 presents an isometric view of a dorsal side of a third exemplary tongue attachment member, the third exemplary tongue attachment member provides an attachment interface for any oral supporting device, including sleep apnea, a lip retention member, and the like;

Like reference numerals refer to like parts throughout the various views of the drawings.

DETAILED DESCRIPTION OF THE INVENTION

Figure 1:
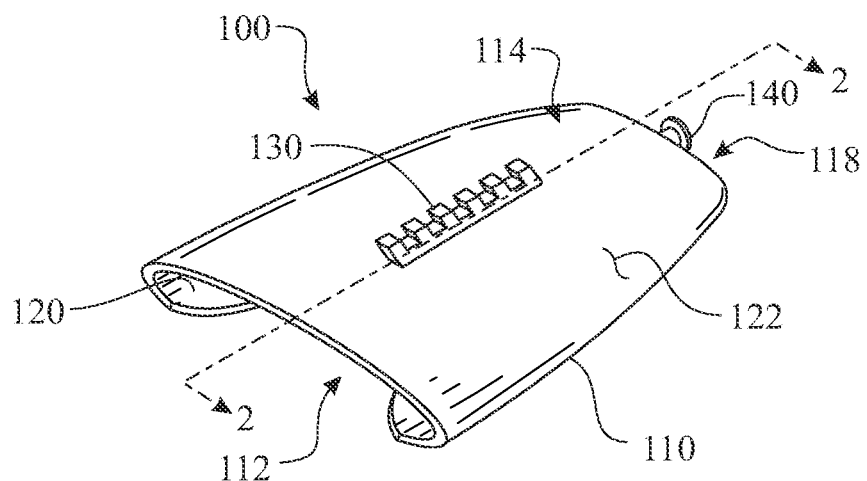
FIG. 1 presents an isometric view of a dorsal side of a first exemplary tongue attachment member of a sleep apnea control device.
Figure 2:
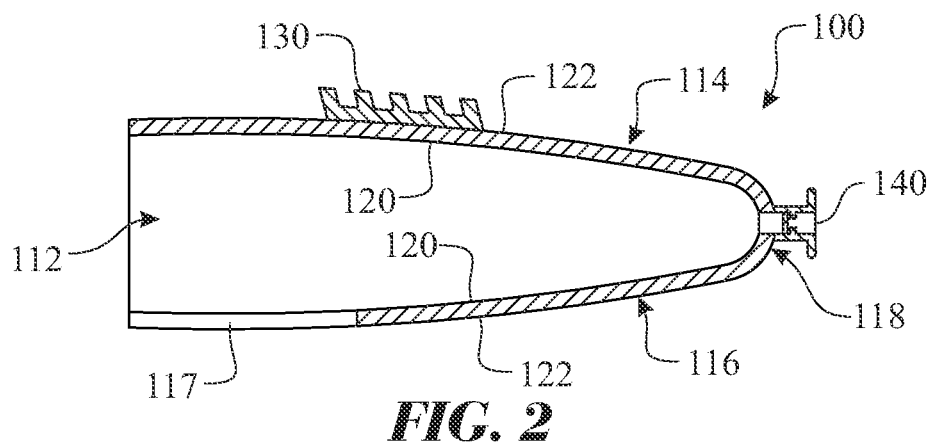
FIG. 2 presents a sectioned view of the tongue attachment member introduced in FIG. 1, the section being taken along section 2-2 of FIG. 1.
Figure 3:
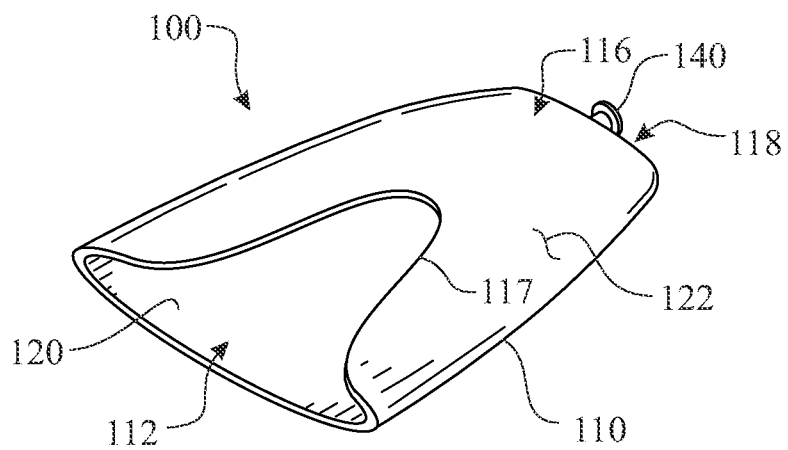
FIG. 3 presents an isometric view of a ventral side of the tongue attachment member.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

A sleep apnea control device is provided for the prevention of snoring and sleep apnea. The sleep apnea control device includes a tongue attachment subassembly 100 and a maxilla attachment subassembly 200, as illustrated in FIG. 11.

Figure 10:
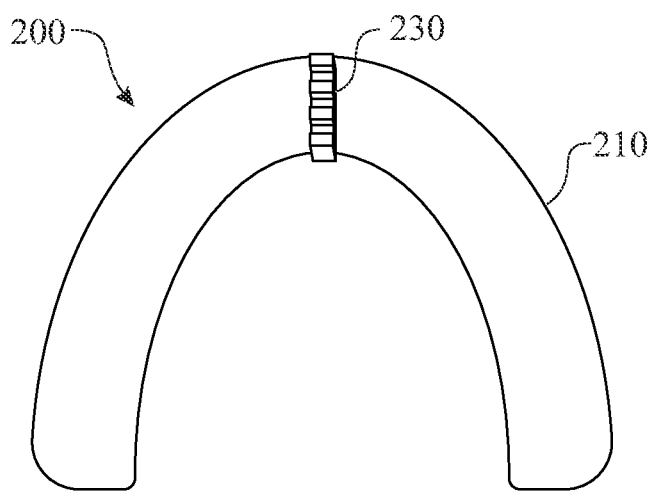
FIG. 10 presents a bottom side plan view of a maxilla attachment member of the apnea control device.

The tongue attachment subassembly 100 is detailed in FIGS. 1 through 9. The maxilla attachment subassembly 200 is detailed in FIG. 10. The tongue attachment subassembly 100 includes a sheath 110, wherein the sheath 110 is defined having a tongue receiving cavity 112 for insertion of an individual's tongue 300. The tongue attachment subassembly 100 can be defined having a dorsal side 114 and a ventral side 116. The sheath 110 can also be defined having an exterior surface 122 and a tongue engagement surface 120. An air extraction valve 140 is integrated into the sheath 110 at a sheath distal end 118. The illustrated air extraction valve 140 is only exemplary and it is understood that it can include any unidirectional valve known by those skilled in the art. The device may be fabricated from any of a plethora of known, non-toxic materials. The sheath 110 is fabricated of a pliant material, such as latex, silicone, rubber, and the like. The sheath 110 can be molded, thermally formed, or constructed using similarly known fabrication techniques.

Figure 7:
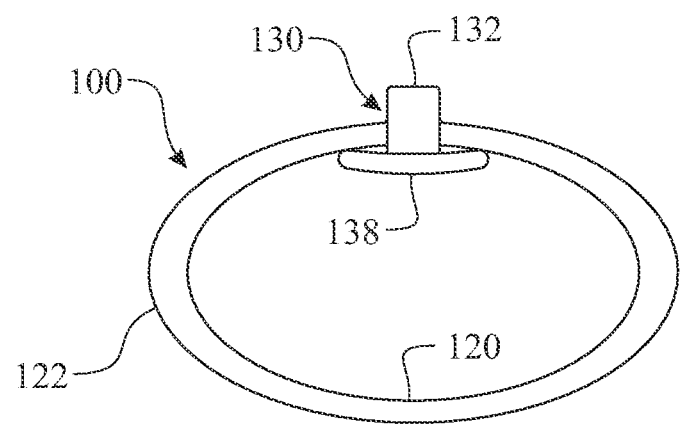
FIG. 7 presents an anterior elevation view of the tongue attachment member.

A sheath interlock member 130 is integrated into a dorsal side 114 portion of the sheath 110. Details of the sheath interlock member 130 are presented in FIG. 6. The sheath interlock member 130 includes an interlock ridge 132 having a series of interlock teeth 134 and interlock teeth-receiving receptacle 136 extending outward from the tongue engagement surface 120 of the dorsal side 114. The preferred design orients the interlock teeth 134 and interlock teeth-receiving receptacle 136 such that a base of each interlock teeth 134 is slightly forward of its top of the respective interlock teeth 134. The sheath interlock member 130 can be integrated into the sheath 110 during the fabrication of the tongue attachment subassembly 100 using the same material, using a different material, or joined in a post fabrication assembly step. The sheath interlock member 130 can include an optional interlock base portion 138 for attachment to the sheath 110. The interlock base portion 138 can be formed having an arched shape with a downward apex, wherein the apex applies additional pressure to the individual's tongue 300. The interlock ridge 132 is inserted through an aperture formed in the dorsal side 114 and attached using any adequate attachment means. An exemplary attachment bonds the interlock base portion 138 to the exterior surface 122 using a bonding media, as illustrated in FIG. 7. The sheath interlock member 130 is preferably constructed from a rigid material, such as plastic, hard rubber, nylon, and the like. The sheath interlock member 130 is preferably fabricated using a molding process, but it is recognized that the sheath interlock member 130 can be fabricated using any reasonable process respective to the material selection. The bonding can be provided using any bonding medium, using a heat staking process, using an ultrasonic welding process, and the like.

Figure 4:
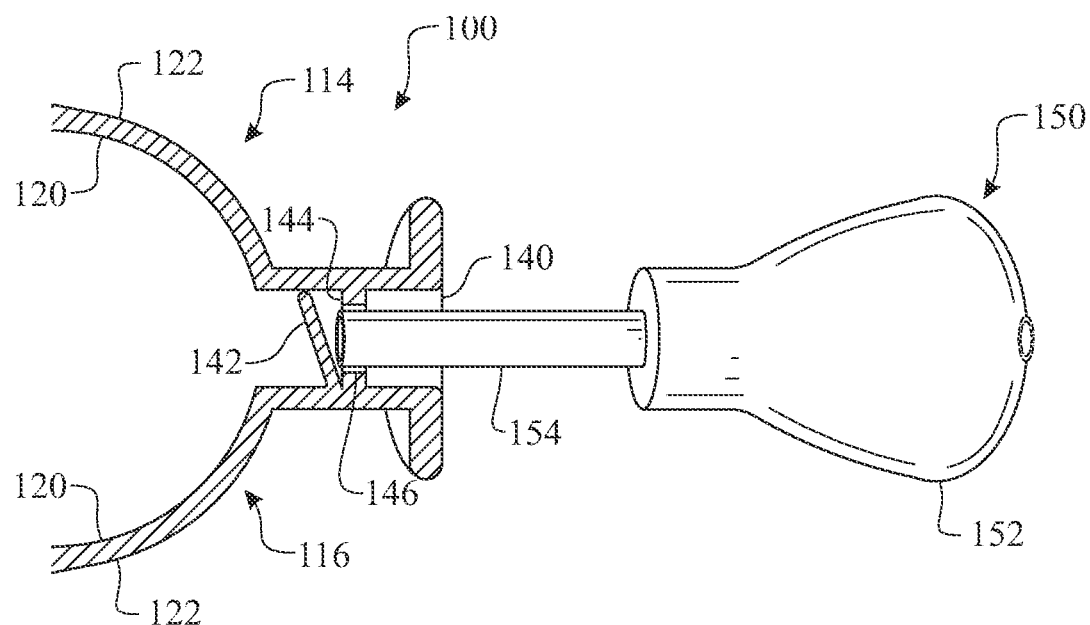
FIG. 4 presents an enlarged sectioned view of a distal end of the tongue attachment member, detailing an air removal system.
Figure 5:
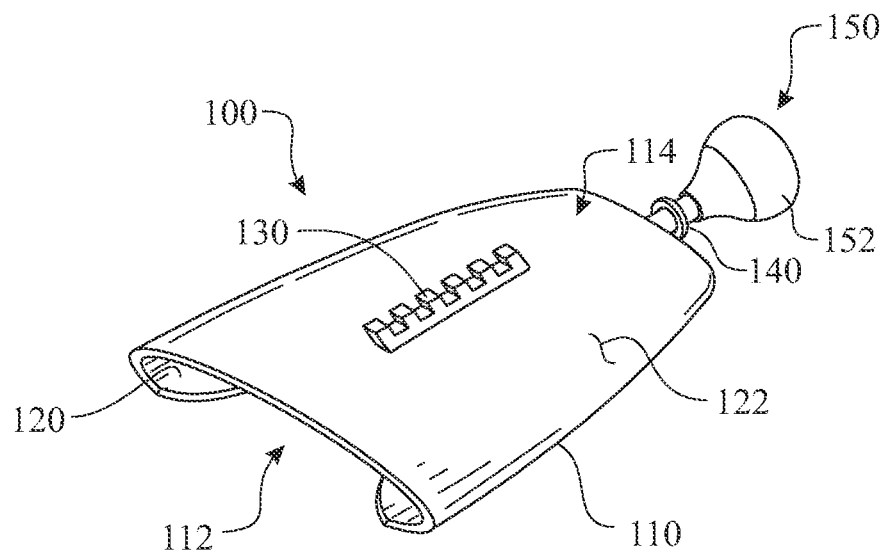
FIG. 5 presents an isometric view of the dorsal side of the tongue attachment member and the air removal system.
Figure 6:
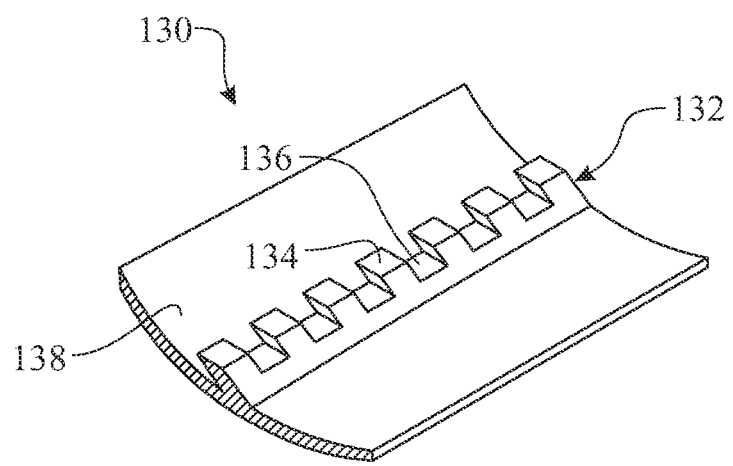
FIG. 6 presents an isometric view of a sheath interlock member.
Figure 8:
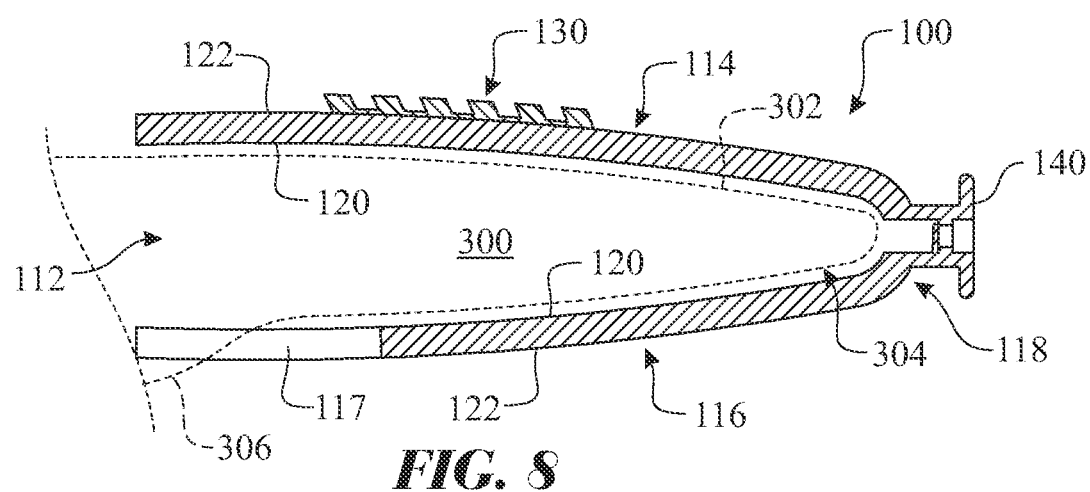
FIG. 8 presents a side sectioned view of the tongue attachment member taken along a longitudinal centerline, wherein the tongue attachment member is secured to an individual's tongue.
Figure 9:
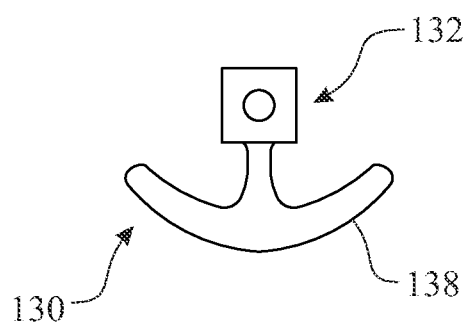
FIG. 9 presents an end elevation view of the sheath interlock member.

The tongue attachment subassembly 100 is placed over and secured to an individual's tongue 300 as illustrated in a FIGS. 8 and 11. A tongue base clearance 117 can be formed within the ventral side 116 of the sheath 110, providing a clearance for a tongue base 306. The tongue base clearance 117 is a recess in the ventral side 116 of the sheath 110, extending inward from an opening for the tongue receiving cavity 112. A securing seal is created by evacuating air from a gap 304 formed between a tongue surface 302 of the individual's tongue 300 and the tongue engagement surface 120. As the sheath 110 is placed upon the individual's tongue 300, air within the tongue receiving cavity 112 is displaced and a seal is created between the tongue surface 302 and a rear portion of sheath 110. A majority of the remaining air is removed using an air removal system. The air removal system includes an air extraction valve 140 and an air extraction device 150. The air extraction device 150 engages with the air extraction valve 140 to extract air from the gap 304. Details of the air removal system are illustrated in FIG. 4. The air extraction device 150 includes an air extraction bulb 152 in fluid communication with an air extraction pipette 154. In the exemplary embodiment, the air extraction pipette 154 is inserted through a unidirectional valve orifice 146 separating a unidirectional valve flap 142 from a unidirectional valve seal 144. This creates an airflow passage between the gap 304 and the air extraction bulb 152. The user would preferably squeeze the air extraction bulb 152 to discharge air from within the air extraction bulb 152 prior to insertion of the air extraction pipette 154 through the unidirectional valve orifice 146. Once inserted, the user would release the pressure from the air extraction bulb 152, thus causing the air extraction bulb 152 to extract air from the gap 304. The user then removes the air extraction device 150 from the air extraction valve 140. The unidirectional valve flap 142 naturally retracts to a sealed configuration, seating against the unidirectional valve seal 144. The removal of air from the gap 304 creates a vacuum, which secures the sheath 110 onto the individual's tongue 300. It is understood that although the illustrations present a removable air extraction device 150, the air extraction device 150 can alternately be integrated into the air extraction valve 140. The air extraction device 150 can be used to aid in the return of air into the air-extracted region to aid in removal of the tongue attachment subassembly 100 from the individual's tongue 300.

The maxilla attachment subassembly 200 is formed of a resilient material and shaped to be removably attached to a maxilla (upper jaw) 320. The maxilla attachment subassembly 200 includes a maxilla tray 210, which is formed in a "U-shape", contouring to the maxilla (upper jaw) 320. The maxilla tray 210 is defined having a maxilla tray's attachment side 220 and a maxilla tray's interlock side 222. The maxilla tray's interlock side 222 includes a recession formed into the maxilla tray 210 for receiving individual's teeth. The maxilla attachment subassembly 200 is fabricated having a tray interlock member 230 disposed upon the maxilla tray's interlock side 222 of the maxilla tray 210. The maxilla tray 210 is shaped to be removably attached to the maxilla (upper jaw) 320.

The maxilla tray 210 is secured by its shape and can optionally include one or more features to aid in the engagement with the individual's teeth. The maxilla tray 210 can be formed to mate with the maxilla (upper jaw) 320 by placing the maxilla attachment subassembly 200 into hot water, inserting the maxilla attachment subassembly 200 into the individual's mouth, and placing with finger pressure into an interior recession. This will shape the interior portion of the maxilla tray 210 to mate with the maxilla (upper jaw) 320. Another technique to form the maxilla tray 210 is to have a custom maxilla tray 210 fabricated by the individual's dentist or other oral health care professional. This technique allows the maxilla tray 210 to be custom fit for the user. The custom version of the maxilla attachment subassembly 200 would be fabricated in a manner similar to that for teeth whitening trays from their dentist. A tray interlock member 230 is positioned onto the maxilla tray 210 to interlock with the sheath interlock member 130 as illustrated in FIGS. 11 and 12. An interlock is formed by an engagement between the interlock teeth 134 of the sheath interlock member 130 and the interlock tooth receptacle 236 of the tray interlock member 230, and similarly with the engagement between the interlock tooth 234 of the tray interlock member 230 and the interlock teeth-receiving receptacle 136 of the sheath interlock member 130. The interlock between the sheath interlock member 130 and the tray interlock member 230 draws and maintains the individual's tongue 300 forward, to an extended tongue 310. The teeth engage by the angled relation of the between the interlock tooth 234 and the interlock teeth-receiving receptacle 136. The extended tongue 310 is positioned, resting upon teeth and/or gums of an individual's mandible (lower jaw) 322. The extended tongue 310 and the fixed position of the jaw will reduce or eliminate snoring and sleep apnea.

The sleep apnea control device can be removed from the individual's mouth by opening the individual's mouth, which separates the engaged sheath interlock member 130 and tray interlock member 230, removing the maxilla attachment subassembly 200, then releasing the vacuum holding the tongue attachment subassembly 100 and removing the tongue attachment subassembly 100 from the individual's tongue 300. The vacuum can be removed by squeezing the two sides of the tongue attachment subassembly 100 together to separate the rear edge from the individual's tongue 300 or by inserting the air extraction pipette 154 into the air extraction valve 140, which separates the unidirectional valve flap 142 from the unidirectional valve seal 144, and squeezing the air extraction bulb 152 to inject air into the tongue receiving cavity 112. Upon combining the fixed, forward location 310 of a user's tongue 300 with adequate, uniform suction between the user's tongue 300 and the sheath 310, a comfortable and efficient oral medical apparatus used in the prevention of snoring and sleep apnea is realized.

Although the exemplary embodiments include the air extraction valve 140, it is understood that the tongue attachment subassembly 100 can be fabricated excluding the air extraction valve 140. The user would manually remove the air within the tongue surface 302 by sucking the air therefrom.

Figure 13:
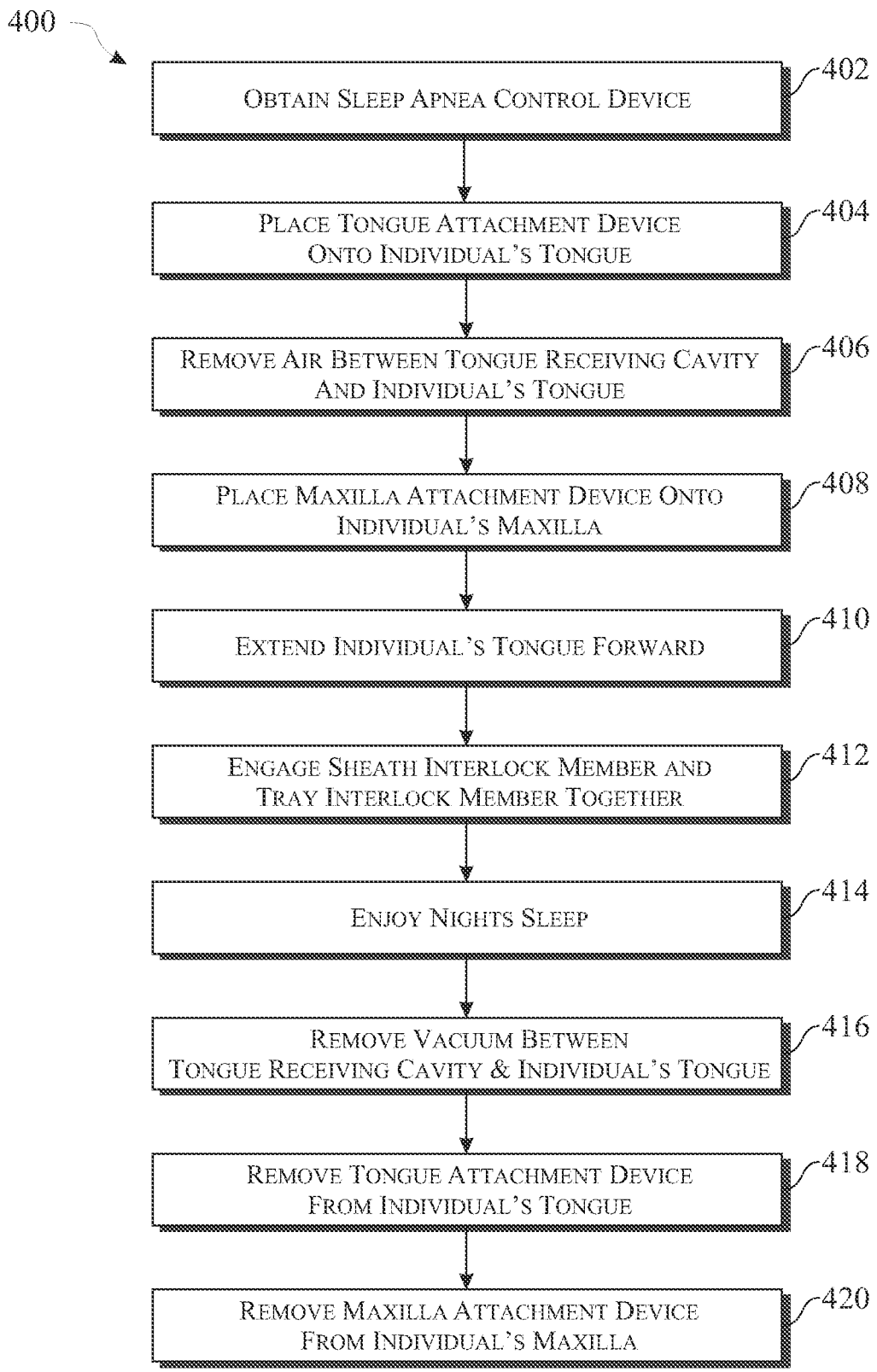
FIG. 13 presents an exemplary flow diagram illustrating a method of use of the sleep apnea control device.

An exemplary sleep apnea control method flow diagram 400 is presented in FIG. 13. The method initiates with a step of the individual obtaining the sleep apnea control device (step 402), the device comprising the tongue attachment member 100 and the maxilla attachment subassembly 200. The user places their tongue 300 into the tongue receiving cavity 112 in accordance with a tongue attachment subassembly installation step (step 404). The user removes a majority of the residual air remaining between the tongue engagement surface 120 of the tongue receiving cavity 112 and the individual's tongue 300 in accordance with an air removal step (step 406). The maxilla attachment subassembly 200 is positioned, placing the maxilla tray's attachment side 220 against the individual's maxilla (upper jaw) 320 in accordance with a maxilla attachment subassembly installation step (step 408). The process continues with the user extending their tongue 300 (tongue extending step 410) and engaging the sheath interlock member 130 and the tray interlock member 230 together, referred to as an interlock engagement step (step 412). At this point, the device is ready for use and the individual can enjoy a night's sleep (step 414). Upon completion of use, the individual disengages the interlock provided between the sheath interlock member 130 and the tray interlock member 230. The user opens their mouth and removes the vacuum provided between the tongue receiving cavity 112 and the individual's tongue 300 in accordance with a vacuum removal step (step 416). Once released, the user removes the tongue attachment subassembly 100 from their tongue 300 per a tongue attachment subassembly removal step (step 418). The use is concluded with the removal of the maxilla attachment subassembly 200 from the individual's maxilla (upper jaw) 320 in accordance with a maxilla attachment subassembly removal step (step 420). The user then stores the sleep apnea control device for future use.

Figure 14:
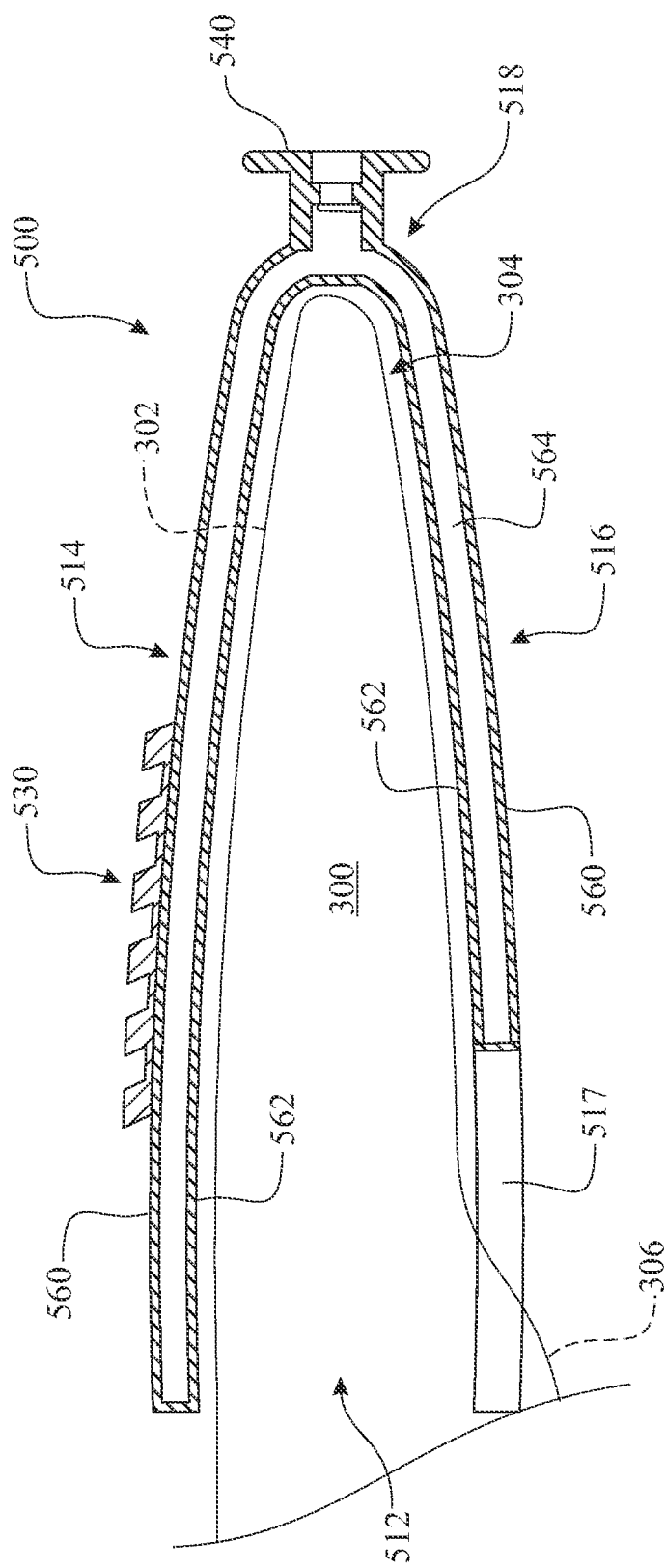
FIG. 14 presents a side sectioned view of an alternate tongue attachment member taken along a longitudinal centerline, wherein the tongue attachment member is secured to an individual's tongue.
Figure 15:
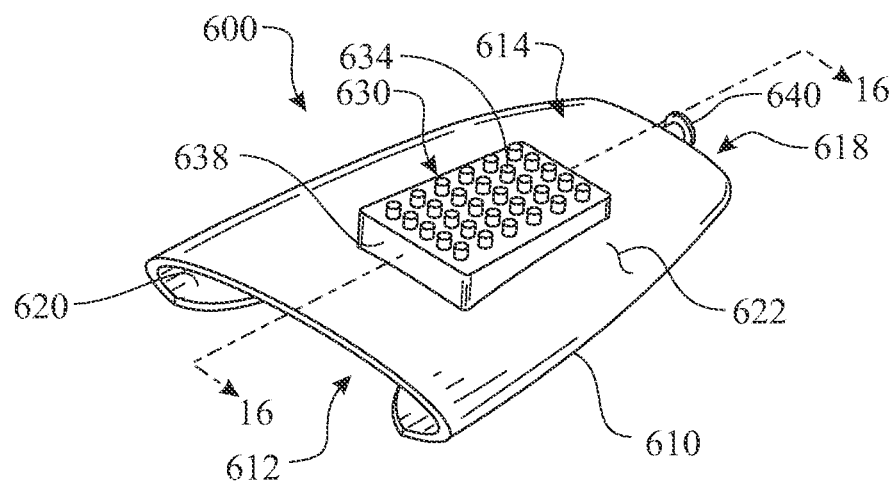
Figure 16:
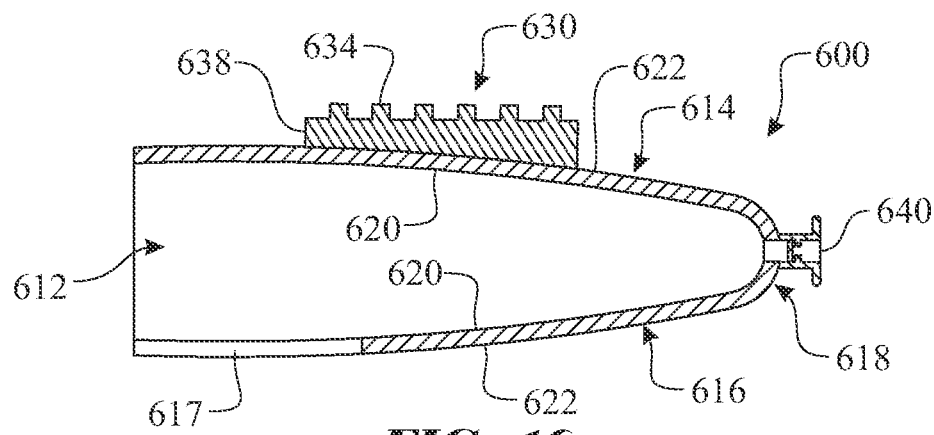
FIG. 16 presents a sectioned view of the second tongue attachment member taken along section 16-16 of FIG. 15.
Figure 17:
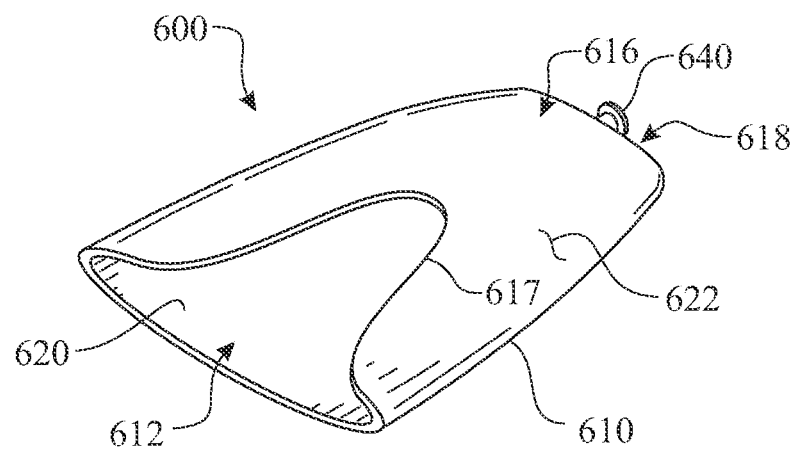
FIG. 17 presents an isometric view of a ventral side of the second tongue attachment member.
Figure 18:
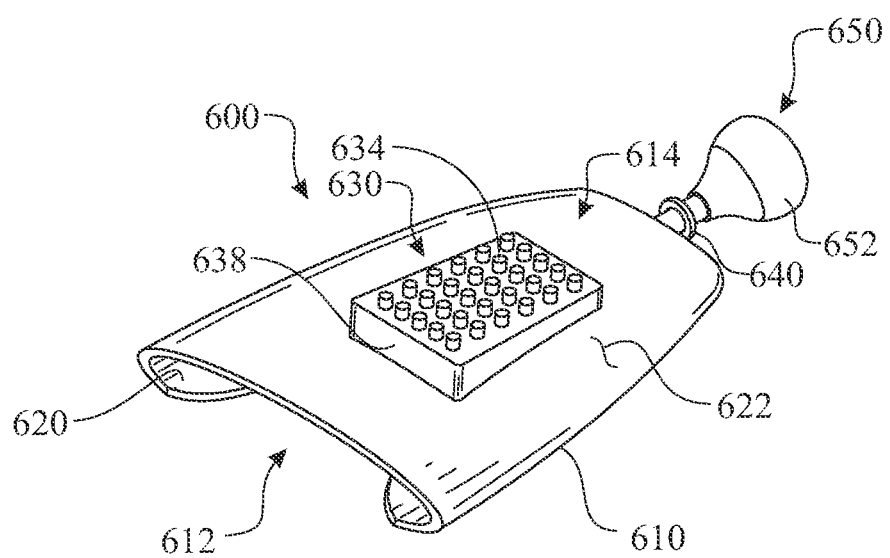
FIG. 18 presents an isometric view of the dorsal side of the second tongue attachment member and the air removal system.

An alternate embodiment of the tongue embracing member 100 is presented as a tongue embracing member 500 illustrated in FIG. 14. Like features of tongue embracing member 500 and tongue embracing member 100 are numbered the same except preceded by the numeral '5'. The tongue embracing member 500 utilizes an internally provided suction compared to the tongue embracing member 100, which utilizes an externally applied suction. The tongue embracing member 500 is fabricated having a bladder air chamber 564 formed therein. The bladder air chamber 564 is defined by a bladder interior wall 562 formed on the tongue-contacting portion of the tongue embracing member 500 and a bladder exterior wall 560 formed on the external portion of the tongue embracing member 500. The user would remove the air from within the bladder air chamber 564 drawing and securing the tongue embracing member 500 onto the individual's tongue 300. The tongue embracing member 500 would be shaped to include a tongue base clearance 117.

The tongue embracing member 100 can be adapted to include an array arrangement of interlocking pins 634, wherein the adapted assembly is referred to as a tongue embracing member 600 and is illustrated in FIGS. 15 through 18. Like features of tongue embracing member 600 and tongue embracing member 100 are numbered the same except preceded by the numeral '6'. Although the tongue embracing member 600 is illustrated formed having a solid material, it is understood that the tongue embracing member 600 can be formed having a bladder similar to the tongue embracing member 500.

Figure 19:
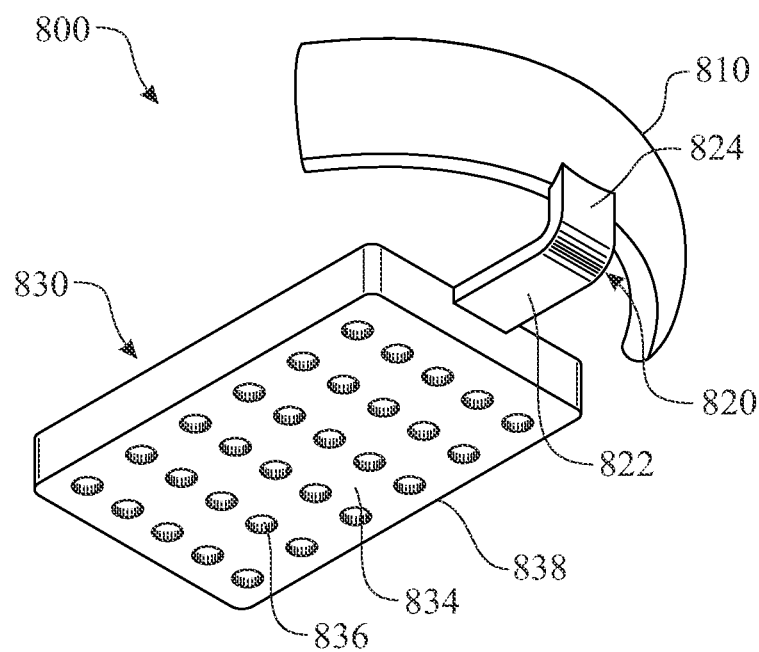
FIG. 19 presents an isometric view of an exemplary maxilla lip retention subassembly for use in conjunction with the second tongue attachment member.

The array arrangement of interlocking pins 634 extends perpendicularly from an interlock base portion 638. The array arrangement of interlocking pins 634 provides longitudinal and axial adjustments between the tongue embracing member 600 and another component. One exemplary component for use in conjunction with the tongue embracing member 600 would be a maxilla lip retention subassembly 800, which is introduced in FIG. 19. The maxilla lip retention subassembly 800 includes a lip retention subassembly interlock member 830 distally attached to a lip retention section 810 by a maxilla lip retention positioning arm 820. The maxilla lip retention positioning arm 820 can be designed having any suitable shape to appropriately position the lip retention section 810 when the maxilla lip retention subassembly 800 is attached to the tongue embracing member 600. The exemplary maxilla lip retention positioning arm 820 is shaped to include a positioning arm lateral arm 822 extending forward from the interlock base portion 638 and a positioning arm riser arm 824 extending downward from the lip retention section 810. The lip retention subassembly interlock member 830 can be provided in any configuration to detachably mate with the selected design of the sheath interlock member 630.

Figure 21:
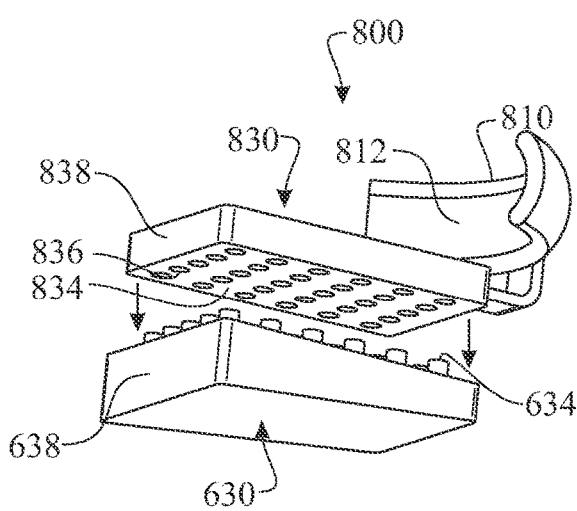
FIG. 21 presents an isometric view of the maxilla lip retention subassembly being attached to the tongue attachment member.
Figure 22:
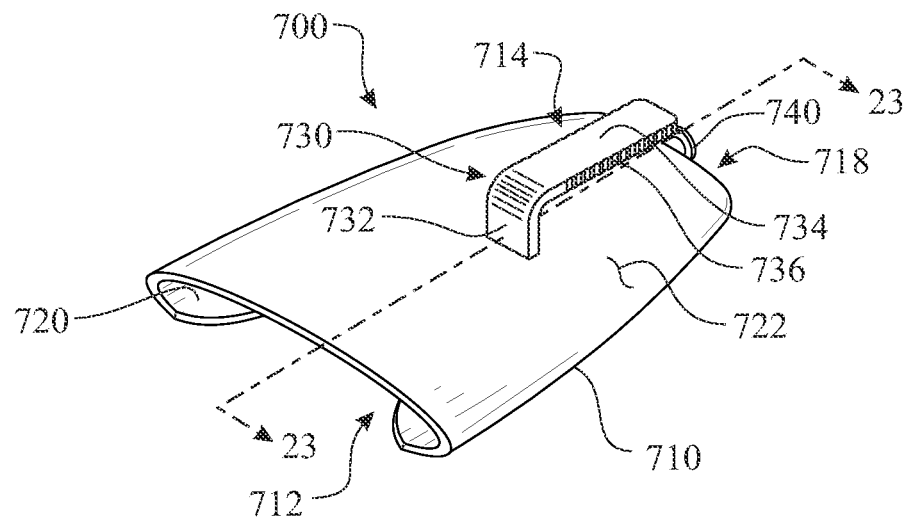
Figure 23:
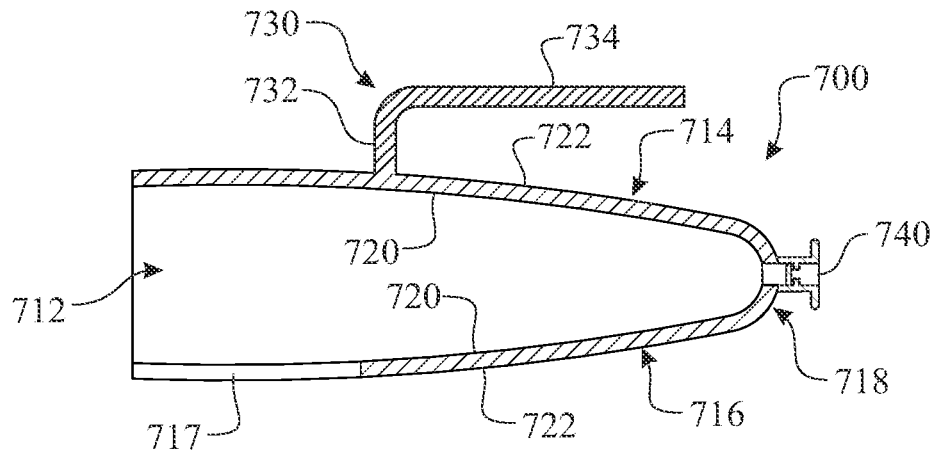
FIG. 23 presents a sectioned view of the third tongue attachment member taken along section 23-23 of FIG. 22.
Figure 24:
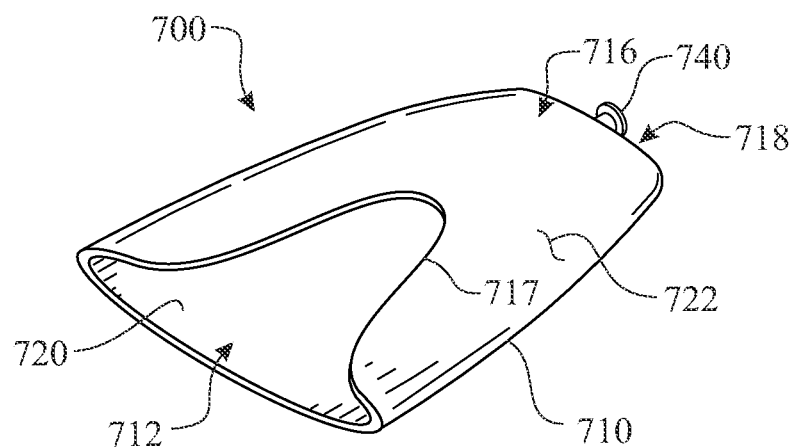
FIG. 24 presents an isometric view of a ventral side of the third tongue attachment member.
Figure 25:
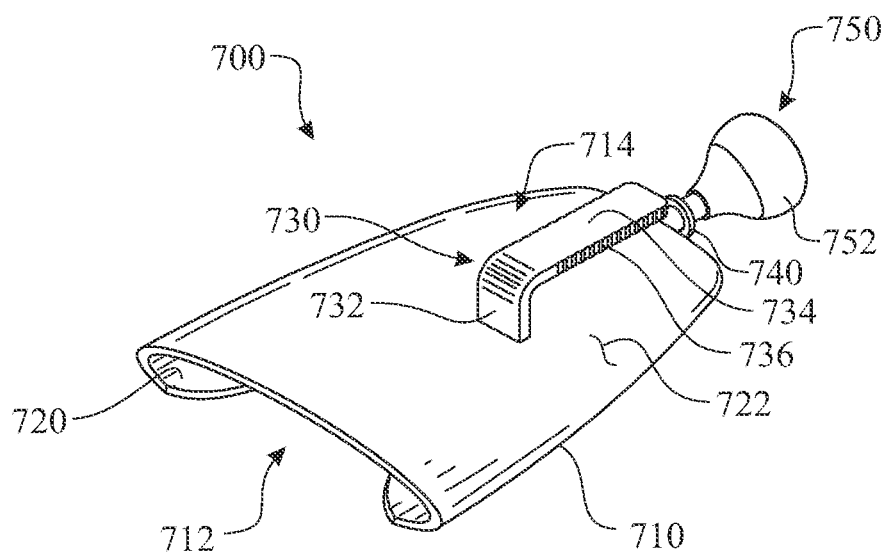
FIG. 25 presents an isometric view of the dorsal side of the third tongue attachment member and the air removal system.

The lip retention subassembly interlock member 830 includes an array of interlock pin receptacles 836 extending inward from an interlocking member contact surface 834 of an interlock base portion 838. The array of interlock pin receptacles 836 is arranged to detachably engage with the array of interlock pins 634. The array enables the user to positionally adjust the maxilla lip retention subassembly 800 in either or both a longitudinal and/or a lateral direction. The user would align the array of interlock pin receptacles 836 with the array of interlock pins 634 at the desired position and engage them accordingly as illustrated in FIG. 21.

Figure 20:
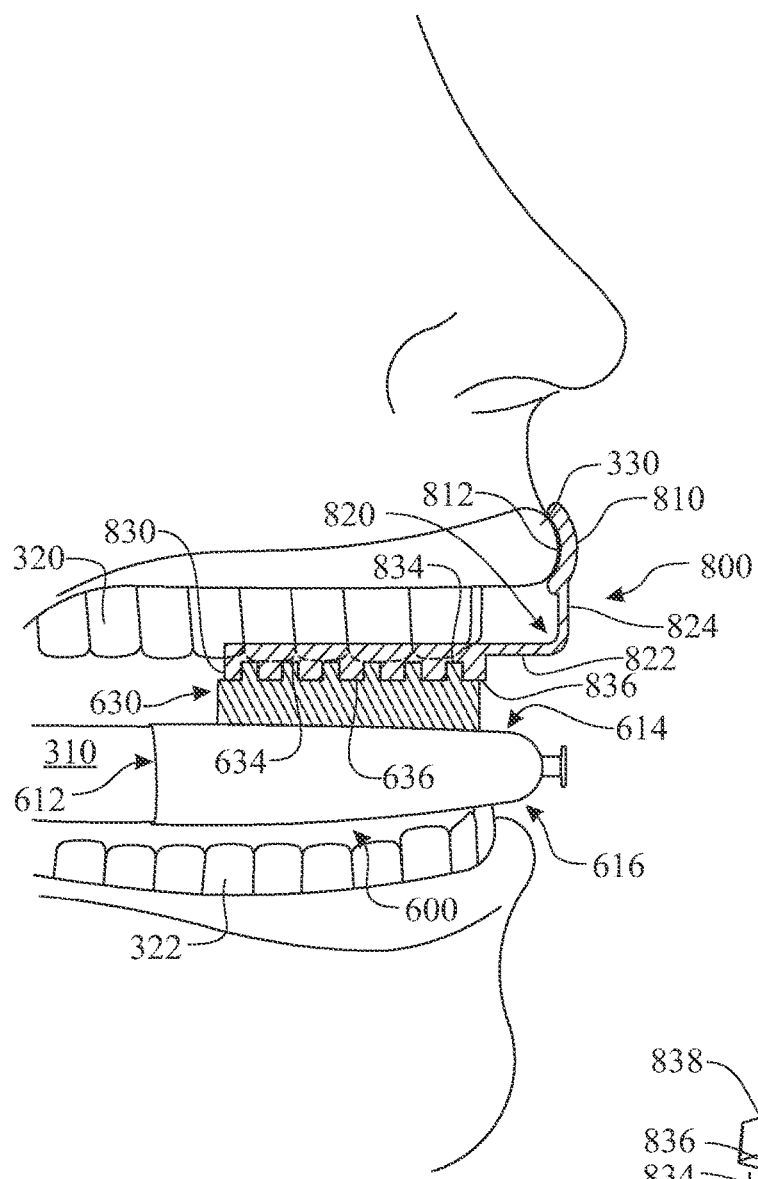
FIG. 20 presents a partially sectioned side view of the maxilla lip retention subassembly taken along a longitudinal centerline shown in use, wherein the maxilla lip retention subassembly is adapted to the secured tongue attachment member.

The exemplary maxilla lip retention subassembly 800 is shown in use in FIG. 20. The lip retention subassembly interlock member 830 of the maxilla lip retention subassembly 800 is engaged with the sheath interlock member 630 of the tongue embracing member 600. The user can positionally adjust the lip retention subassembly interlock member 830 respective to the sheath interlock member 630 to extend or retract the lip retention section 810. The tongue embracing member 600 would be secured to the tongue 310 of the patient as previously described. The lip retention subassembly interlock member 830 can be attached to the sheath interlock member 630 either prior to or subsequent to attachment of the tongue embracing member 600 to the tongue 310. The lip retention section 810 would retain an upper lip 330 of the patient in a desired position. The assembly between the maxilla lip retention subassembly 800 and the tongue embracing member 600 would additionally retain the tongue 310 in a desired position. The lip retention section 810 would be fabricated of a pliant material to ensure comfort during use. The pliant material can be silicone, rubber, nylon, wax, plastic, and the like. The lip retention section 810 would preferably be formed in a "C" shape. The lip retention surface 812 can be formed having an arch to improve the support of the upper lip 330.

Although the exemplary embodiment of the lip retention section 810 contacts the upper lip 330 of the individual, it is understood that the lip retention section 810 can be shaped to contact a gum line of the individual for applications where the goal is to govern a position of the tongue 310.

It is understood that the maxilla attachment device 200 can be adapted for use with the tongue embracing member 600 by replacing the tray interlock member 230 with the lip retention subassembly interlock member 830.

The tongue embracing member 100 can be adapted to include a sheath interlock member 730, wherein the adapted device is referred to as a tongue embracing member 700 and is illustrated in FIGS. 22 through 25. Like features of tongue embracing member 700 and tongue embracing member 100 are numbered the same except preceded by the numeral '7'. Although the tongue embracing member 700 is illustrated formed having a solid material, it is understood that the tongue embracing member 700 can be formed having a bladder similar to the tongue embracing member 500.

The tongue embracing member 700 provides a sheath interlock member 730 in a form of a cantilevered member that extends forward above an exterior surface 722 of a dorsal side 714 of a sheath 710. The sheath interlock member 730 includes an interlock member riser segment 732 preferably extending generally perpendicular from the exterior surface 722. The interlock member riser segment 732 transitions into an interlock member engagement segment 734, which is preferably oriented in a parallel arrangement with a longitudinal axis of the sheath 710. An interlock member positioning feature 736 comprises a series of notches along at least one of an edge, an upper surface, and a lower surface of the interlock member engagement segment 734. The interlock member positioning feature 736 is provided to engage with a mating feature to axially position a mating member.

Figure 26:
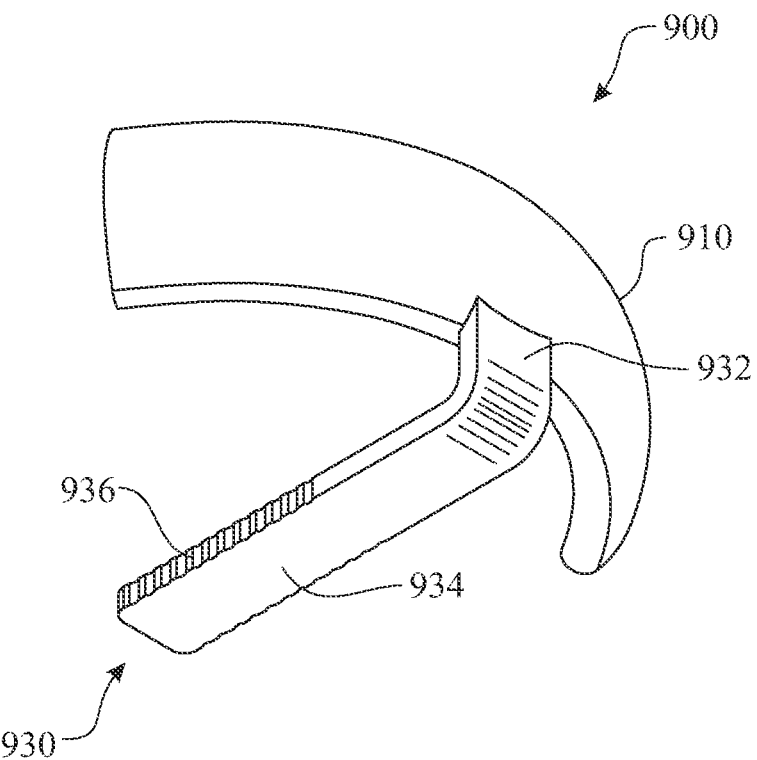
FIG. 26 presents an isometric view of an exemplary maxilla lip retention subassembly for use in conjunction with the third tongue attachment member.
Figure 28:
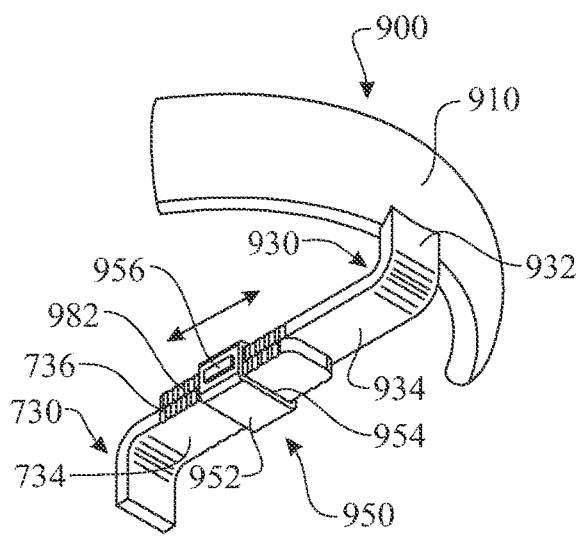
FIG. 28 presents an isometric view of the maxilla lip retention subassembly attached to the tongue attachment member in preparation for use.
Figure 27:
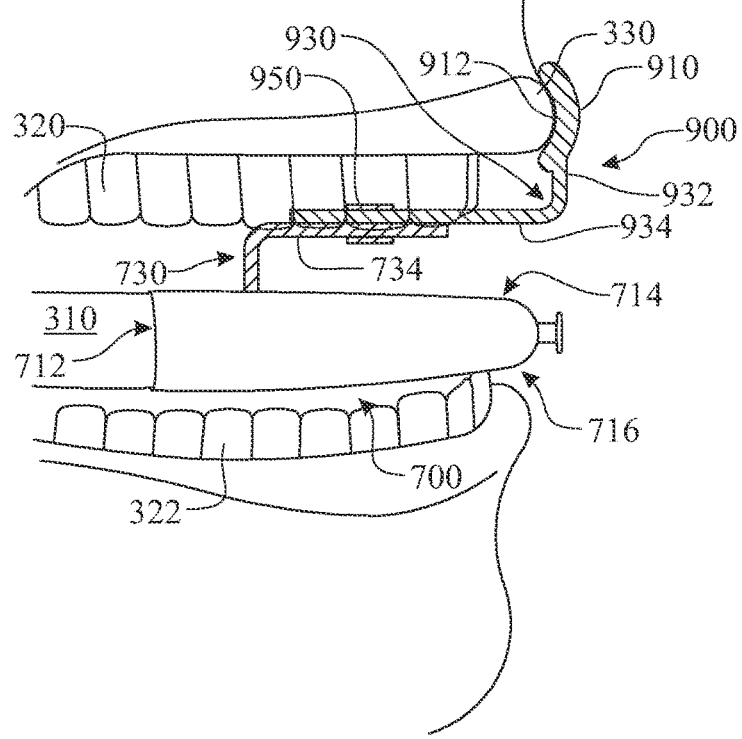
FIG. 27 presents a partially sectioned side view of the maxilla lip retention subassembly taken along a longitudinal centerline shown in use, wherein the maxilla lip retention subassembly is adapted to the secured tongue attachment member.
Figure 29:
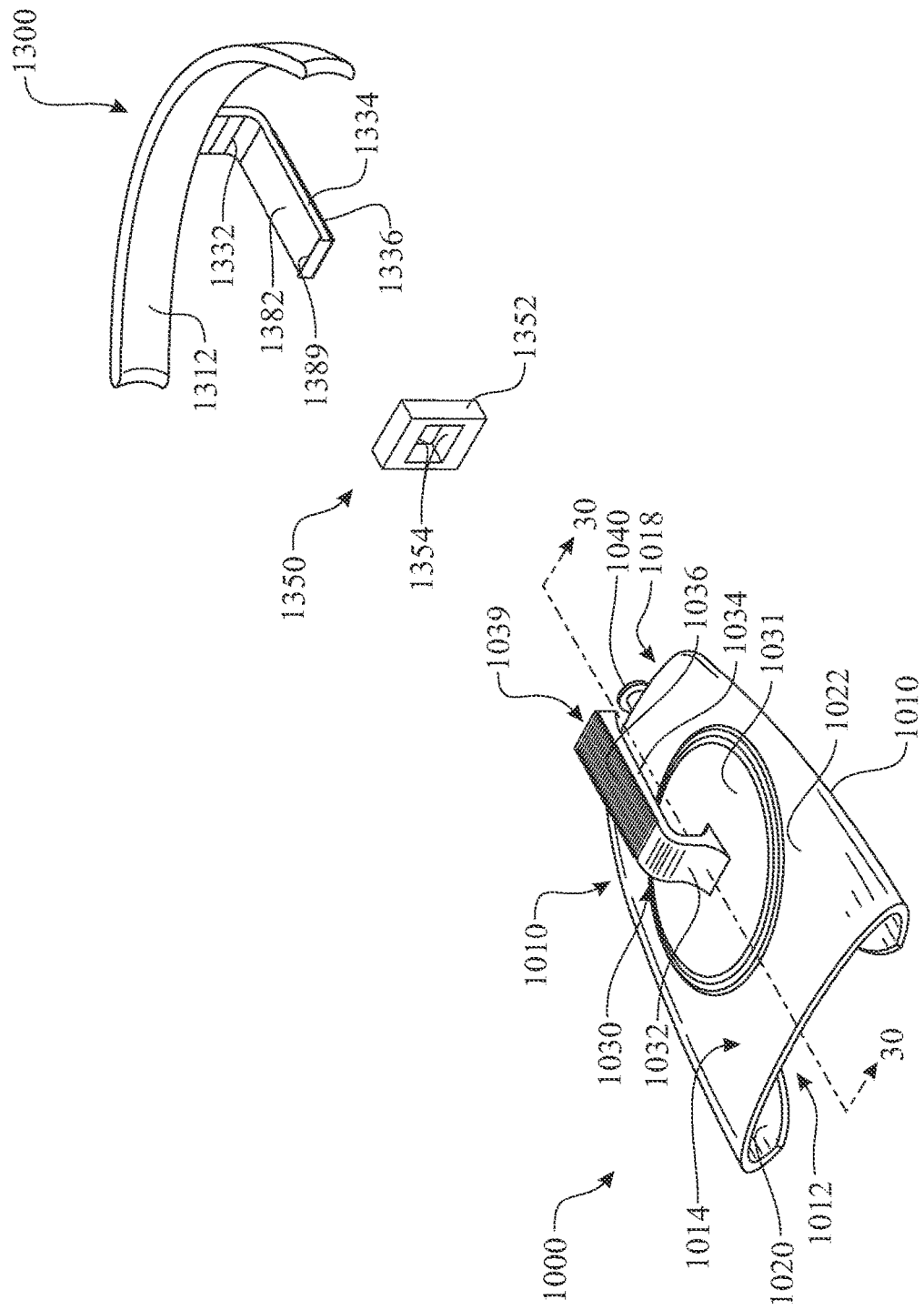
FIG. 29 presents an isometric exploded assembly view of a tongue placement and retention system employing fourth exemplary tongue attachment member, a maxilla lip retention device and a position retaining member, wherein the fourth exemplary tongue attachment member is a variant of the third exemplary tongue attachment member introduced in FIG. 22, wherein a sheath interlock member is assembled to the tongue attachment member body by an overmolded section.
Figure 30:
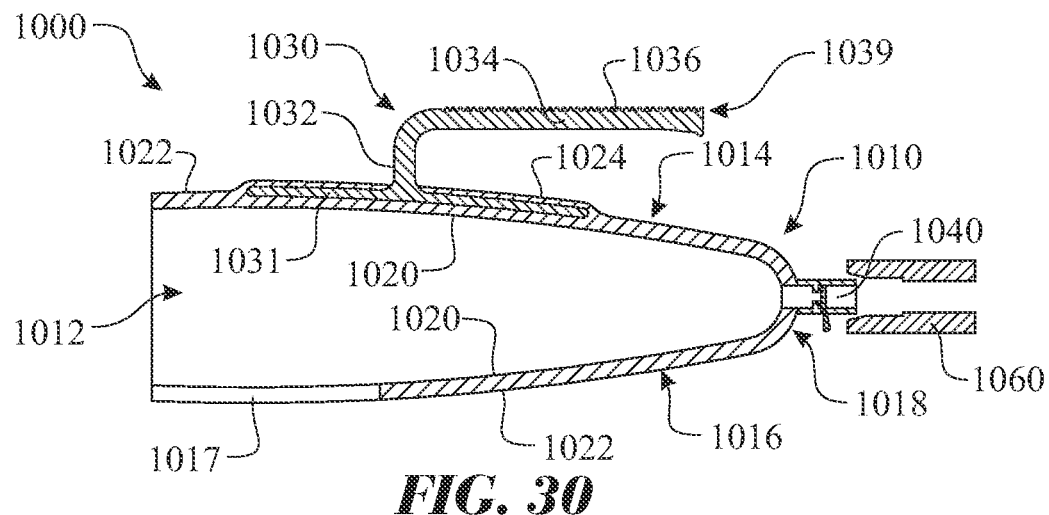
FIG. 30 presents a sectioned view of the fourth tongue attachment member taken along section 30-30 of FIG. 29, wherein the illustration presents a bulb air extraction tube of an air extraction device prior to insertion onto an air extraction valve.
Figure 31:
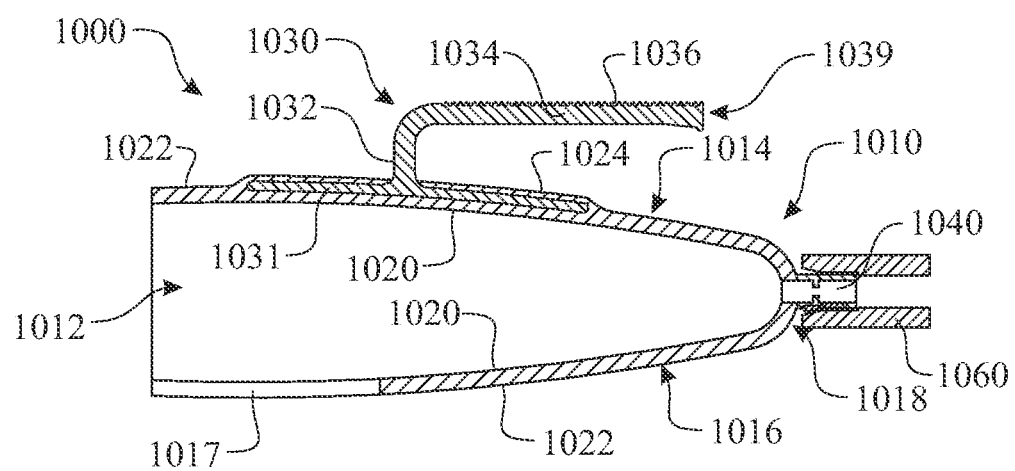
FIG. 31 presents a sectioned view of the fourth tongue attachment member taken along section 30-30 of FIG. 29, wherein the illustration presents the bulb air extraction tube of the air extraction device following insertion onto the air extraction valve.

The maxilla lip retention subassembly 800 can be modified to include a variation of the lip retention subassembly interlock member 830, wherein the modified assembly is referred to as a maxilla lip retention subassembly 900 and is illustrated in FIGS. 26 through 28. Like features of the maxilla lip retention subassembly 900 and maxilla lip retention subassembly 800 numbered the same except preceded by the numeral '9'. The maxilla lip retention subassembly 900 is one exemplary component for use in conjunction with the tongue embracing member 700. The maxilla lip retention subassembly 900 includes a maxilla lip retention positioning arm 930 extending from a lower edge of a lip retention section 910. The maxilla lip retention positioning arm 930 can be designed having any suitable shape to appropriately position the lip retention section 910 when the maxilla lip retention subassembly 900 is attached to the tongue embracing member 700. The exemplary maxilla lip retention positioning arm 930 is shaped to include a positioning arm riser arm 932 extending downward from the lip retention section 910 transitioning into a positioning arm lateral arm 934 which extends rearward and substantially perpendicular to the positioning arm riser arm 932. The maxilla lip retention positioning arm 930 can be provided in any configuration to adjustably and/or detachably mate with the selected design of the sheath interlock member 730.

The positioning arm lateral arm 934 would be positioned parallel to the interlock member engagement segment 734 and secured to one another using a position retaining member 950. The position retaining member 950 can be a separate member or integrated into one of the interlock member engagement segment 734 or the positioning arm lateral arm 934. The position retaining member 950 comprises a position retaining member body 952 formed having a series of walls defining a position retaining member body interior surface 954, wherein the position retaining member body interior surface 954 at least partially circumscribes the combined positioning arm lateral arm 934 and interlock member engagement segment 734. A position retaining member position locking element 956 can be integrated along one or more sides of the position retaining member 950, wherein the position retaining member position locking element 956 releasably engages with at least one of the interlock member positioning feature 736 and notched or ridged surface 936 to secure the maxilla lip retention positioning arm 930 in an axial positional relation with the sheath interlock member 730. The position retaining member position locking element 956 can be designed and operate in conjunction with any locking device known by those skilled in the art.

The exemplary embodiment presents two planar arms arranged in slideable contact with one another. It is understood that one arm can be provided in a form of a channel and the mating arm can be provided in a form of a rail, wherein the rail is slideably assembled within an interior portion of the channel. One of the two members can include a series of recessions that would engage with one or more position locking bosses.

The exemplary maxilla lip retention subassembly 900 is shown in use in FIG. 27. The user can positionally adjust the maxilla lip retention subassembly 900 respective to the tongue embracing member 700 by adjusting the longitudinal relation between the positioning arm lateral arm 934 and the interlock member engagement segment 734. The longitudinal position between the positioning arm lateral arm 934 and the interlock member engagement segment 734 would be retained by the position retaining member 950. The exemplary position retaining member 950 includes a pair of position retaining member position locking element 956, each position retaining member position locking element 956 being located on each side thereof. The position retaining member position locking element 956 engages with each of the interlock member positioning feature 736 and interlocking member contact surface 982 to limit any axial motion between the two arms 982, 934. The tongue embracing member 700 would be secured to the tongue 310 of the patient as previously described. The positioning between the interlock member engagement segment 734 and the positioning arm lateral arm 934 either prior to or subsequent to attachment of the tongue embracing member 700 to the tongue 310. The lip retention section 910 would retain the upper lip 330 of the patient in the desired position. The assembly between the maxilla lip retention subassembly 900 and the tongue embracing member 700 would additionally retain the tongue 310 in a desired position. The lip retention section 910 would be fabricated in a similar manner to the fabrication of the lip retention section 810 as previously described.

A tongue embracing member 1000, illustrated in FIGS. 29 through 33, introduces advantages over the tongue embracing member 700. Like features of the tongue embracing member 1000 and tongue embracing member 700 are numbered the same except preceded by the numeral '10'. The sheath interlock member 1030 is fabricated of a substantially rigid material, such as a rigid plastic. The sheath 1010 is fabricated of a pliant material, such as silicone. The differences in material properties deviates options for manufacturing from a single injection molding process. In the exemplary embodiment, the sheath interlock member 1030 includes a sheath interlock member base 1031 for assembly to the sheath 1010. The sheath interlock member 1030, more specifically, the sheath interlock member base 1031, can be assembled to the sheath 1010 using a two step process. The sheath interlock member 1030 would be fabricated using a first molding process; forming a substantially rigid material into the sheath interlock member 1030. The sheath interlock member 1030 would be assembled to the sheath 1010 by overmolding the sheath interlock member base 1031 onto the dorsal side 1014 of the sheath 1010. A sheath interlock member overmolded retention feature 1024 would encapsulate the sheath interlock member base 1031 over the sheath 1010, or in an alternative, the sheath interlock member base 1031 would be sandwiched between the sheath interlock member overmolded retention feature 1024 and a main body of the sheath 1010. This is best shown in the cross sectioned views illustrated in FIGS. 30 and 31.

The sheath interlock member 1030 includes additional features similar to the sheath interlock member 730 adapted for an adjustable assembly between the sheath interlock member 1030 and a maxilla lip retention device 1300 (introduced in FIGS. 37 through 41). An interlock member riser segment 1032 extends generally perpendicular from an upper surface of the sheath interlock member base 1031. An interlock member engagement segment 1034 extends generally perpendicular to the interlock member riser segment 1032 or generally parallel to the sheath interlock member base 1031. The sheath interlock member 1030 would be oriented having the interlock member engagement segment 1034 extending in a forward direction and located above, parallel to, and in alignment with a longitudinal axis of the sheath 1010. An interlock member positioning feature 1036 can be formed on a surface of the interlock member engagement segment 1034, wherein the surface of the interlock member engagement segment 1034 is designed to engage with a mating surface of a positioning arm lateral segment 1334 (introduced in FIGS. 37 through 41) of the maxilla lip retention positioning arm 1330. Details of the interlock member positioning feature 1036 will be introduced when describing an interlock member positioning feature 1236 of a sheath interlock member 1230 (introduced in FIGS. 37 through 41) later herein.

Figure 32:
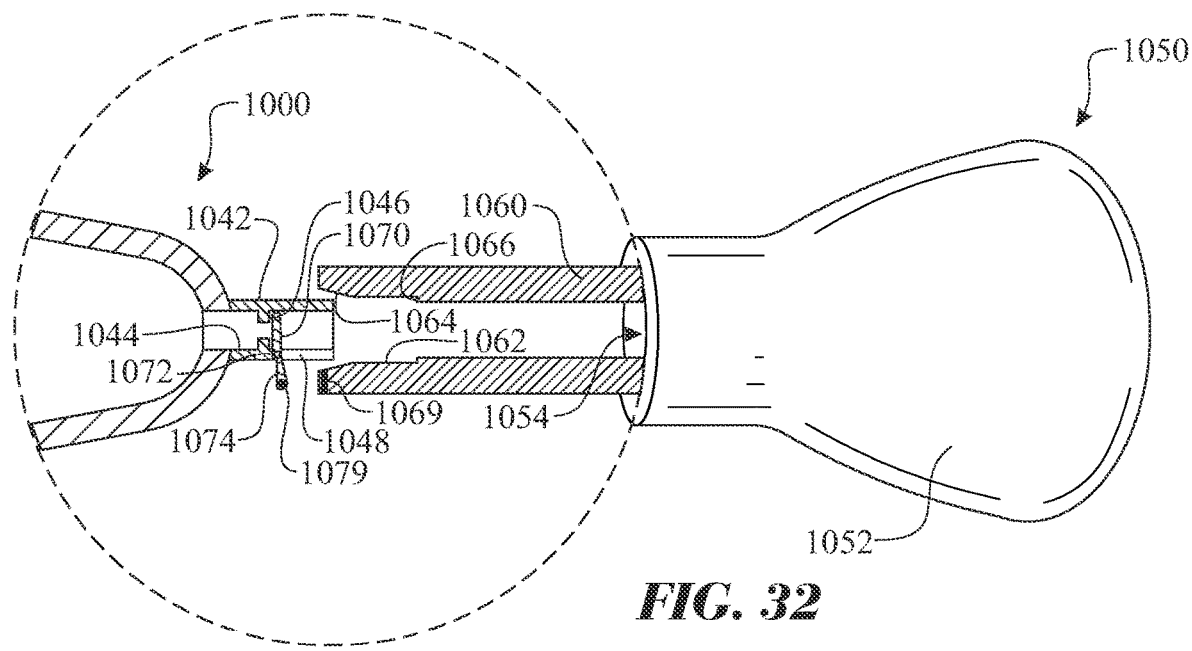
FIG. 32 presents an enlarged, partially sectioned view of the air extraction valve and the associated air removal system, wherein the illustration presents the bulb air extraction tube of the air extraction device prior to insertion onto the air extraction valve.
Figure 33:
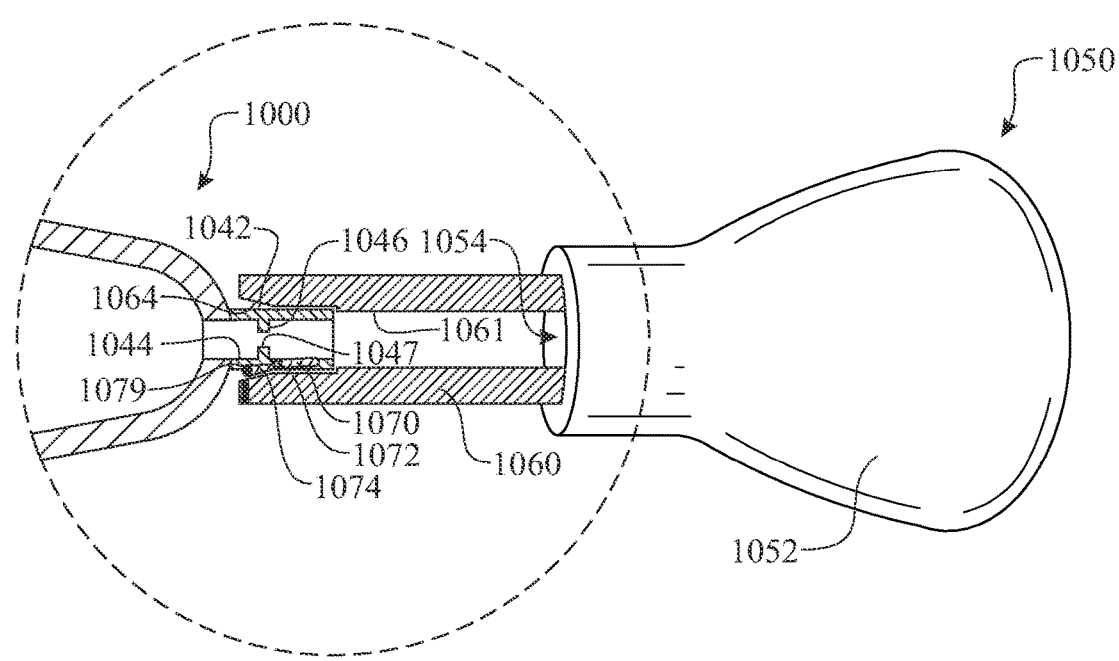
FIG. 33 presents an enlarged, partially sectioned view of the air extraction valve and the associated air removal system, wherein the illustration presents the bulb air extraction tube of the air extraction device following insertion onto the air extraction valve.

The tongue embracing member 1000 introduces a unique air extraction valve 1040, which is best shown in FIGS. 32 and 33. The tongue embracing member 1000 is retained upon the individual's tongue 300 by creating a vacuum in the space between an interior surface 1020 of the sheath 1010 and a tongue surface 302 of the individual's tongue 300. The air extraction valve 1040 must be designed with considerations of the vacuum. A common valve configuration pivots the unidirectional valve flap 142 inward, as shown in FIG. 4. It is noted that the employment of the vacuum could introduce a force that may draw the unidirectional valve flap 142 inward. This could introduce an unwarranted leak through the valve. The air extraction valve 1040 introduces an alternative valve configuration that is adapted with considerations of the implied vacuum forces.

The air extraction valve 1040 includes a valve flap 1070 that is pivotally assembled to the primary tubular structure of the air extraction valve 1040 by a valve hinge pin 1072. The valve flap 1070 is designed to pivot outward, or away from the vacuum cavity or tongue receiving cavity 1012 of the sheath 1010. The valve flap 1070 seats against an air extraction valve seal flange 1046 provided annually about an air extraction valve interior surface 1044 of the primary tubular structure of the air extraction valve 1040. The valve flap 1070 toggles between a closed configuration (FIG. 32), sealing an air extraction valve seal flange orifice 1047 and an opened configuration (FIG. 33), exposing the air extraction valve seal flange orifice 1047 for airflow therethrough.

A valve operational handle 1074 extends outward from the valve flap 1070. The valve flap 1070 and the valve operational handle 1074 are preferably located on opposite sides of the valve hinge pin 1072. The valve operational handle 1074 is preferably located externally to the primary tubular structure of the air extraction valve 1040, while the valve flap 1070 is located within an interior of the primary tubular structure of the air extraction valve 1040. The valve flap 1070 is shaped and sized to seal against the air extraction valve seal flange 1046 within the interior of the primary tubular structure of the air extraction valve 1040.

Details of an air extraction device 1050 in use are presented in FIGS. 32 and 33. The air extraction device 1050 includes a bulb air extraction tube 1060 extending outward from and in fluid communication with a bulb air extraction orifice 1054 of an air extraction bulb 1052. The air extraction bulb 1052 is fabricated of a pliant material, such as rubber, silicone, soft plastic, and the like. The pliant material enables compression of the air extraction bulb 1052 to expel air from within an interior thereof. Elastic properties of the pliant material enable the air extraction bulb 1052 to return to a natural shape. As the air extraction bulb 1052 returns from a collapsed condition to a natural shape, the air extraction bulb 1052 draws air through an interior of the bulb air extraction tube 1060, wherein the interior is defined by a bulb air extraction tube hollow interior 1061. The air drawn by the air extraction bulb 1052 removes air from the tongue receiving cavity 1012 generating a vacuum.

The illustrations in FIGS. 32 and 33 additionally present operation of the air extraction valve 1040. The bulb air extraction tube 1060 includes features to rotate the valve flap 1070, exposing the air passageway defined by the air extraction valve seal flange orifice 1047. An air extraction tube lead-in 1064 is formed at a distal end of the bulb air extraction tube hollow interior 1061. The air extraction tube lead-in 1064 can be a linear chamfer, a curved chamfer or of any other suitable shape. The air extraction tube lead-in 1064 extends between an initial opening having a diameter that is greater than a diameter of an air extraction valve exterior surface 1042 of the tongue bladder air extraction tube and a diameter of an air extraction tube seal surface 1062, wherein the air extraction tube seal surface 1062 is of a shape and size to create a snug, airtight seal about the air extraction valve exterior surface 1042 of the tongue bladder air extraction tube. An optional valve insertion stop seat 1066 can be formed between the air extraction tube seal surface 1062 and a balance of the bulb air extraction tube hollow interior 1061, wherein the valve insertion stop seat 1066 is a slight reduction in an interior diameter providing a stop placed against a distal end of the tongue bladder air extraction tube. The bulb air extraction tube hollow interior 1061 ensures against over insertion of the tongue bladder air extraction tube into the air extraction tube seal surface 1062 and could provide an additional seal between the tongue bladder air extraction tube and the bulb air extraction tube 1060. As the bulb air extraction tube 1060 is slideably placed over the tongue bladder air extraction tube, the surface of the bulb air extraction tube 1060 engages with the valve operational handle 1074. The relative motion between the tongue bladder air extraction tube and the air extraction valve 1040 pushes the valve operational handle 1074 forward, causing the valve assembly to pivot or rotate accordingly about the valve hinge pin 1072. The rotation pivots the valve flap 1070 away from the air extraction valve seal flange 1046, exposing the air extraction valve seal flange orifice 1047 defined by the air extraction valve seal flange 1046, and enabling air to pass therethrough. As the tongue bladder air extraction tube is slideably positioned onto the air extraction valve exterior surface 1042, the surfaces of the air extraction tube seal surface 1062 and the air extraction valve exterior surface 1042 contact one another forming an airtight seal. The user would compress the air extraction bulb 1052 either prior to the slideable insertion process or subsequent to the slideable insertion process. The compression forces air from the interior of the air extraction bulb 1052. This is in preparation for a step of drawing a vacuum from the tongue receiving cavity 1012. Once the air extraction device 1050 is secured to the air extraction valve 1040, with the valve flap 1070 in an open configuration, the user would release the applied compression, the air extraction bulb 1052 expands, returning to its original shape, and the expansion draws air from the tongue receiving cavity 1012, through an air extraction valve interior surface 1044 of the tongue bladder air extraction tube, through the air extraction valve seal flange orifice 1047, and into the bulb air extraction orifice 1054 creating a vacuum between the interior surface 1020 and the tongue surface 302. The vacuum generated retains the sheath 1010 in position on the tongue 300 of the user. The sheath interlock member 1030 would be assembled to a maxilla lip retention device 1300 (FIGS. 37 through 41) to draw the tongue 300 forward within the user's mouth to a desired position and retain the tongue 300 in the desired position. Details of this process will be described later herein.

The air extraction valve 1040 can include one or more features to aid in returning the valve flap 1070 to a sealed position. One such feature could be a biasing member, such as a cantilever spring. A second feature, presented in FIGS. 32 and 33, employs a magnetic force. One portion of a magnetically attracting pair of materials is a valve return control magnet 1079. The valve return control magnet 1079 is carried by the valve operational handle 1074. A second portion of a magnetically attracting pair of materials is a valve return control magnet 1069. The valve return control magnet 1069 is carried by a distal end of the bulb air extraction tube 1060. The magnetic attraction between the valve return control magnet 1069 and the valve return control magnet 1079 draws the valve operational handle 1074 away from the sheath 1010 as the bulb air extraction tube 1060 is separated from the tongue bladder air extraction tube, causing the valve operational handle 1074 to rotate, drawing the valve flap 1070 into a closed configuration against the air extraction valve seal flange 1046. The vacuum generated within the tongue receiving cavity 1012 retains the valve flap 1070 in a closed configuration. Although the exemplary embodiment employs a magnetic attraction, it is understood that any temporary coupling can be utilized, including an adhesive grip, a mechanical engagement such as a snap feature, and the like.

An air extraction valve clearance 1048 can be formed within the tongue bladder air extraction tube, wherein the air extraction valve clearance 1048 provides a clearance for the valve flap 1070 as shown in FIG. 33. Since the air extraction valve clearance 1048 is formed on a portion of the tongue bladder air extraction tube outside of the airtight boundary defined by the tongue receiving cavity 1012 and the air extraction valve 1040.

Figure 34:
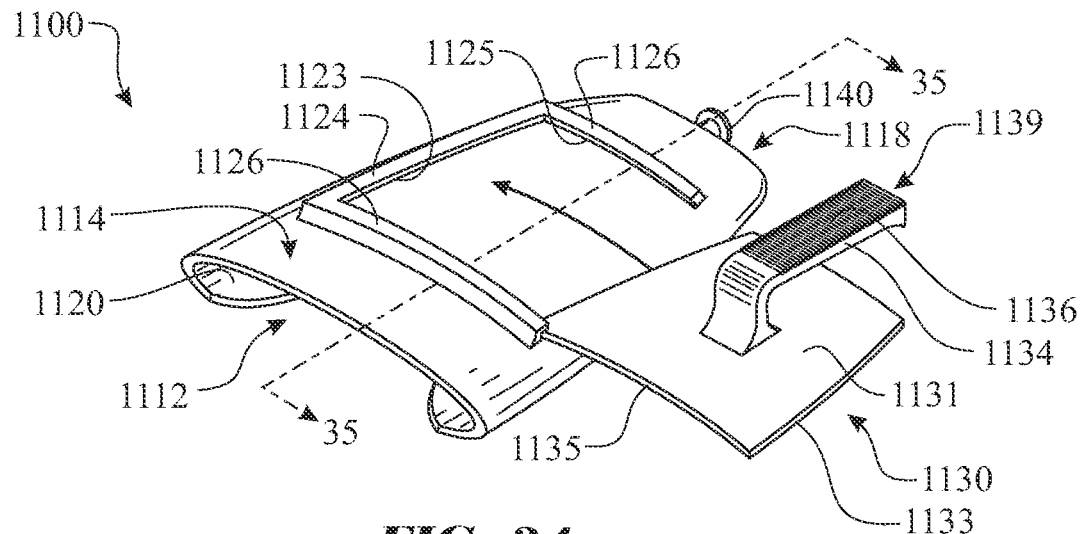
FIG. 34 presents an isometric, partially exploded assembly view of a dorsal side of a fifth exemplary tongue attachment member, wherein the fifth exemplary tongue attachment member is a variant of the third and fourth exemplary tongue attachment members introduced in FIGS. 22 and 29 respectively, wherein a sheath interlock member is slideably assembled to a channel formed in the dorsal side of the tongue attachment member body.
Figure 35:
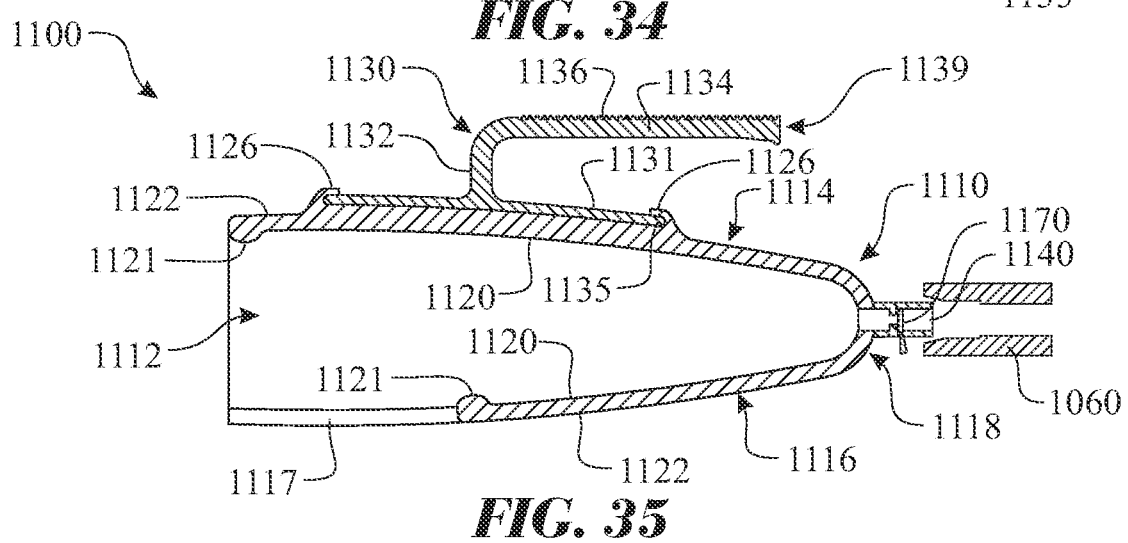
FIG. 35 presents a sectioned view of the fifth tongue attachment member taken along section 35-35 of FIG. 34, wherein the illustration presents a bulb air extraction tube of an air extraction device prior to insertion onto an air extraction valve.
Figure 36:
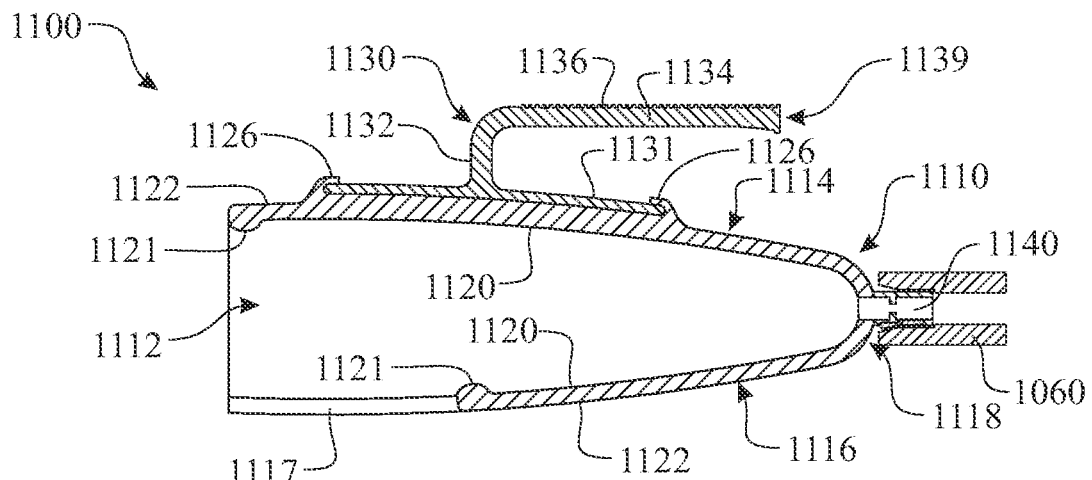
FIG. 36 presents a sectioned view of the fifth tongue attachment member taken along section 35-35 of FIG. 34, wherein the illustration presents the bulb air extraction tube of the air extraction device following insertion onto the air extraction valve.

In the tongue embracing member 1000, the sheath interlock member 1030 is assembled to the sheath 1010 by an overmolding process. The sheath interlock member 1030 can be assembled to the sheath 1010 using any suitable method. A tongue embracing member 1100 presents an alternative configuration for assembling a sheath interlock member 1130 to a sheath 1110, as shown in FIGS. 34 through 36. The tongue embracing member 1100 is similar to the tongue embracing member 1000, whereby the distinguishing features are described herein. Like features of the tongue embracing member 1100 and tongue embracing member 1000 are numbered the same except preceded by the numeral '11'. A sheath interlock member base 1131 of the sheath interlock member 1130 is shaped to contour to a surface associated with a dorsal side 1114 of a sheath 1110 of the tongue embracing member 1100. The sheath interlock member base 1131 is defined by a peripheral boundary, more specifically a pair of sheath interlock member base longitudinal edges 1133 and a pair of sheath interlock member base lateral edges 1135. An arrangement of channels 1124, 1126 is formed on the portion of an exterior surface 1122 associated with the dorsal side 1114 of the sheath 1110, wherein the arrangement of channels 1124, 1126 are shaped and sized to receive and retain the sheath interlock member base 1131 on the exterior surface 1122 of the sheath 1110. The arrangement of channels 1124, 1126 includes a pair of lateral channels 1126 transversely arranged upon the exterior surface 1122 and a longitudinal channel 1124 extending between like ends of the pair of lateral channel 1126, wherein the first channel segment 1126, the third channel segment 1124 and the second channel segment 1126 collectively form a "U" shaped channel. Each lateral channel 1126 defines a lateral channel groove 1125. The longitudinal channel 1124 defines a longitudinal channel groove 1123. The sheath interlock member base lateral edge 1135 slides into the lateral channel groove 1125. The lateral channel 1126 constrains the sheath interlock member 1130 against any longitudinal movement. The sheath interlock member base 1131 slides into the longitudinal channel groove 1123. The longitudinal channel 1124 provides an insertion stop in a transverse direction to ensure proper alignment between an interlock member engagement segment 1134 and a longitudinal centerline of the sheath 1110. This configuration enables low cost manufacturing of the tongue embracing member 1100 compared to the costs of a two part overmolding process by avoiding a step of inserting the sheath interlock member 1030 into the mold cavity used for fabricating the sheath 1010 and the additional machine costs for the additional movements of mold sections to accommodate the inserted sheath interlock member 1030.

As previously described, the tongue embracing member 1100 is temporarily secured to the individual's tongue 300 by created a vacuum between the interior surface 1120 and the tongue surface 302. The tongue embracing member 1100 introduces a sheath tongue sealing ridge 1121, wherein the preferred design includes a sheath tongue sealing ridge 1121 circumscribing a peripheral edge of the interior surface 1120. The sheath tongue sealing ridge 1121 acts as a gasket, enhancing the seal between the interior surface 1120 and the tongue surface 302 when subjected to the vacuum.

Figure 37:
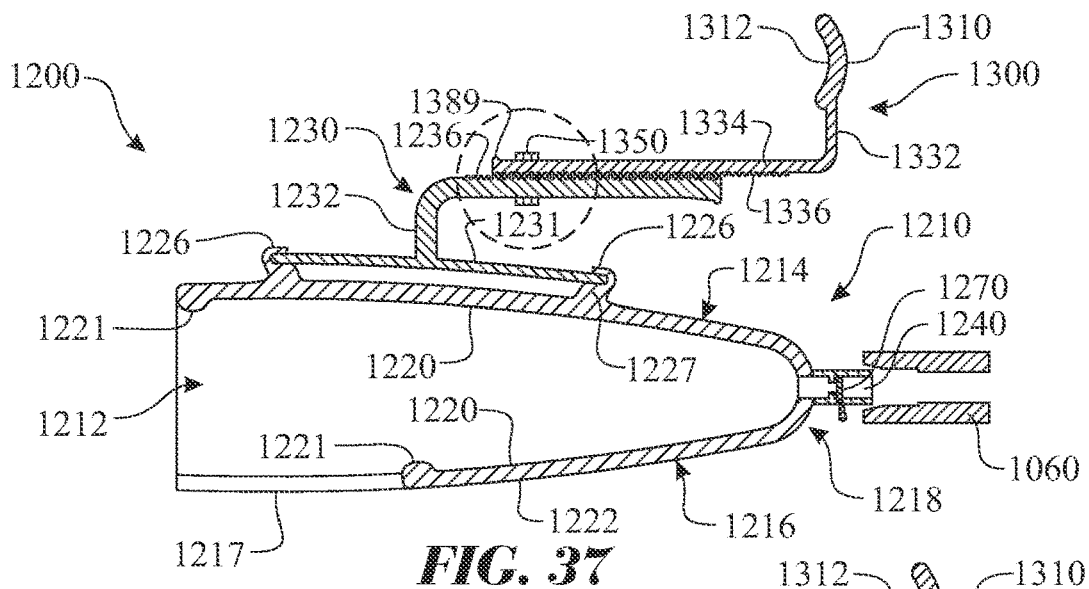
FIG. 37 presents a sectioned view of the sixth tongue attachment member, wherein the sixth exemplary tongue attachment member is a variant of the fifth exemplary tongue attachment member as shown in FIG. 35, wherein a sheath interlock member is slideably assembled to a channel formed having an arrangement spatially above the dorsal side of the tongue attachment member body, the valve shown in a closed configuration and a maxilla lip retention device shown in a slideably adjustable, retracted configuration.
Figure 38:
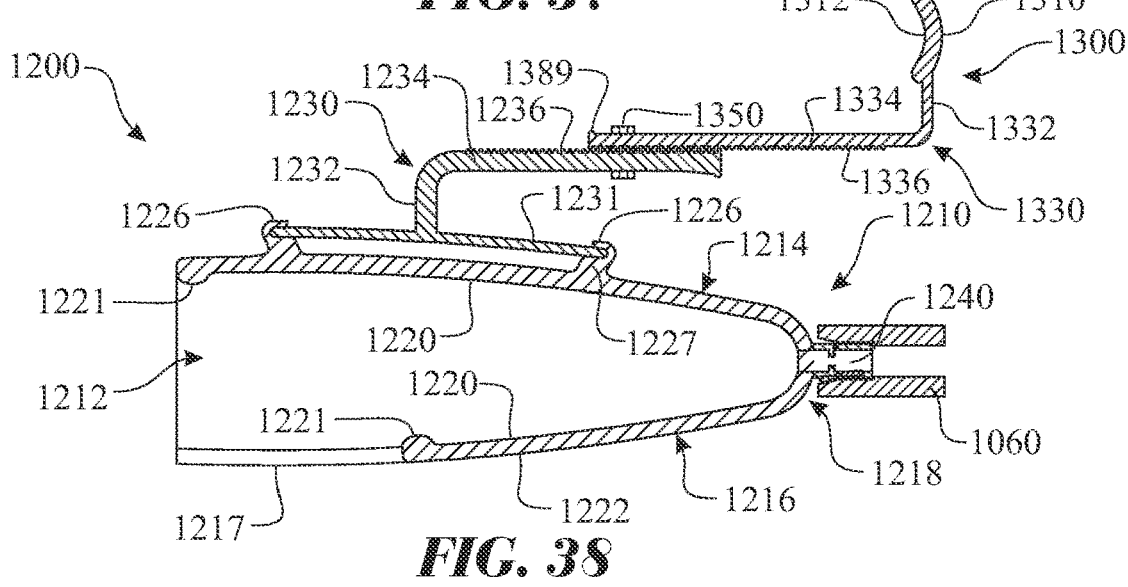
FIG. 38 presents a sectioned view of the sixth tongue attachment member, the illustration being similar to the illustration presented in FIG. 37, wherein the valve shown in an open configuration and a maxilla lip retention device shown in a slideably adjustable, extended configuration.
Figure 39:
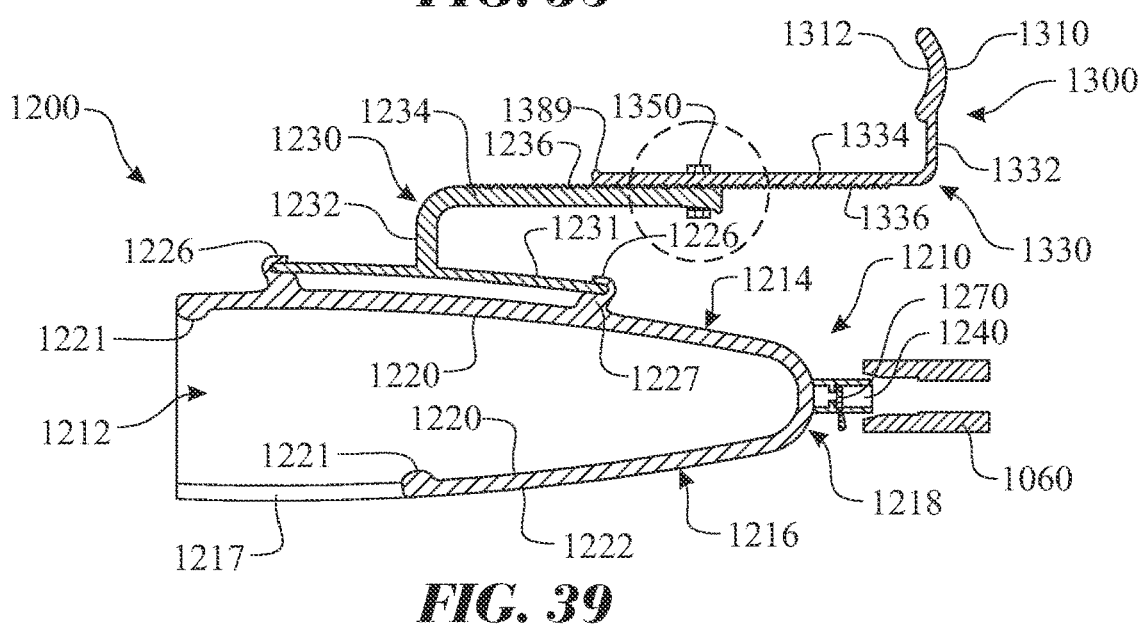
FIG. 39 presents a sectioned view of the sixth tongue attachment member, the illustration being similar to the illustration presented in FIGS. 37 and 38, wherein the valve shown in an closed configuration and a maxilla lip retention device shown in a secured or locked configuration.

In the tongue embracing member 1100, the sheath interlock member base 1131 is assembled to the sheath 1110 by sliding the sheath interlock member base 1131 into recessions 1123, 1125 formed by channels 1124, 1126. The channel configuration positions a lower surface of the sheath interlock member base 1131 against the exterior surface 1122 of the sheath 1110. In certain circumstance, this arrangement can potentially cause the interior surface 1120 to dislodge from the tongue surface 302 of the tongue 300, resulting in a breach of the vacuum therein. A tongue embracing member 1200 presents an alternative channel configuration to accommodate this potential risk by including a channel riser feature 1227, as shown in FIGS. 37 through 39. The tongue embracing member 1200 is similar to the tongue embracing member 1100, whereby the distinguishing feature is the channel riser feature 1227. Like features of the tongue embracing member 1200 and tongue embracing member 1100 are numbered the same except preceded by the numeral '12'. The channel riser feature 1227 introduces a space between the exterior surface 1222 of a sheath 1210 and a lower surface of a sheath interlock member base 1231 of a sheath interlock member 1230. Properties of the channel riser feature 1227 introduces flexure thereof, reducing transfer of any torsional forces generated by a motion of the maxilla lip retention device 1300 translating through the sheath interlock member 1230 onto the sheath 1210. This reduction in transfer of any generated torsional forces reduces any potential risk of breaching the vacuum forces between the interior surface 1220 and the tongue surface 302 of the tongue 300.

Figure 40:
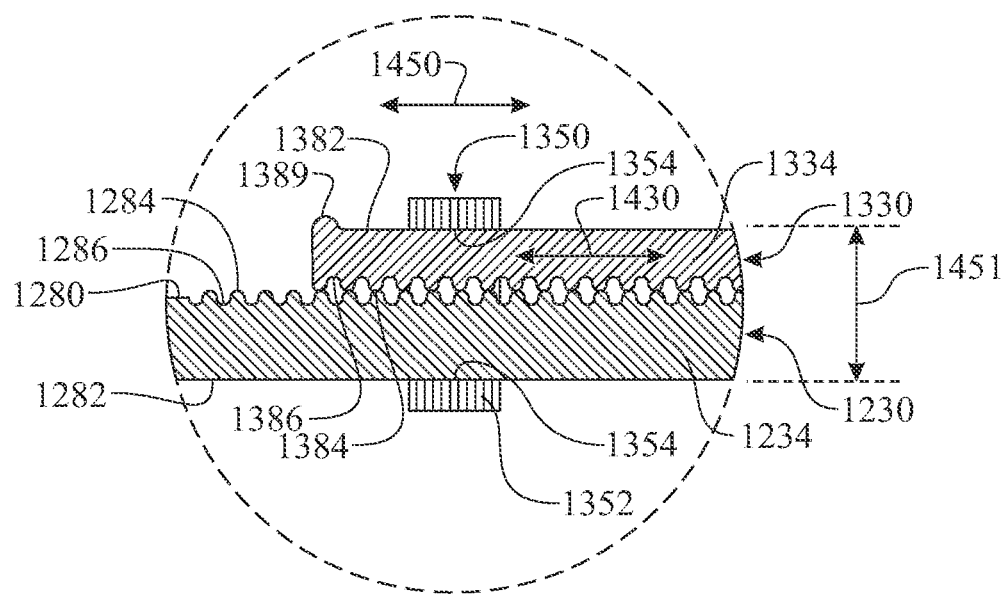
FIG. 40 presents a magnified sectioned view detailing a positioning control system used to toggle between an adjustable configuration and a locked configuration between a sheath interlock member arm of the sheath interlock member and a maxilla lip retention positioning arm of a maxilla lip retention device, the illustration presenting the interlocking assembly in a slideably adjustable configuration.
Figure 41:
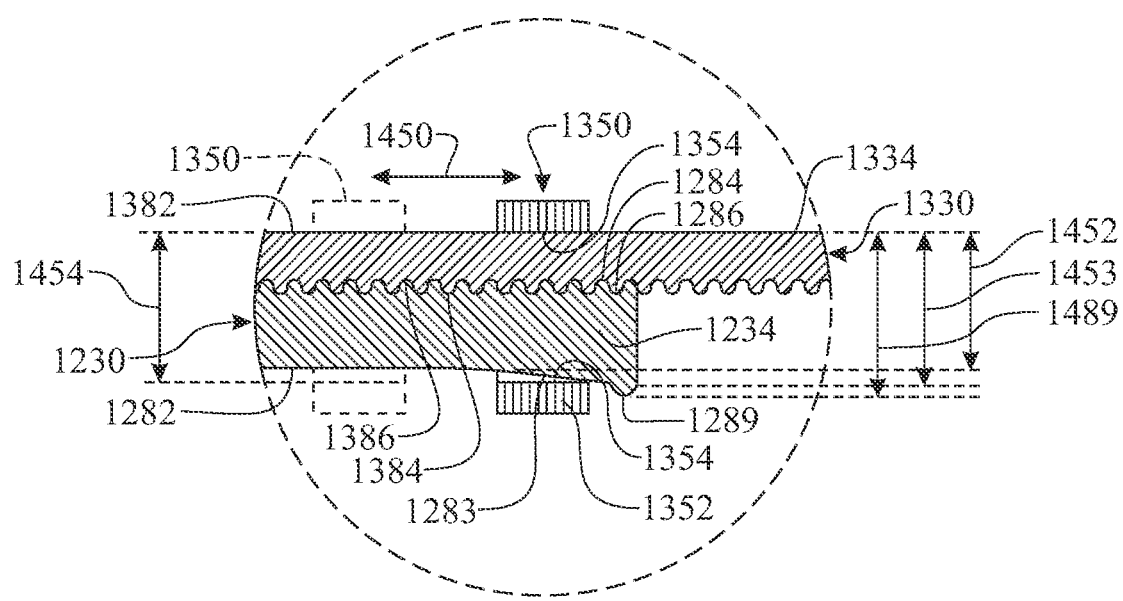
FIG. 41 presents a magnified sectioned view introduced in FIG. 40, the illustration presenting the interlocking assembly in a locked or motion restricted configuration.
Figure 42:
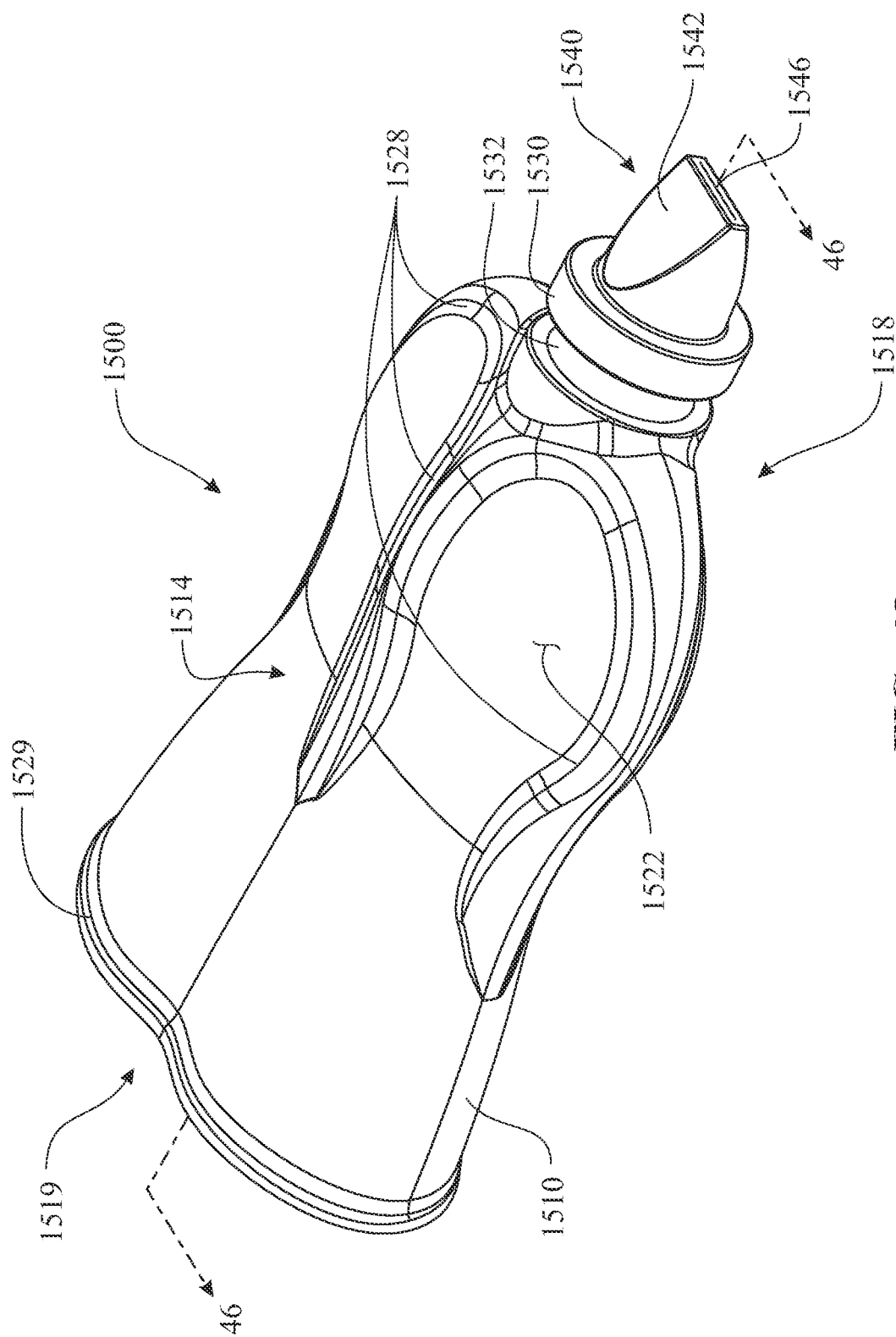
FIG. 42 presents an isometric top view of another exemplary tongue attachment subassembly.
Figure 43:
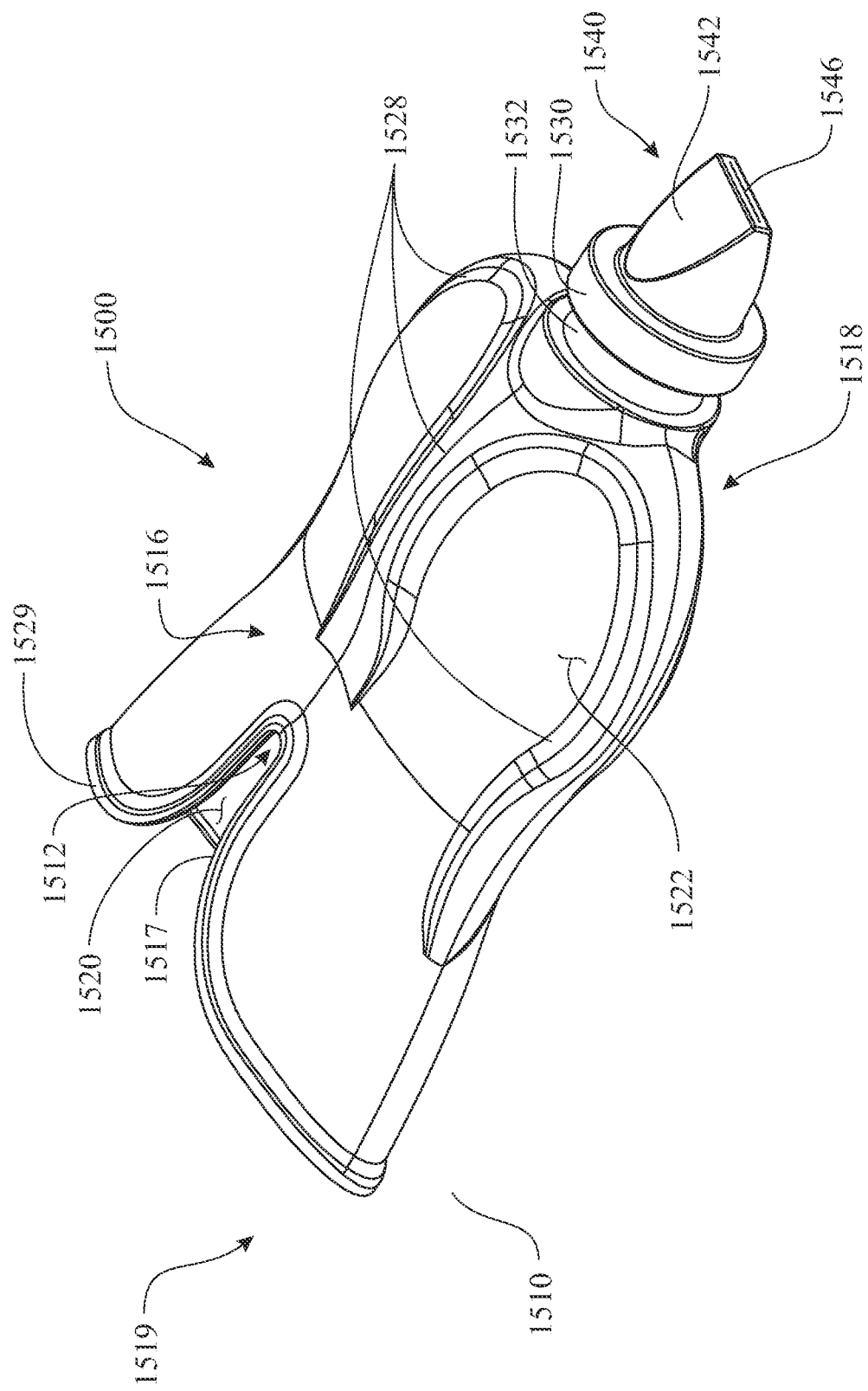
FIG. 43 presents an isometric bottom view the exemplary tongue attachment subassembly originally introduced in FIG. 42.

The tongue embracing member 1200 is designed to draw the tongue 300 of the user forward. This positioning retention system can be employed for sleep apnea, during a surgical procedure to ensure the patient's tongue 300 does not become lodge in the patient's throat. The positioning retention system utilizes a position adjusting system created by features of the sheath interlock member 1230, features of the maxilla lip retention positioning arm 1330, and a position retaining member 1350. The interlock member positioning feature 1236 of the interlock member engagement segment 1234 can be of any suitable grip enhancing feature. This can include a friction enhancing surface (adding texture, adding a material having a higher coefficient of friction, and the like), forming the surface of the interlock member engagement segment 1234 into a desired shape (such as a series of interlock member locking surface projection (peak) 1284 and interlock member locking surface recession (valley) 1286 as illustrated in FIGS. 40 and 41) and the like. In the exemplary embodiment, the interlock member positioning feature 1236 includes a series of interlock member locking surface projection (peak) 1284 and interlock member locking surface recession (valley) 1286. The interlock member locking surface projections (peaks) 1284 and interlock member locking surface recessions (valleys) 1286 can be formed in any design to matingly engage with like positioning arm locking surface projections (peaks) 1384 and positioning arm locking surface recessions (valleys) 1386 formed on a mating surface of the positioning arm lateral segment 1334. In the exemplary embodiment, the interlock member locking surface projections (peaks) 1284 and interlock member locking surface recessions (valleys) 1286 and the mating positioning arm locking surface projections (peaks) 1384 and positioning arm locking surface recessions (valleys) 1386 are linear in formation and equally spaced arranged. The interlock member locking surface projections (peaks) 1284 and interlock member locking surface recessions (valleys) 1286 and the mating positioning arm locking surface projections (peaks) 1384 and positioning arm locking surface recessions (valleys) 1386 can be formed at any angle respective to a longitudinal axis of the respective interlock member engagement segment 1234, positioning arm lateral segment 1334. In the exemplary embodiment, the interlock member locking surface projections (peaks) 1284 and interlock member locking surface recessions (valleys) 1286 and the mating positioning arm locking surface projections (peaks) 1384 and positioning arm locking surface recessions (valleys) 1386 are perpendicular to a longitudinal axis of the respective interlock member engagement segment 1234, positioning arm lateral segment 1334. More specifically, the interlock member locking surface projections (peaks) 1284 and interlock member locking surface recessions (valleys) 1286 and the mating positioning arm locking surface projections (peaks) 1384 and positioning arm locking surface recessions (valleys) 1386 are linear, oriented substantially parallel to one another, and equally spaced arranged.

Although the interlock member locking surface projections (peaks) 1284 and interlock member locking surface recessions (valleys) 1286 and the mating positioning arm locking surface projections (peaks) 1384 and positioning arm locking surface recessions (valleys) 1386 are shown as having a linear arrangement, it is understood that the interlock member locking surface projections (peaks) 1284 and interlock member locking surface recessions (valleys) 1286 and the mating positioning arm locking surface projections (peaks) 1384 and positioning arm locking surface recessions (valleys) 1386 can be of any suitable design, including a cross hatching, a series of bosses and embosses, a series of dimples and recessions, and the like.

The interlock member engagement segment 1234 and the associated positioning arm lateral segment 1334 are assembled together orienting mating surfaces contacting one another, as best shown in FIGS. 40 and 41.

The position retaining member 1350 at least partially circumscribes an external periphery defined by an assembly of the sheath interlock member arm 1234 and the maxilla lip retention subassembly segment 1334. The position retaining member 1350 includes a position retaining member body 1352 preferably shaped as a tubular member. The position retaining member 1350 can be formed having a tubular rectangle shape, a tubular oblong shape, an elliptical shape, and the like, wherein the preferred shape would mimic the cross sectional shape of the assembly of the sheath interlock member arm 1234 and the maxilla lip retention subassembly segment 1334. It is understood that the position retaining member 1350 can be fabricated in any suitable cross sectional shape, including a "C" channel shape, a "U" channel shape, any tubular shape, an "I" beam shape, or having any other suitable cross sectional design.

An interior distance 1454 spanning between an interior transverse or upper surface 1354 and an interior opposite transverse or lower surface 1354 of the position retaining member 1350 is sized enabling a sliding motion between the sheath interlock member arm 1234 and the maxilla lip retention subassembly segment 1334 when positioned at a location of the assembly having a narrow thickness (illustrated as the position retaining member 1350 presented in broken lines on FIG. 41) and restraining any sliding motion between the sheath interlock member arm and the maxilla lip retention subassembly arm when positioned at a location of the assembly having a wider thickness (illustrated as the position retaining member 1350 presented in solid lines on FIG. 41).

The position retaining member internal span 1454 would be of a dimension enabling separation between the interlock member engagement segment 1234 and the positioning arm lateral segment 1334, thus disengaging the interlock member positioning feature 1236 (the interlock member locking surface projection (peak) 1284 and the interlock member locking surface recession (valley) 1286) and the interlock member positioning feature 1336 (the positioning arm locking surface projection (peak) 1384 and the positioning arm locking surface recession (valley) 1386) from one another, enabling a sliding motion 1430. The interlock member engagement segment 1234 and the positioning arm lateral segment 1334 separates sufficiently enabling the interlock member locking surface projection (peak) 1284 and the positioning arm locking surface projection (peak) 1384 to slide over one another. The minimum dimension is identified as a teeth disengaged configuration assembly thickness 1451 (the distance between the interlock member position retaining member support surface 1282 and the position retaining member support surface 1382 when the interlock member engagement segment 1234 and the positioning arm lateral segment 1334 are separated from one another in a positionable configuration), as shown in FIG. 40. The position retaining member internal span 1454 must be at least equal to or greater than the teeth disengaged configuration assembly thickness 1451.

The sliding motion 1430 enables positioning of the interlock member engagement segment 1234 and the positioning arm lateral segment 1334 relative to one another. This positioning properly locates the sheath 1210, thus properly positioning and retaining the tongue 300 of the user as desired. It is noted that the design of the interlock member locking surface projection (peak) 1284 and the interlock member locking surface recession (valley) 1286 as well as the positioning arm locking surface projection (peak) 1384 and the positioning arm locking surface recession (valley) 1386 define a pitch, or the limitations for the change in a locked position. The finer the pitch (smaller the spatial gap between like features), the greater the adjustability of the position between the interlock member engagement segment 1234 and the positioning arm lateral segment 1334.

Once the interlock member engagement segment 1234 and the positioning arm lateral segment 1334 are located in a desired position respective to one another, they are brought together, seating the interlock member locking surface projection (peak) 1284 into the respective positioning arm locking surface recession (valley) 1386 and similarly, seating the positioning arm locking surface projection (peak) 1384 into the respective interlock member locking surface recession (valley) 1286. This reduces the dimension between the interlock member position retaining member support surface 1282 and the position retaining member support surface 1382 from the teeth disengaged configuration assembly thickness 1451 to a teeth engaged configuration assembly thickness 1452 (the distance between the interlock member position retaining member support surface 1282 and the position retaining member support surface 1382 when the interlock member engagement segment 1234 and the positioning arm lateral segment 1334 are brought together in a locked configuration), introduced in FIG. 41. Once the interlock member engagement segment 1234 and the positioning arm lateral segment 1334 are brought together, seating the interlock member locking surface projection (peak) 1284 into the respective positioning arm locking surface recession (valley) 1386 and similarly, seating the positioning arm locking surface projection (peak) 1384 into the respective interlock member locking surface recession (valley) 1286, the position retaining member 1350 is repositioned in accordance with a position retaining member sliding motion 1450 from the adjustment position (shown in broken line) to a locked or retention position (shown in solid line). The position retaining member 1350 is moved into a region of the sheath interlock member 1230 having an interlock member thickness wedge shaped segment 1283. The interlock member thickness wedge shaped segment 1283 is formed along a segment of at least one of the sheath interlock member arm 1234 and the maxilla lip retention subassembly segment 1334. The interlock member thickness wedge shaped segment 1283 is formed as a changing thickness of the sheath interlock member arm 1234 (as shown) and/or the maxilla lip retention subassembly segment 1334 defining a tapering distal or outer surface. The interlock member thickness wedge shaped segment 1283 creates a wedge, increasing a dimension between opposite outer surfaces 1382, 1283, (referenced as a teeth engaged configuration assembly wedge section thickness 1453), securing the position retaining member 1350 in position. The position retaining member 1350 retains engagement between the interlock member positioning feature 1236 and the interlock member positioning feature 1336, thus retaining the positional relationship between the interlock member engagement segment 1234 and the positioning arm lateral segment 1334. A position retaining member retention feature 1289 can be formed at a distal end of the interlock member engagement segment 1234. The introduction of the position retaining member retention feature 1289 defines a position retaining member retention thickness 1489. The position retaining member retention thickness 1489 is greater than the position retaining member internal span 1454, thus keeping the position retaining member 1350 from becoming separated from the assembly. Similarly, a position retaining member retention feature 1389 can be formed at a distal end of the positioning arm lateral segment 1334. The position retaining member retention feature 1389 provides the same function as the position retaining member retention feature 1289, but at an opposite end of the assembly, thus ensuring against separation of the position retaining member 1350 from the assembly.

A tongue attachment subassembly 1500, illustrated in FIGS. 42, 43, and 46 through 48, is yet another variant of the tongue attachment subassembly 100. The exemplary tongue attachment subassembly 1500 is another variant adapted for treatment of sleep apnea. The tongue attachment subassembly 1500 and the tongue attachment subassembly 100 include a number of like elements. Like elements of the tongue attachment subassembly 1500 and the tongue attachment subassembly 100 are numbered the same, preceded by the numeral "15". Orientation of sides of the tongue attachment subassembly 1500 is referenced by a dorsal side 1514 and a ventral side 1516. Orientation of ends of the tongue attachment subassembly 1500 is referenced by a sheath distal end 1518 and a sheath proximal end 1519.

Deviations between the tongue attachment subassembly 1500 and the tongue attachment subassembly 100 are identified herein. A sheath shape retention feature 1528 is formed extending rearward from the sheath distal end 1518 of a sheath 1510. The sheath shape retention feature 1528 can be of any suitable size and shape to retain a structural and shape integrity during use. The sheath shape retention feature 1528 is preferably fabricated of the same material as the sheath 1510. However, the sheath shape retention feature 1528 can be fabricated of a different material compared to the sheath 1510. Similarly, a sheath proximal edge reinforcement feature 1529 is provided about the proximal edge of the sheath 1510. The sheath proximal edge reinforcement feature 1529 increases the reliability of the sheath 1510 as well as a vacuum seal of a tongue receiving cavity 1512 when the tongue attachment subassembly 1500 is placed upon the patient's tongue 300.

An air extraction valve 1540 is formed at a distal end of a tubular element 1543 extending forward from a distal end 1518 of the sheath 1510. The air extraction valve 1540 includes a duckbill valve 1542. A duck valve slit 1546 is cut through the end of the duckbill valve 1542 providing the resealing vacuum passageway. In use, the outer edges of the duckbill valve 1542 are compressed towards one another, causing the planar sections to arch, opening the duck valve slit 1546. A vacuum is applied, drawing air from a volume between the individual's tongue 300 and the tongue engagement surface 1520. The sheath proximal edge reinforcement feature 1529 provides a seal against a proximal end of the individual's tongue 300. Upon removal of the vacuum draw, the remaining vacuum would draw the planar segments of the duckbill valve 1542 towards one another, sealing the duck valve slit 1546.

Figure 44:
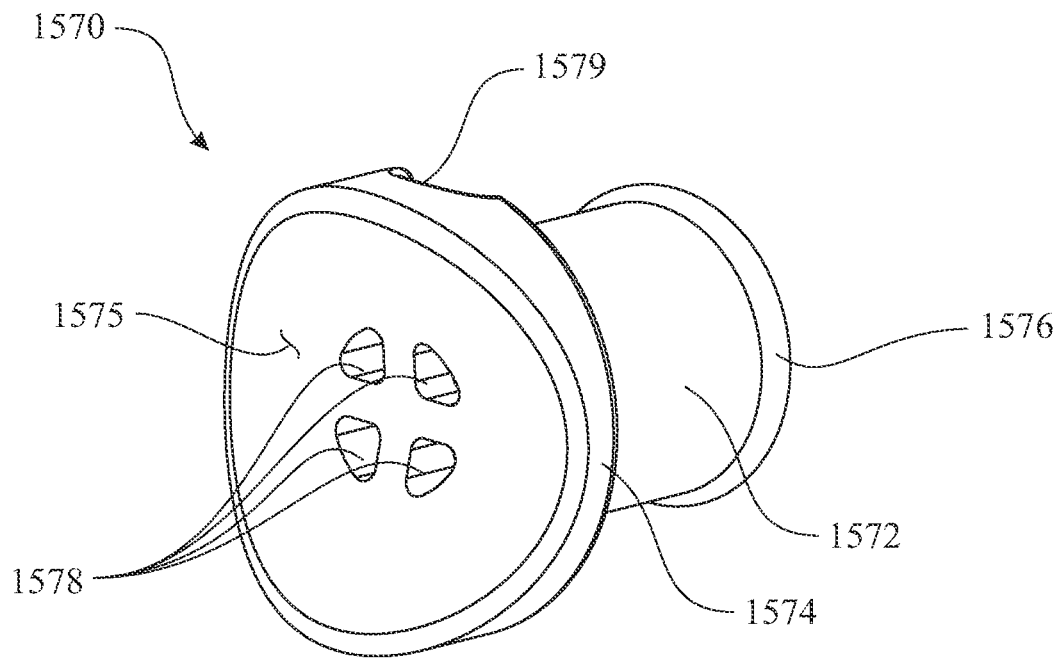
FIG. 44 presents an isometric proximal end view of an exemplary tongue protection insert.
Figure 45:
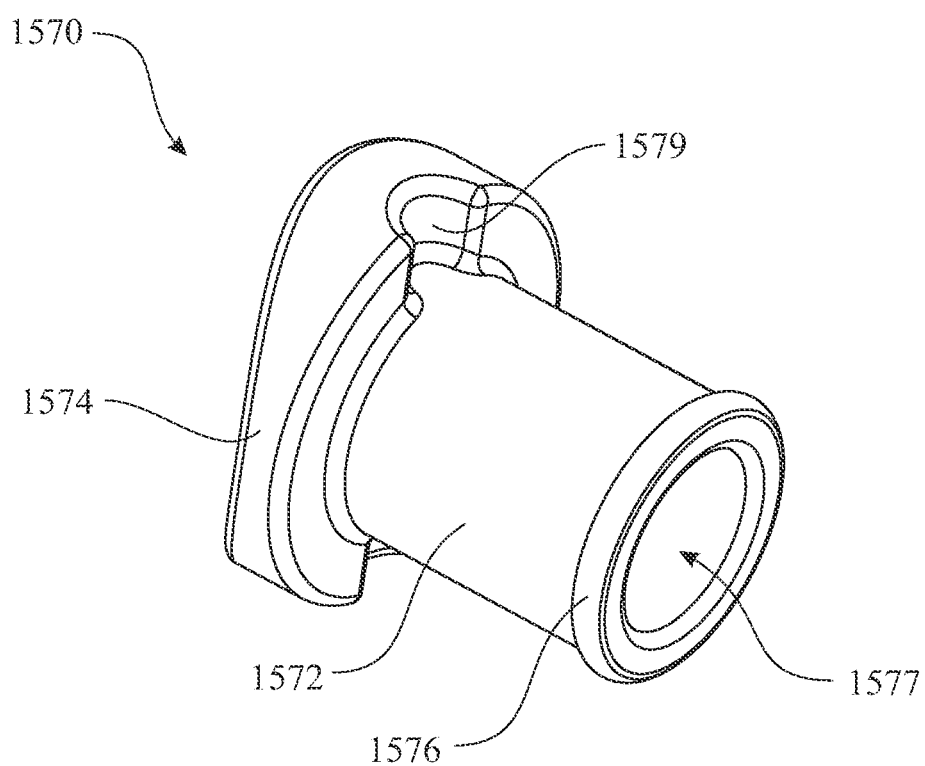
FIG. 45 presents an isometric distal end view of the tongue protection insert originally introduced in FIG. 43.

A tongue protection insert 1570, illustrated in FIGS. 44 and 45, can be included providing a feature which protects the tongue during the vacuum drawing process. The exemplary tongue protection insert 1570 includes a tongue protection insert interior or proximal flange 1574 formed at a proximal end of a tongue protection insert tubular body 1572. The tongue protection insert interior or proximal flange 1574 is shaped having a tongue protection insert interior flange arched surface 1575. A tongue protection insert orientation feature 1579 can be included in any portion of the tongue protection insert 1570 to provide guidance for an orientation of the tongue protection insert 1570 during installation of the tongue protection insert 1570 into the sheath 1510. The exemplary tongue protection insert 1570 includes a pair of tongue protection insert orientation features 1579, each tongue protection insert orientation feature 1579 formed at semicircular quadrants of the tongue protection insert interior or proximal flange 1574. A tongue protection insert distal flange 1576 can be formed at a distal end of the tongue protection insert tubular body 1572. The tongue protection insert interior or proximal flange 1574 and the tongue protection insert distal flange 1576 provides seals between the tongue protection insert 1570 and the valve passageway 1543. Vacuum draw is provided through a tongue protection insert tubular body vacuum passageway 1577 and each of a series of tongue protection insert interior flange vacuum orifice 1578. The series of tongue protection insert interior flange vacuum orifice 1578 segment the vacuum draw into smaller cross sectional areas to reduce the draw onto the individual's tongue 300.

The tongue protection insert 1570 can be inserted into a valve passageway 1543 formed through the sheath distal end 1518 of the sheath 1510. Orientation of the tongue protection insert 1570 can be provided by seating the tongue protection insert orientation feature 1579 against a tongue insert orientation feature 1539 provided within a flange receiving recess formed within the tongue engagement surface 1520.

An accessory attachment feature can be provided at a sheath distal end 1518 of the sheath 1510. The exemplary accessory attachment feature includes an interlock coupling groove 1532 located between an interlock coupling flange 1530 and a distal end of the sheath 1510.

The tongue attachment subassembly 1500 is preferably fabricated of a uniform material and of a unitary construction. The duck valve slit 1546 would be formed using a secondary slitting process.

Figure 47:
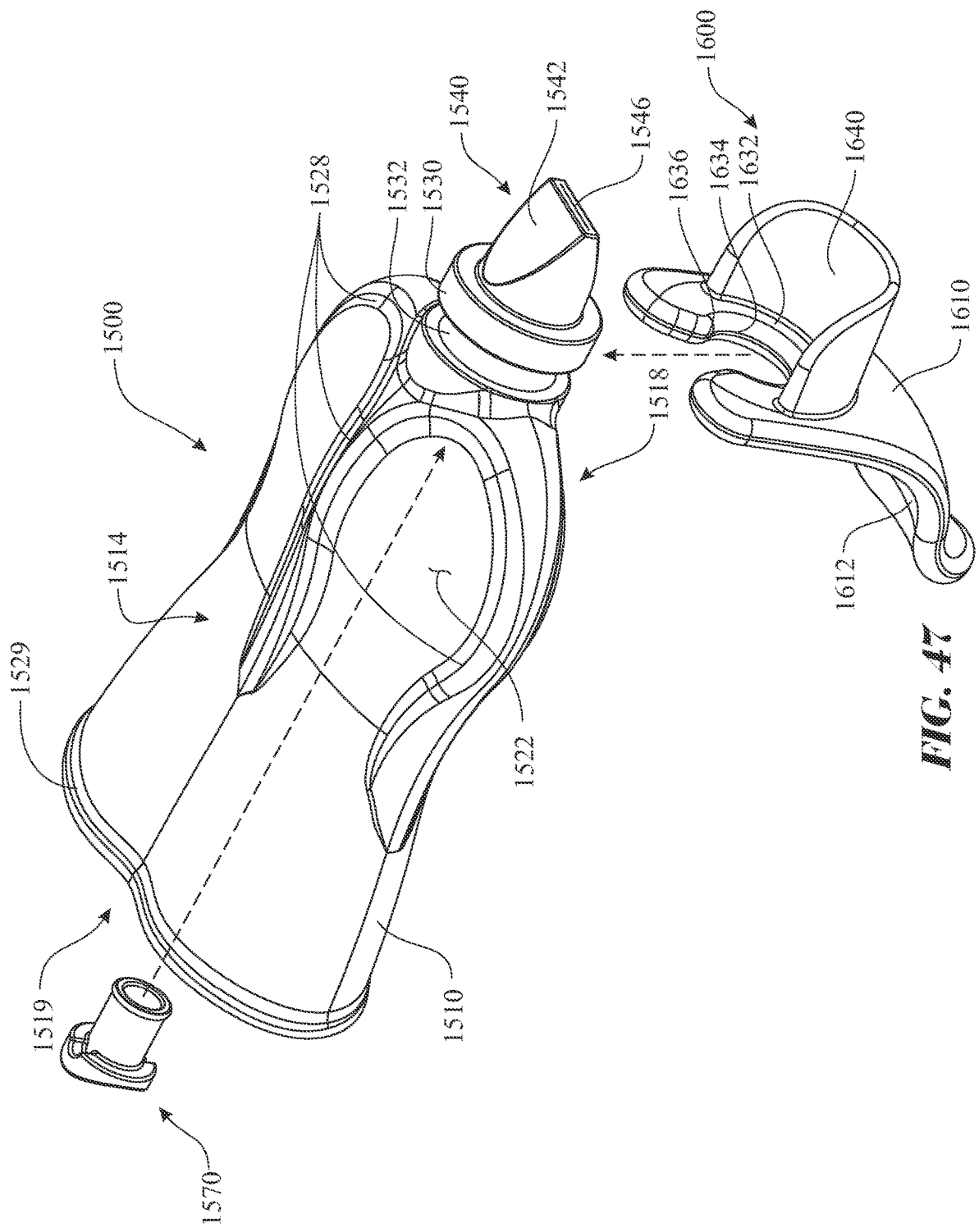
FIG. 47 presents an exploded isometric top view an assembly using the exemplary tongue attachment subassembly originally introduced in FIG. 42 in conjunction with a tongue position retention bracket for treating sleep apnea.
Figure 48:
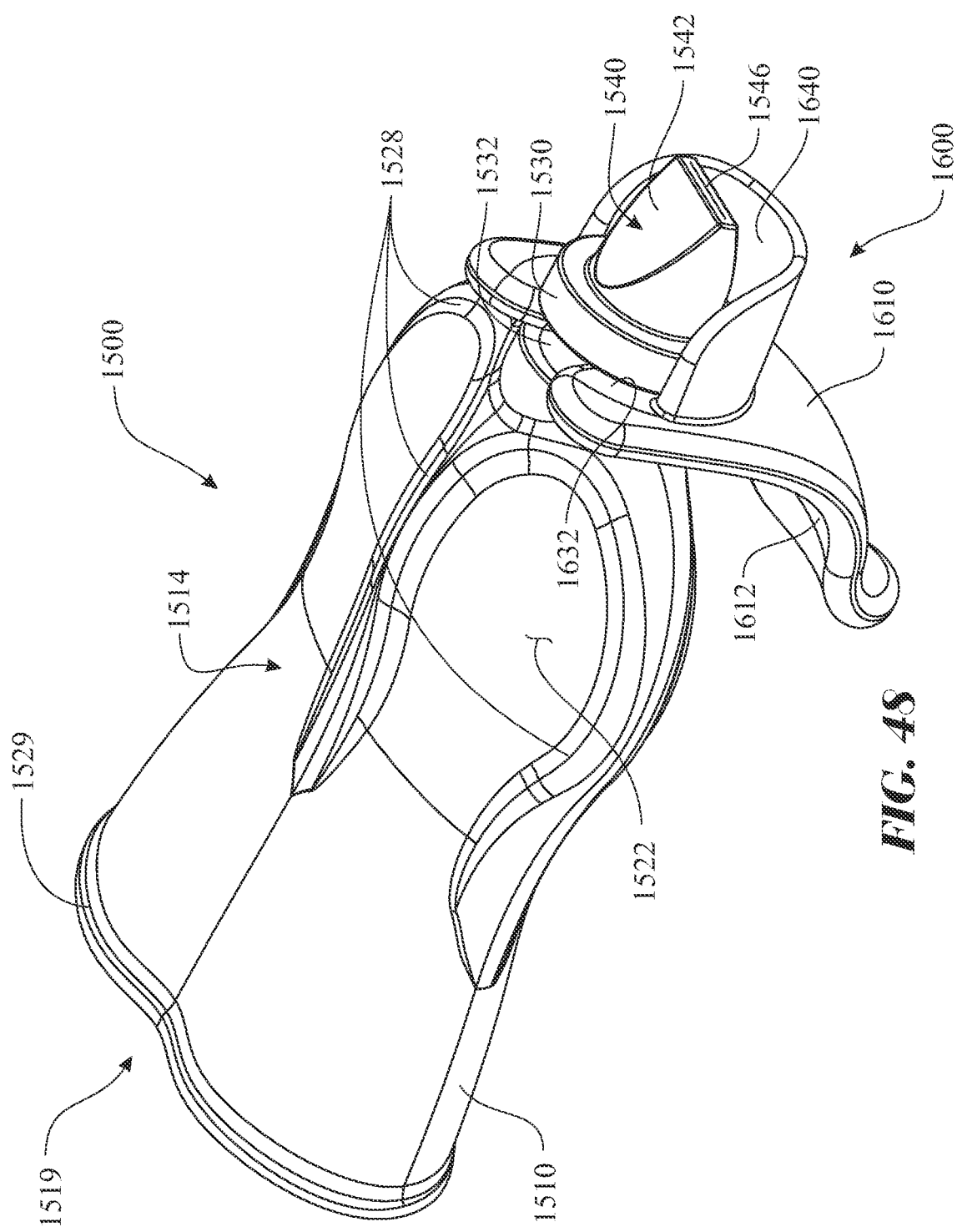
FIG. 48 presents an isometric top assembly view the components originally introduced in an exploded configuration in FIG. 47 for treating sleep apnea.
Figure 49:
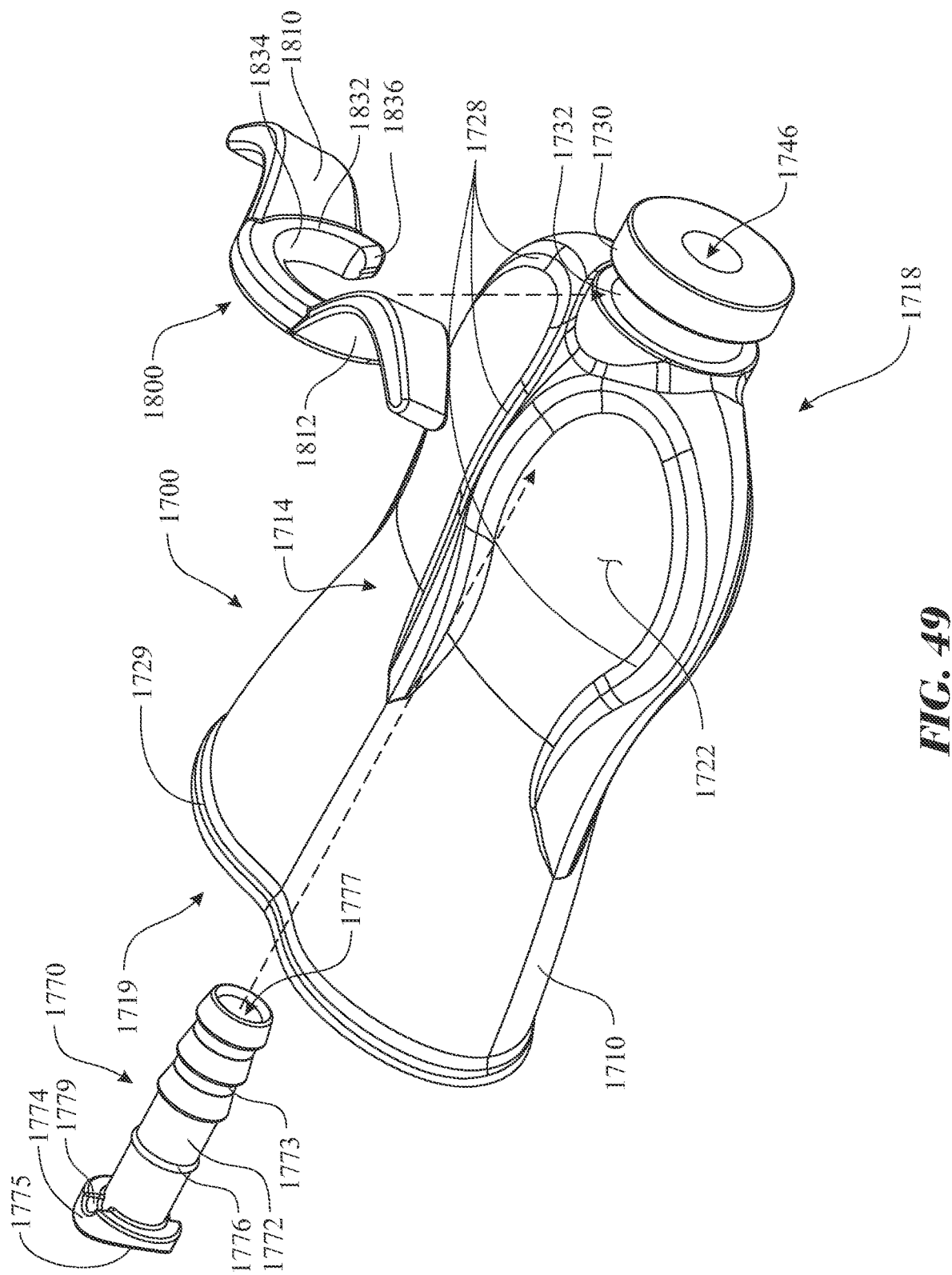
FIG. 49 presents an exploded isometric top view an assembly using a modified variant if the exemplary tongue attachment subassembly originally introduced in FIG. 42 in conjunction with a gas management mask retention bracket forming an gas management mask application system.
Figure 50:
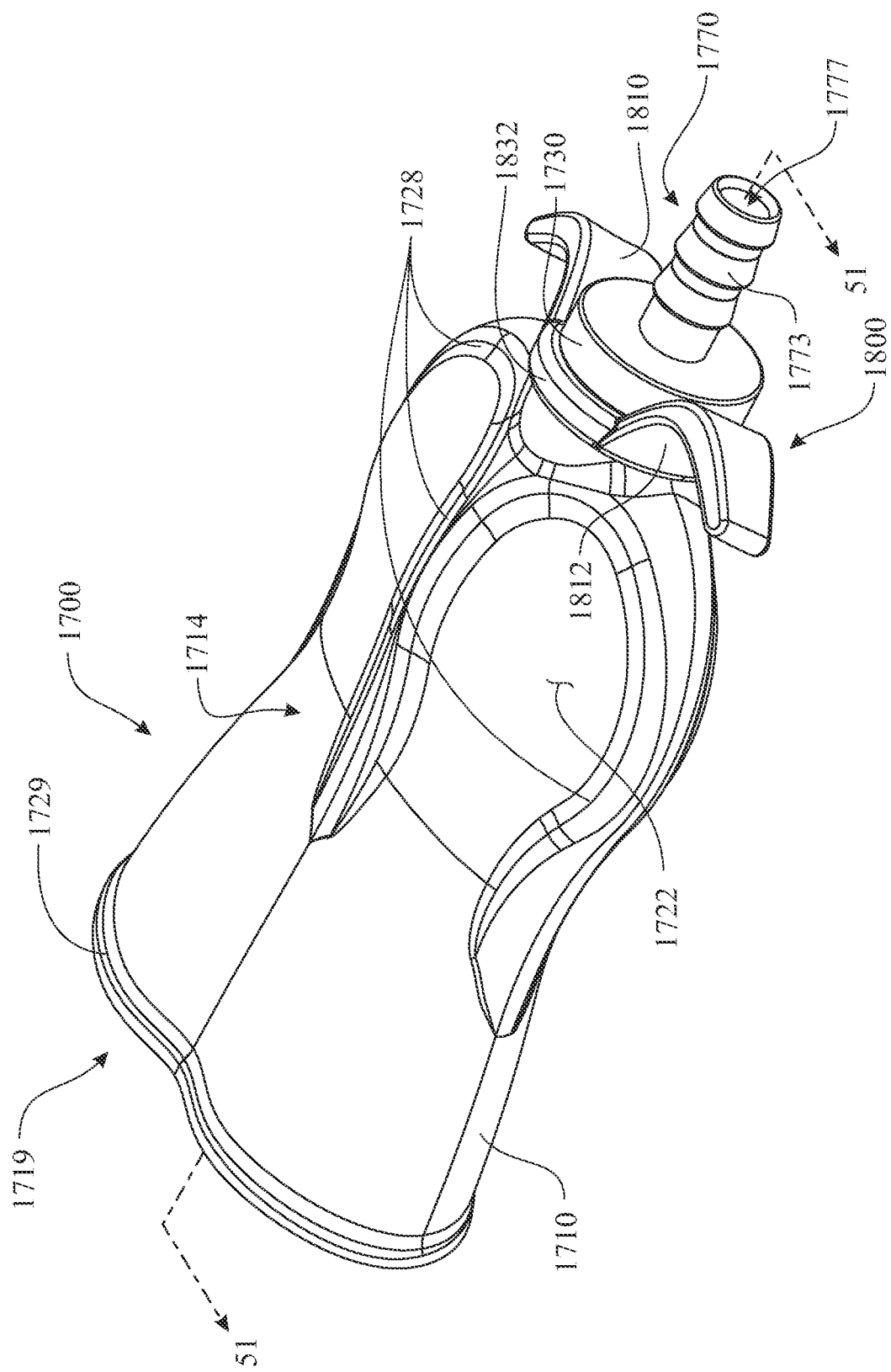
FIG. 50 presents an isometric top assembly view of the components forming the gas management mask application system originally introduced in an exploded configuration in FIG. 49.

The tongue attachment subassembly 1500 can be combined with a tongue position retention bracket 1600 to create a sleep apnea treatment system, as illustrated in FIGS. 47 and 48.

The tongue position retention bracket 1600 includes a tongue position retention bracket assembly clip 1632 formed within a tongue position retention bracket body 1610. A tongue position retention bracket assembly clip interior surface 1634 is formed as a C-shaped groove engaging surface of the tongue position retention bracket assembly clip 1632. The tongue position retention bracket assembly clip interior surface 1634 circumscribes a circumference of greater than 180 degrees about the tongue position retention bracket assembly clip 1632. A tongue position retention bracket assembly clip retention feature 1636 is formed at each end of the tongue position retention bracket assembly clip interior surface 1634. The pair of tongue position retention bracket assembly clip retention feature 1636 is designed to retain the tongue position retention bracket assembly clip interior surface 1634 about the interlock coupling groove 1532. The tongue position retention bracket body 1610 is shaped to comfortably contact a portion of a face of the patient with the tongue position retention bracket face contacting surface 1612. This can include a lip, a chin, a cheek, or any other facial feature. In the exemplary embodiment, the tongue position retention bracket body 1610 is fabricated having an "S" shape in a radial direction. The exemplary "S" shape initially extends radially outward, then turning towards a proximal axial direction, and returning to a radially outward direction. The tongue position retention bracket body 1610 can additionally have a concave shape on a tongue position retention bracket face contacting surface 1612 and a convex shape on the exposed or exterior surface.

A tongue position retention bracket valve guard 1640 can extend forward from the exterior surface of the tongue position retention bracket body 1610. The tongue position retention bracket valve guard 1640 would be shaped to guard the air extraction valve 1540 against inadvertent contact with other objects which might accidentally open the duck valve slit 1546 and disrupt the retained vacuum within the tongue receiving cavity 1512.

Figure 46:
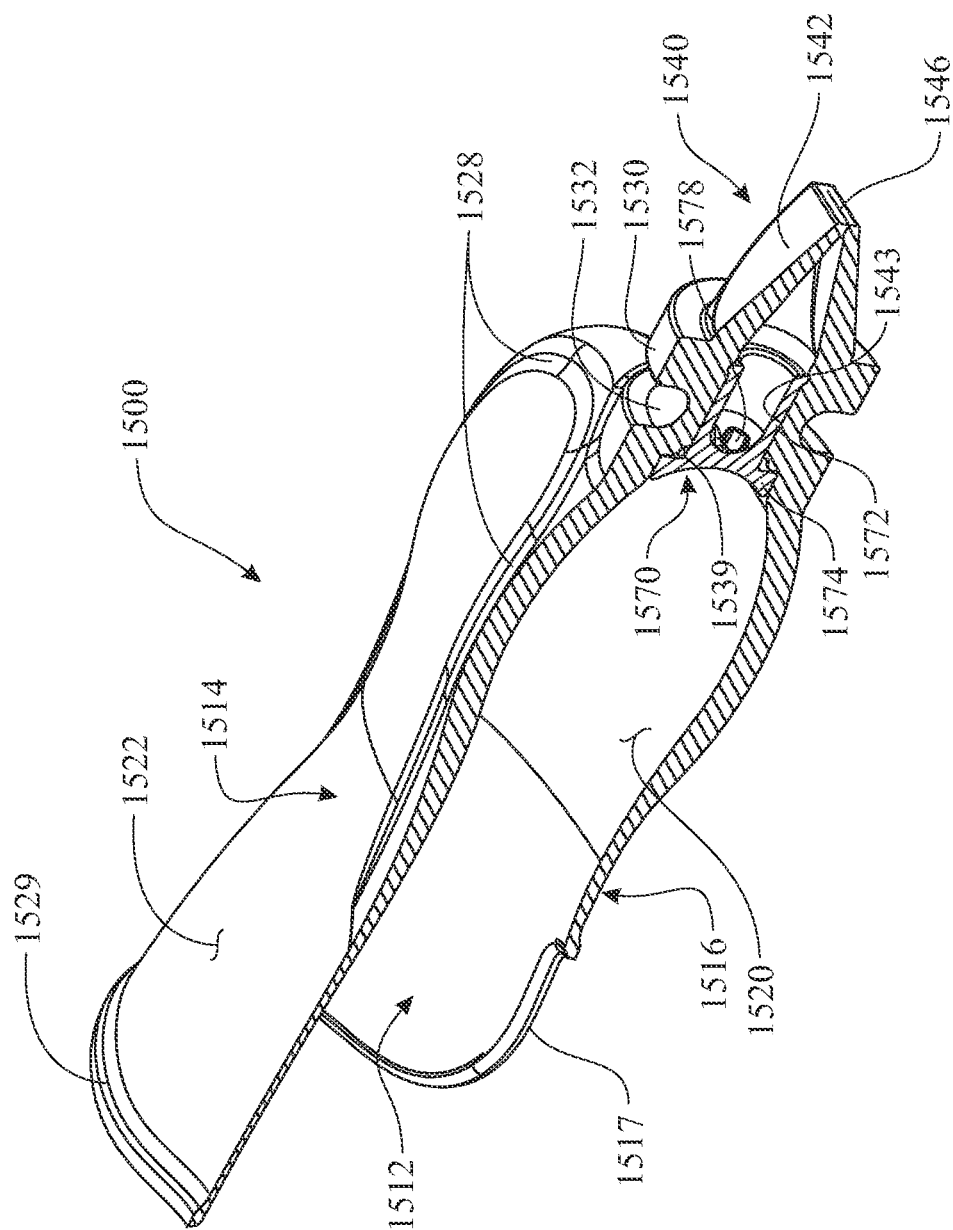
FIG. 46 presents an isometric top sectioned view the exemplary tongue attachment subassembly originally introduced in FIG. 42, the section being taken along a central elongated axis or section line 46-46 of FIG. 42.

The sleep apnea treatment system is assembled by inserting the tongue protection insert 1570 is inserted into the valve passageway 1543 of the tongue attachment subassembly 1500, to a position where the tongue protection insert interior or proximal flange 1574 is seated within the respective cavity within the tongue receiving cavity 1512, as best shown in FIG. 46.

The tongue attachment subassembly 1500 is placed onto the patient's tongue 300 in a manner similar to process described for the tongue attachment subassembly 100. Air is removed from the tongue receiving cavity 1512 by drawing a vacuum through the duck valve slit 1546 of the air extraction valve 1540 and the series of tongue protection insert interior flange vacuum orifices 1578, sealing the tongue receiving cavity 1512 against the individual's tongue 300. The tongue protection insert interior flange arched surface 1575 in combination with the series of tongue protection insert interior flange vacuum orifices 1578 protects the tongue from being drawn into the tongue protection insert tubular body vacuum passageway 1577. Once a sufficient vacuum is generated within the tongue receiving cavity 1512, the vacuum is retained by closure of the duck valve slit 1546 by the duckbill valve 1542, retaining the tongue attachment subassembly 1500 in position on the patient's tongue 300.

The tongue position retention bracket 1600 is assembled to the tongue attachment subassembly 1500 by extending the patient's tongue 300 forward, then sliding the tongue position retention bracket assembly clip interior surface 1634 into the interlock coupling groove 1532. The tongue position retention bracket assembly clip interior surface 1634 circumscribes a circumference of greater than 180 degrees about the tongue position retention bracket assembly clip 1632. A tongue position retention bracket assembly clip retention feature 1636 is formed at each end of the tongue position retention bracket assembly clip interior surface 1634. The two tongue position retention bracket assembly clip retention features 1636 are designed to retain the tongue position retention bracket assembly clip interior surface 1634 about the interlock coupling groove 1532. When the tongue position retention bracket 1600 is assembled to the tongue attachment subassembly 1500, the tongue position retention bracket valve guard 1640 is positioned to guard the air extraction valve 1540 against accidentally releasing the contained vacuum within the tongue receiving cavity 1512.

After securing the tongue position retention bracket 1600 to the tongue attachment subassembly 1500, the patient would relax their tongue 300, drawing the patient's tongue 300 rearward until the tongue position retention bracket face contacting surface 1612 rests against the patient's face.

Although the above described process installs the tongue attachment subassembly 1500 onto the patient's tongue 300 prior to assembly of the tongue position retention bracket 1600 to the tongue attachment subassembly 1500, it is understood that the tongue position retention bracket 1600 can be assembled to the tongue attachment subassembly 1500 prior to installing the tongue attachment subassembly 1500 onto the patient's tongue 300. When using this process, the step of drawing a vacuum from the tongue receiving cavity 1512 requires added attention due to the installed tongue position retention bracket valve guard 1640.

Once assembled and properly placed upon the patient, the sleep apnea treatment system would significantly reduce any potential effects of sleep apnea.

The sleep apnea treatment system would be removed by separating the tongue position retention bracket 1600 from the tongue attachment subassembly 1500 and compressing the sides of the duckbill valve 1542, opening the duck valve slit 1546, and releasing the vacuum from within the tongue receiving cavity 1512.

As previously stated, the tongue positioning retention system can be employed for any of a number of applications that would benefit placement and retention of the individual's tongue 300. This includes sleep apnea; during any medical procedure, such as those requiring delivery of a gas to a patient, delivery of oxygen to the patient, conscience sedation anesthesia, and the like; or any other application to ensure the patient's tongue 300 does not become lodged in the patient's throat, and the like.

For example, a tongue attachment subassembly 1700 can be adapted for use for in conjunction with a medical procedure to retain the patient's tongue from becoming lodged in the patient's throat, as illustrated in FIGS. 49 through 53. The tongue attachment subassembly 1700 can include features to cooperate with a gas management mask. The tongue attachment subassembly 1700 is a modified variant of the tongue attachment subassembly 1500. Like features of the tongue attachment subassembly 1700 and the tongue attachment subassembly 1500 are numbered the same, except preceded by the numeral "17". The tongue attachment subassembly 1700 is fabricated by removing the air extraction valve 1540 from the tongue attachment subassembly 1500. The air extraction valve 1540 would be removed by shearing the material along the exterior surface of the interlock coupling flange 1530 to form the tongue attachment subassembly 1700. The shearing can be accomplished using any suitable tool, such as a knife, a razor blade, a razor knife, scissors, and the like. After removing the air extraction valve 1540 from the tongue attachment subassembly 1500, the function of the duck valve slit 1546 is replaced by a vacuum passageway 1746.

A tongue protection insert 1770 is a modified version of the tongue protection insert 1570. The tongue protection insert 1770 includes a tongue protection insert tubular vacuum tube retention barb 1773 formed along a portion of the tongue protection insert tubular body 1772 that extends outward from a distal or exterior surface of the interlock coupling flange 1730.

A mask retention bracket 1800 is assembled to the tongue attachment subassembly 1700 forming a sedation procedure tongue retention system. The mask retention bracket 1800 and the tongue position retention bracket 1600 have like elements. The like elements of the mask retention bracket 1800 and the tongue position retention bracket 1600 are numbered the same, except preceded by the numeral "18". The mask retention bracket 1800 includes an attachment feature for attaching the mask retention bracket 1800 to the tongue attachment subassembly 1700. The exemplary attachment feature is a mask retention bracket assembly clip 1832, which is like the tongue position retention bracket assembly clip 1632. In the exemplary embodiment, the mask retention bracket 1800 includes a pair of mask retention bracket bodies 1810, each mask retention bracket body 1810 extends radially outward from the mask retention bracket assembly clip 1832, one mask retention bracket body 1810 mirroring the other mask retention bracket body 1810. Each mask retention bracket body 1810 can be of any suitable shape to engage with and retain a gas management mask 1900 (FIGS. 52 and 53) in position. The exemplary mask retention bracket bodies 1810 are formed having an arched shape. The arch is formed having a convex outer or exposed surface and an opposite, concave inner or mask contacting surface 1812.

The gas management mask 1900 is provided to aid in delivery of anesthetic gases and other gases, as well as to provide other management functions. The gas management mask 1900 includes a gas management mask body 1910 having a shape for covering a nose and mouth of a patient. Most gas management masks 1900 are commonly fabricated of a clear, transparent, or translucent flexible gas impervious material. A few gas management masks 1900 designs are of a frame styled structure and use a diffuser to deliver the gas. A rear edge of the gas management mask face seal 1913 defines a gas management mask face seal 1913. A series of openings are provided passing through the gas management mask body 1910 for functional applications. A first opening is a vacuum delivery aperture (not identified, but understood as being provided for insertion of the tongue protection insert 1770 therethrough). A second opening is a gas delivery hose connection 1920. The gas delivery hose connection 1920 retains a gas delivery hose 1954 in a desired position.

Figure 51:
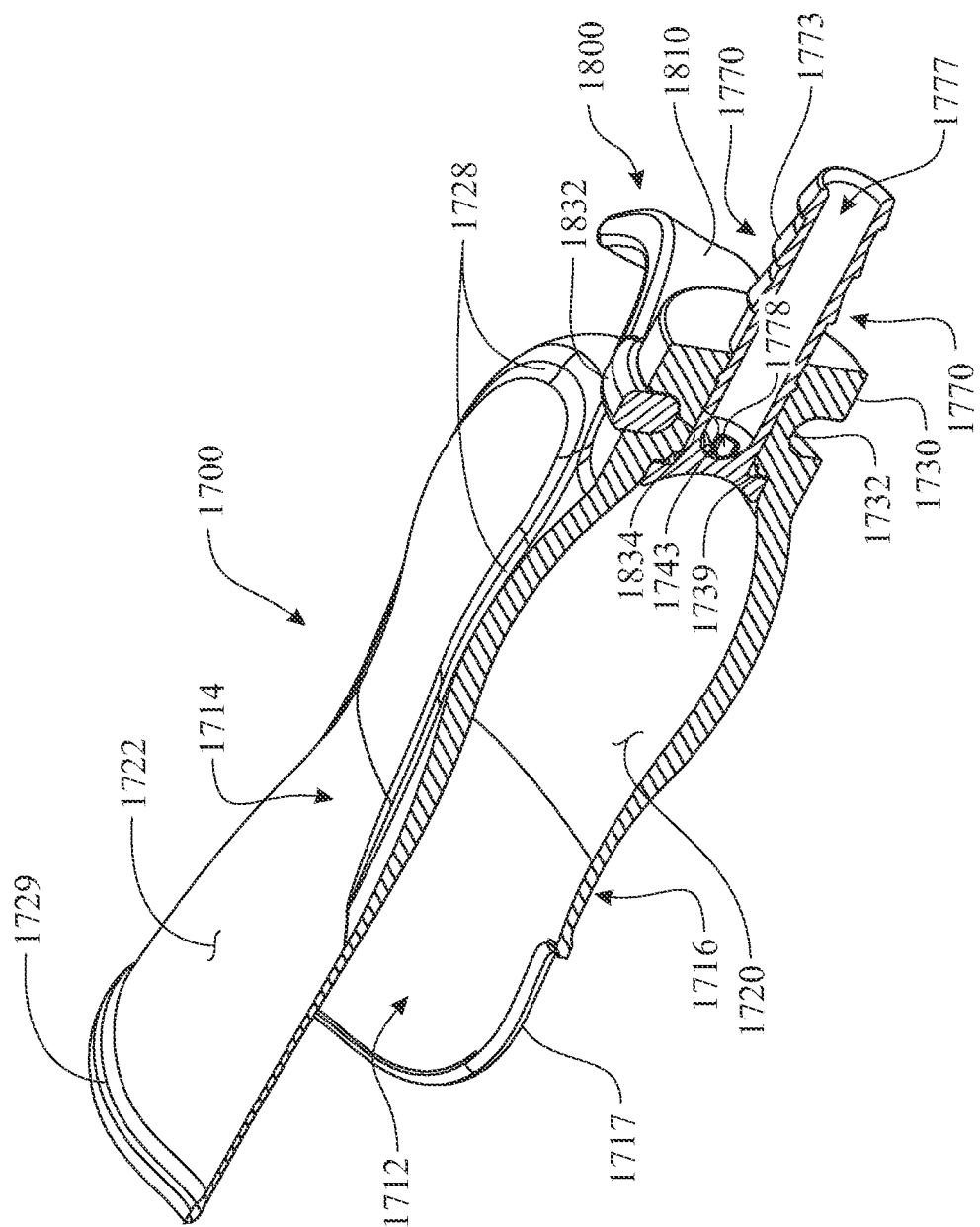
FIG. 51 presents an isometric top sectioned view the components forming the gas management mask application system originally introduced in an exploded configuration in FIG. 49, the section being taken along a central elongated axis or section line 51-51 of FIG. 50.
Figure 52:
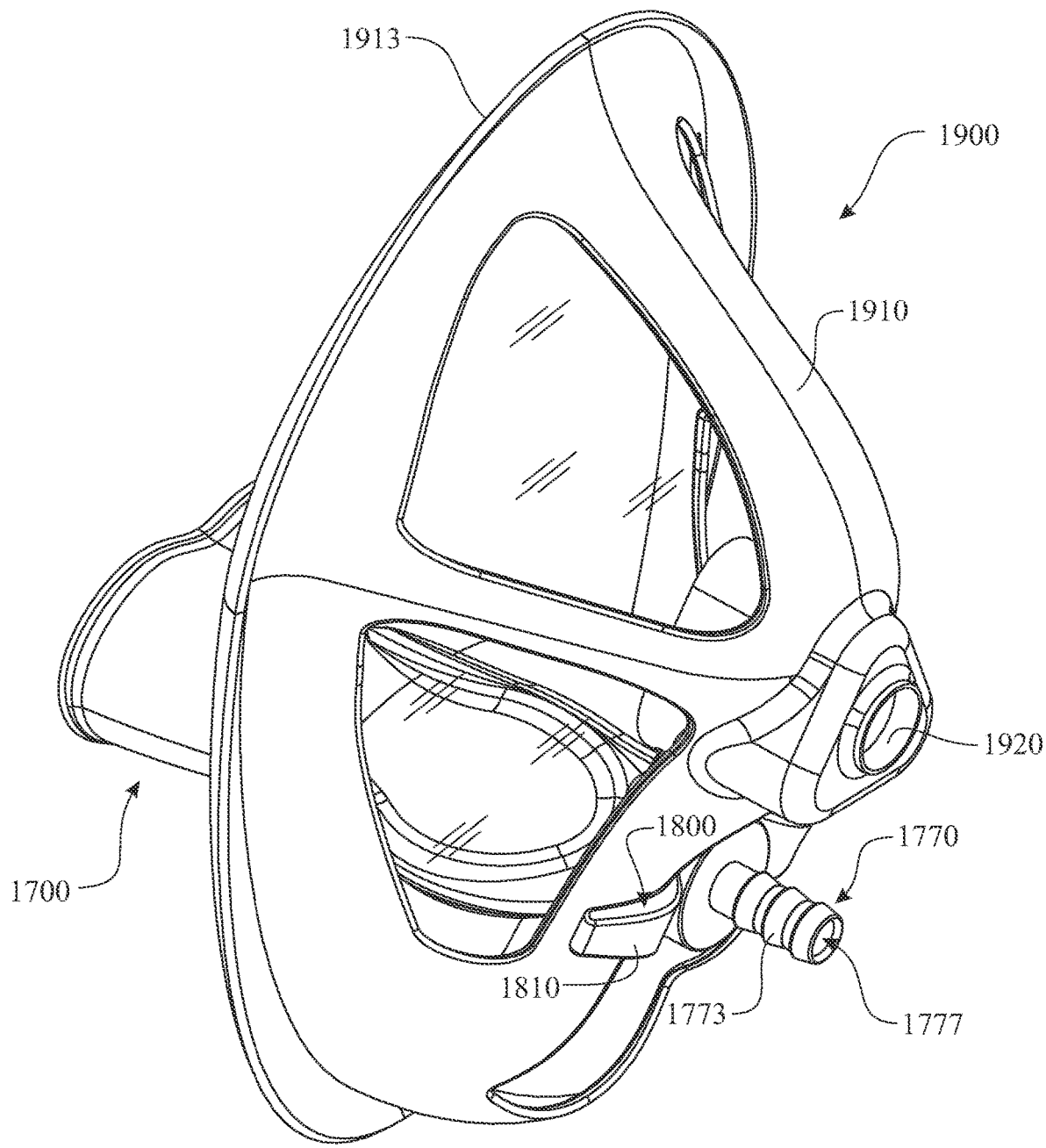
FIG. 52 presents an isometric top assembly view of the components forming an anesthesia delivery system originally introduced in an exploded configuration in FIG. 49, and introducing a gas management mask.
Figure 53:
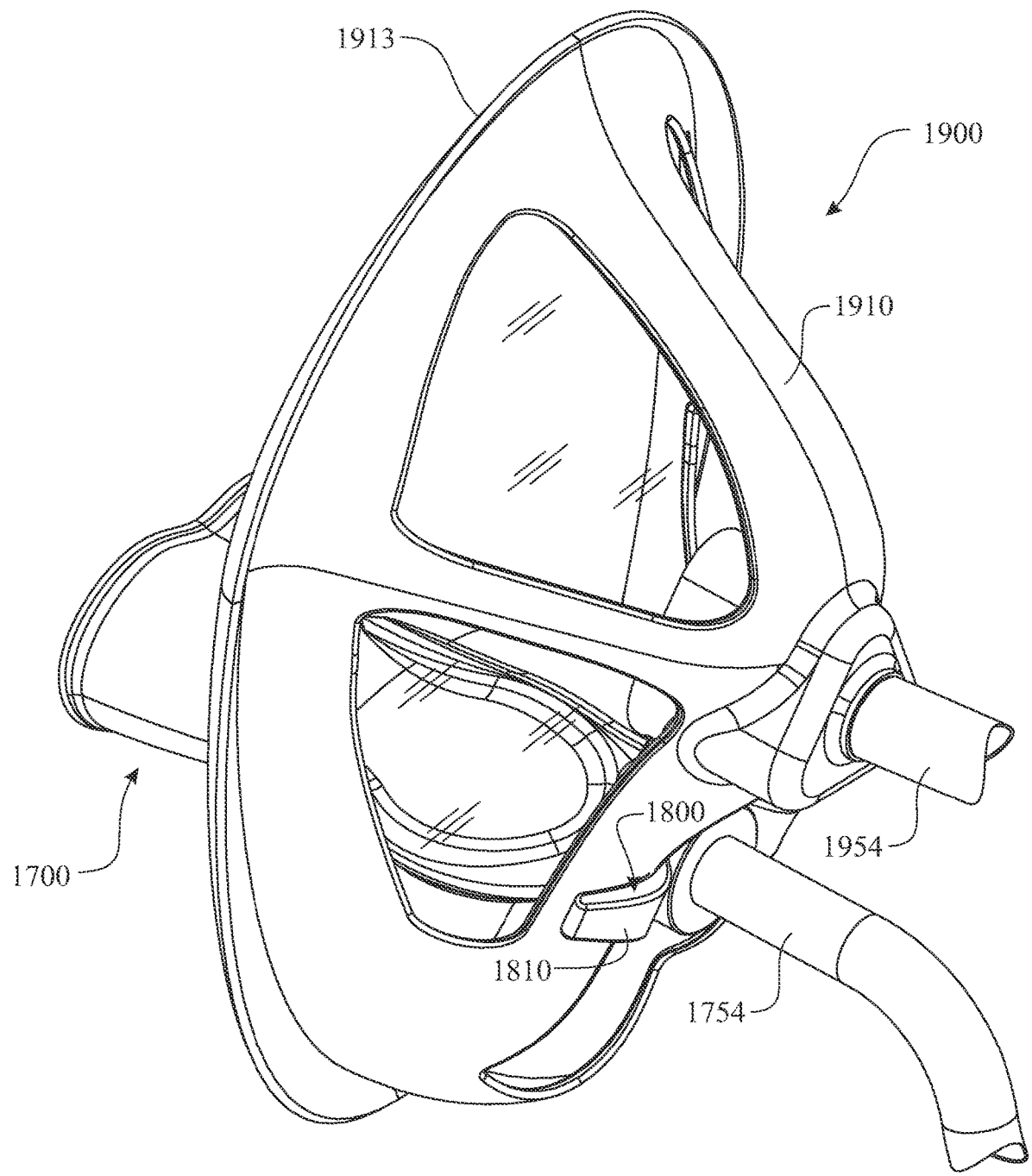
FIG. 53 presents an isometric top assembly view of the components forming the gas management mask application system further comprising a vacuum hose and a gas delivery hose.

The gas management mask retention system is assembled by removing the air extraction valve 1540 from the tongue attachment subassembly 1500 to create the tongue attachment subassembly 1700. The tongue protection insert 1770 is inserted into the valve passageway 1743 of the tongue attachment subassembly 1700, to a position where the tongue protection insert interior flange 1774 is seated within the respective cavity within the tongue receiving cavity 1712 and a section of the tongue protection insert tubular body 1772 containing the tongue protection insert tubular vacuum tube retention barb 1773 extends forward from the exposed surface of the interlock coupling flange 1730, as best shown in FIG. 51.

The tongue attachment subassembly 1700 is placed onto the patient's tongue 300 in a manner similar to process described for the tongue attachment subassembly 100. Air is removed from the tongue receiving cavity 1712 by drawing a vacuum through the tongue protection insert tubular body vacuum passageway 1777 and the series of tongue protection insert interior flange vacuum orifices 1778, sealing the tongue receiving cavity 1712 against the individual's tongue 300. The tongue protection insert interior flange arched surface 1775 in combination with the series of tongue protection insert interior flange vacuum orifices 1778 protects the tongue from being drawn into the tongue protection insert tubular body vacuum passageway 1777. A continuous vacuum flow would be provided by an external vacuum source drawn through a tongue protection insert vacuum supply line 1754 (FIG. 53), retaining the tongue attachment subassembly 1700 in position on the patient's tongue 300.

The gas management mask 1900 is placed onto the tongue attachment subassembly 1700 by sliding the exposed portion of the tongue protection insert 1770 through an aperture formed through the gas management mask body 1910. Once the gas management mask face seal 1913 is positioned against the patient's face, the mask retention bracket 1800 is assembled to the tongue attachment subassembly 1700 by sliding the mask retention bracket assembly clip interior surface 1834 into the interlock coupling groove 1732. The mask retention bracket assembly clip interior surface 1834 circumscribes a circumference of greater than 180 degrees about the mask retention bracket assembly clip 1832. A mask retention bracket assembly clip retention feature 1836 is formed at each end of the mask retention bracket assembly clip interior surface 1834. The pair of mask retention bracket assembly clip retention feature 1836 is designed to retain the mask retention bracket assembly clip interior surface 1834 about the interlock coupling groove 1732. The mask retention bracket body 1810 retains the gas management mask 1900 against the patient's face by applying a pressure from the mask contacting surface 1812 onto the surface of the gas management mask body 1910. In turn, the gas management mask face seal 1913 creates a gas impervious seal against the patient's face.

The gas management mask 1900 can be inserted into the tongue protection insert vacuum supply line 1754 before installing the tongue attachment subassembly 1700 onto the patient's tongue 300 or the completed assembly can be placed upon the patient subsequent to the assembly process.

At some point during the assembly process a gas delivery hose 1954 is assembled to or inserted through the gas delivery hose connection 1920 of the gas management mask 1900.

Once assembled and properly placed upon the patient, the gas management mask retention system can be used for delivery of any desired gas. It is recognized that the same gas management mask retention system can be adapted for use in delivering any desired gas, such as nitrous-oxide, oxygen, and the like, while maintaining the tongue in a forward position. The gas management mask retention system can be used with or without any other attachment mechanism, such as a mask strap. The configuration of the delivery system can be used to retain the gas management mask 1900 in position throughout any suitable procedure. It is understood that a common mask with a strap or any other suitable retention mechanism can be used, allowing the tongue attachment subassembly 1700 to be secured or removed while the mask is still on the patient. The inclusion of a strap will also reduce any stresses on the patient's tongue 300.

The gas management mask retention y system would be removed by ceasing the vacuum from the external vacuum source. The removal of the vacuum from the tongue receiving cavity 1712 will release the tongue attachment subassembly 1700 from the patient's tongue 300, allowing for removal of the gas management mask retention system from the patient. Once removed, the gas management mask retention delivery system can be disassembled.

Although the illustrations present versions of tongue embracing members having different features, it is understood that features of any exemplary tongue embracing members can be adapted to any of the other exemplary tongue embracing members.

As previously introduced, the interlock coupling groove 1532 enables the adaptation of the tongue attachment subassembly 1500 to any of a variety of applications. The interlock coupling groove 1532 is provided as an accessory attachment interface; being employed to receive and retain the accessory attachment. In the previous example, the tongue position retention bracket 1600 is attached to the tongue attachment subassembly 1500 by seating the interlock coupling groove 1532 of the tongue attachment subassembly 1500 into the tongue position retention bracket assembly clip interior surface 1634 of the tongue position retention bracket 1600.

Figure 54:
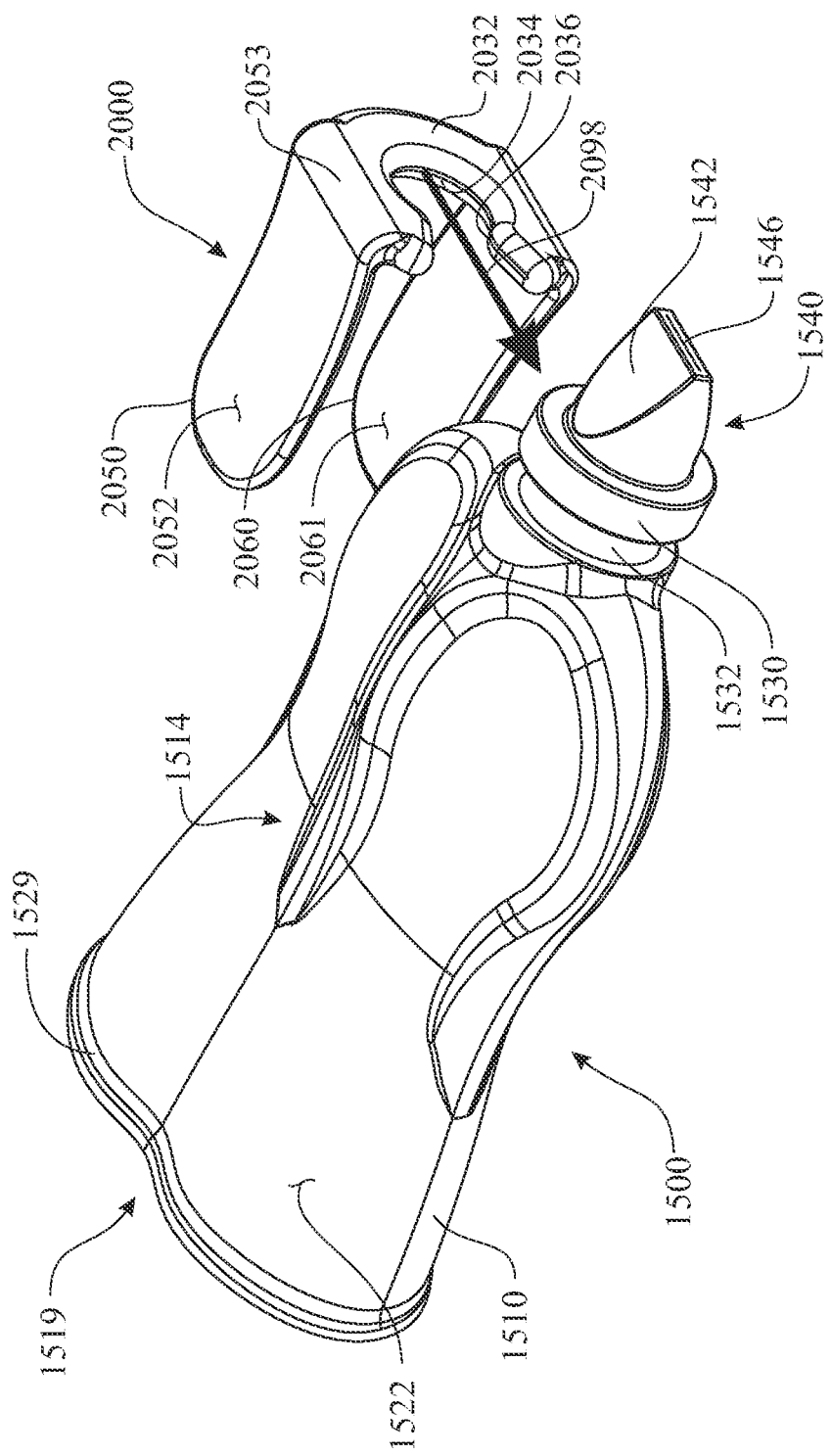
FIG. 54 presents an isometric top exploded assembly view introducing a tongue compression component for use in conjunction with the tongue attachment subassembly.
Figure 55:
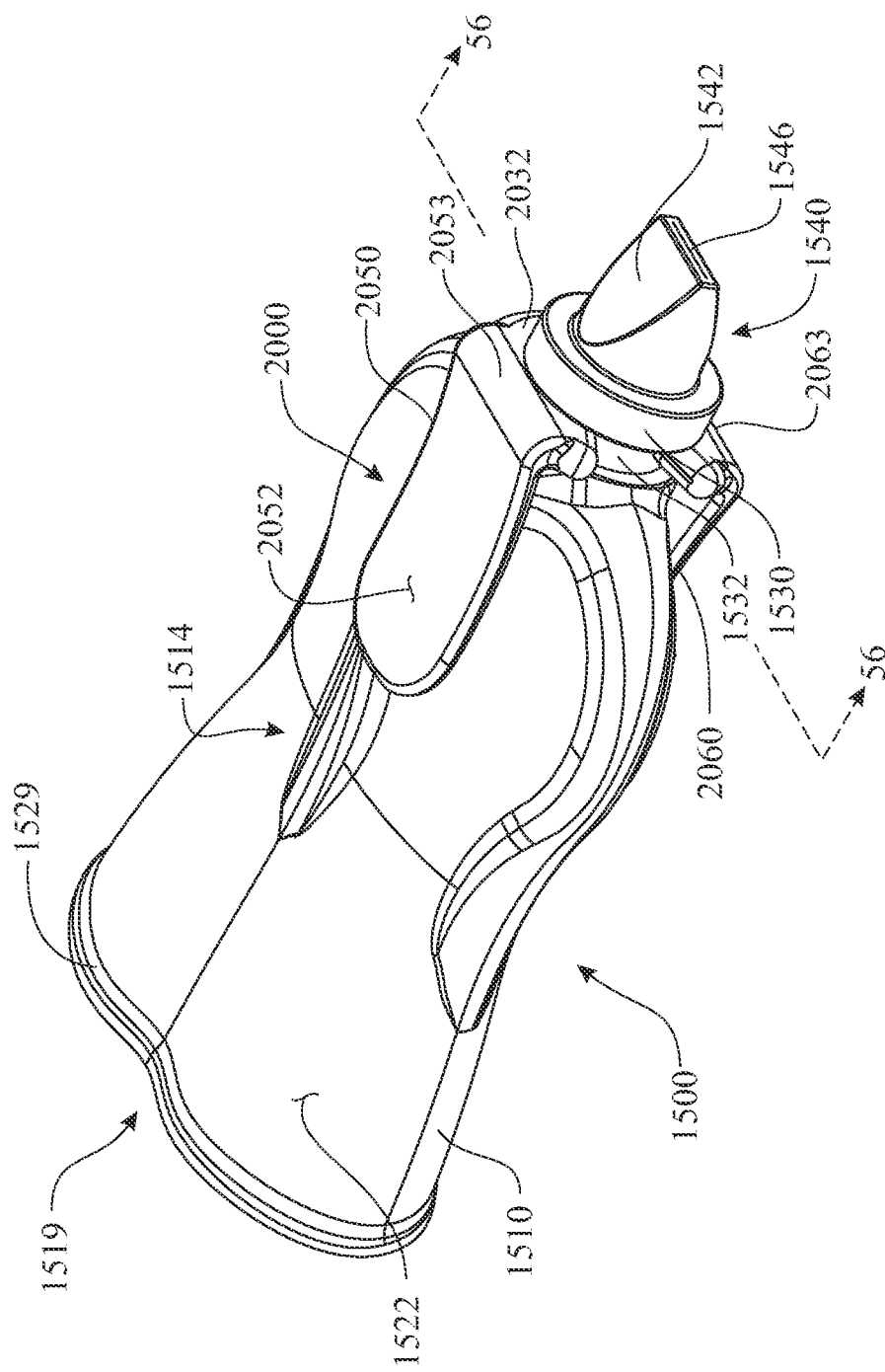
FIG. 55 presents an isometric top assembly view of the tongue compression component, originally introduced in FIG. 54, assembled onto the tongue attachment subassembly in preparation for use.
Figure 56:
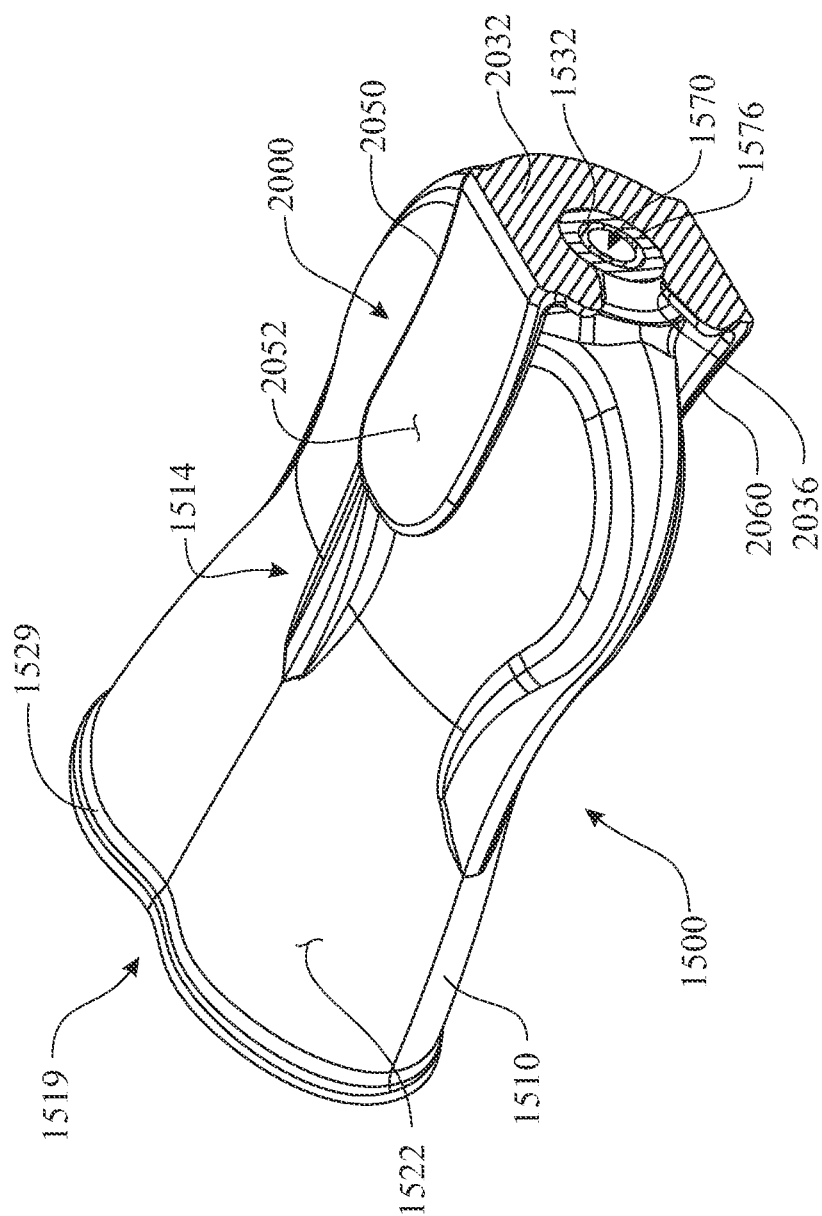
FIG. 56 presents an isometric sectioned top assembly view of the tongue compression component assembled onto the tongue attachment subassembly in preparation for use, as originally introduced in FIG. 55, the section being taken along section line 56-56 of FIG. 55.

Another example is introduced in FIGS. 54 through 56. A tongue compression component 2000 is provided to retain a natural shape of a patient's tongue while wearing the tongue attachment subassembly 1500. The tongue compression component 2000 utilizes the same scheme for assembly of the tongue compression component 2000 to the tongue attachment subassembly 1500. The tongue compression component 2000 includes a pair of tongue compression arms 2050, 2060 extending in a same direction, substantially parallel with one another from a tongue compression arm cantilever transition section 2053. A tongue compression arm cantilever transition section 2053, 2063 provides a transition between the tongue compression component assembly clip 2032 and each respective tongue compression arm 2050, 2060. Each exemplary tongue compression arm 2050, 2060 is formed having an exposed tongue compression arm surface (identified by example as reference numeral 2052 for the upper tongue compression arm 2050) and a contacting tongue compression arm surface (identified by example as reference numeral 2061 for the lower tongue compression arm 2060).

The attachment scheme of the tongue compression component 2000 includes a tongue compression component assembly clip interior surface 2034 formed within a tongue compression component assembly clip 2032. The tongue compression component assembly clip interior surface 2034 is preferably shaped having a circumference that is greater than 180 degrees; extending between a pair of tongue compression component assembly clip retention features 2036. The shape of the tongue compression component assembly clip interior surface 2034 retains the tongue compression component 2000 upon the interlock coupling groove 1532 of the tongue attachment subassembly 1500 in a lateral direction. The two surfaces (outer and interior surfaces) of the tongue compression component assembly clip 2032 seat against each respective surface of the interlock coupling flange 1530 and the opposite surface defined by a body of the sheath 1510. The flanged surfaces retain the tongue compression component 2000 in a longitudinal direction. The tongue compression component 2000 is assembled to the tongue attachment subassembly 1500 by sliding the tongue compression component assembly clip interior surface 2034 over the interlock coupling groove 1532, in accordance with a tongue compression component assembly direction 2098 or restated in an opposite manner, by sliding the interlock coupling groove 1532 into the tongue compression component assembly clip interior surface 2034. The tongue compression component assembly clip interior surface 2034 is seated onto the interlock coupling groove 1532 and secured with the tongue compression component assembly clip retention features 2036, as shown in FIGS. 55 and 56.

As illustrated in the exemplary embodiment, each tongue compression arm 2050, 2060 is formed having an arched shape. Each contacting tongue compression arm surface 2061 is formed having a convex shaped surface. Subsequently, each exposed tongue compression arm surface 2052 is formed having a concave surface. Each tongue compression arm 2050, 2060 can have a constant thickness along a substantial portion of a length of the tongue compression arm 2050, 2060 or the thickness can vary along the respective length. The thickness of a cantilevered element contributes to the bending properties of the element. By varying the thickness, the designer can control the bending properties of the tongue compression arms 2050, 2060, thus tailoring the force applied by the tongue compression component 2000 onto the patient's tongue 310. In one example, the thickness of the tongue compression arms 2050, 2060 can decrease in relation to a distance from the tongue compression arm cantilever transition section 2053, 2063.

Another contributor to the bending properties includes the modulus of elasticity of the material used to fabricate the tongue compression component 2000.

Figure 58:
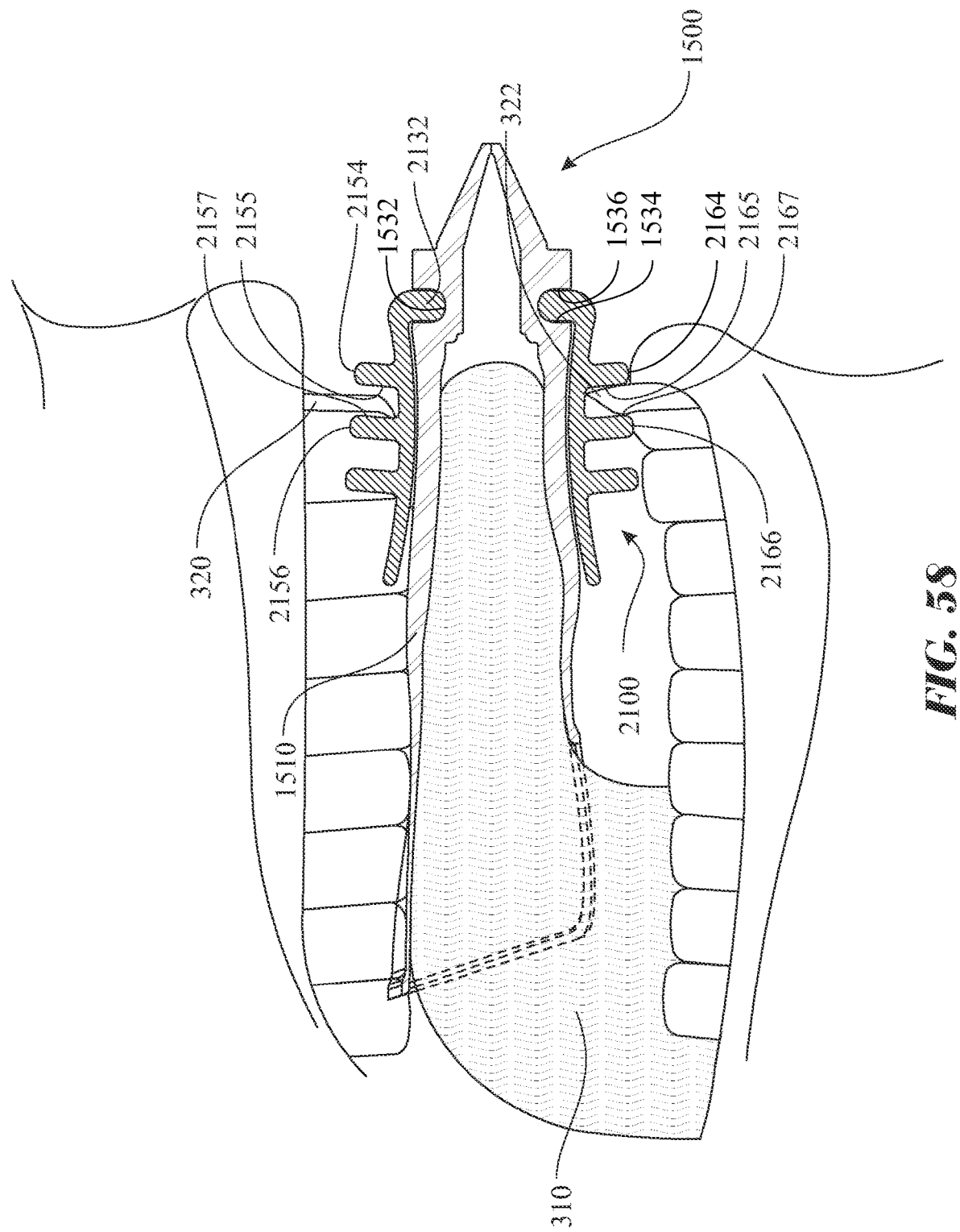
FIG. 58 presents a side sectioned view of the modified version of the tongue compression component originally introduced in FIG. 57 in conjunction with the tongue attachment subassembly, the illustration demonstrating the combination being worn by a patient.

The shape of the curve of the tongue compression arms 2050, 2060 defines the point of contact or location of application of pressure upon the patient's tongue 310, as shown in FIG. 58.

When worn, the tongue attachment subassembly 1500 has a tendency to reshape the patient's tongue from an oval shape into an unnatural, more rounded shape. The tongue compression component 2000 restores the patient's tongue 310 to the tongue's natural shape. Additionally, the combination of the tongue attachment subassembly 1500 and the tongue compression component 2000 can be utilized to treat sleep apnea.

The tongue compression component 2000 can be used with a tongue attachment subassembly 1500 inclusive of the sheath shape retention feature 1528, as shown, or exclusive of the sheath shape retention feature 1528. It is desirable to include the tongue protection insert 1570 within the valve passageway 1543 (FIG. 46) of the tongue attachment subassembly 1500 when using the tongue compression component 2000 with the tongue attachment subassembly 1500. The tongue protection insert 1570 ensures a tip of the patient's tongue 310 is not drawn into the valve passageway 1543 by the vacuum formed within the tongue receiving cavity 1512 (FIG. 46) of the tongue attachment subassembly 1500.

Figure 57:
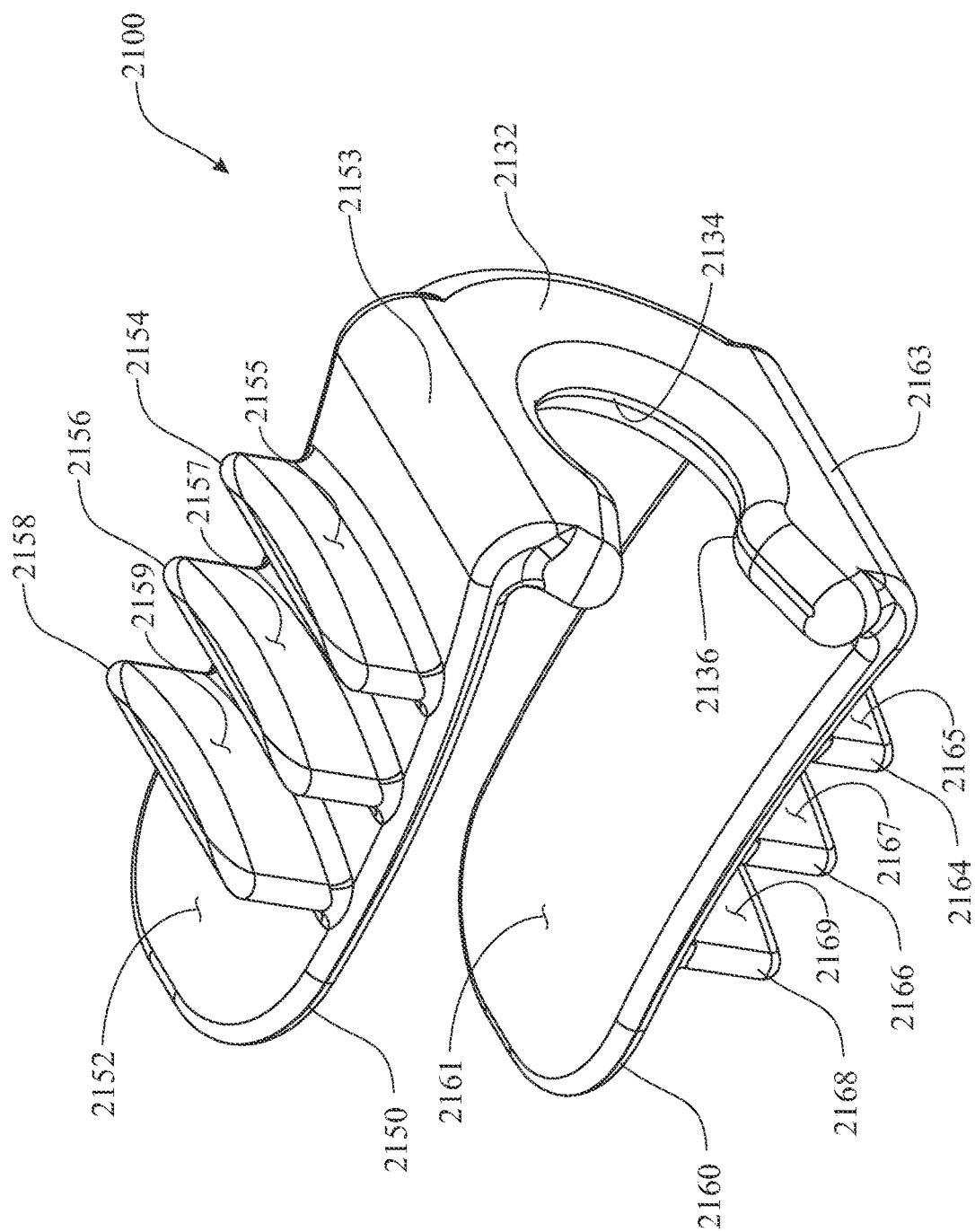
FIG. 57 presents an isometric top view of a modified version of the tongue compression component originally introduced in FIG. 54, wherein the modified version of the tongue compression component introduces teeth locating projections.

The tongue compression component 2000 can be modified by introducing a tooth/teeth engaging arrangement, as introduced as a teeth engaging tongue compression component 2100 illustrated in FIG. 57, and shown in use in FIG. 58. The teeth engaging tongue compression component 2100 is similar to the tongue compression component 2000, with like elements of the teeth engaging tongue compression component 2100 being numbered in a similar manner as the tongue compression component 2000, with a prefix of the numeral "21".

The exemplary teeth engaging tongue compression component 2100 includes three pair of locating projections 2154, 2164; 2156, 2166; 2158, 2168. Each locating projection includes a first tooth contacting surface and a second tooth contacting surface. The exemplary teeth engaging tongue compression component 2100 includes an outer pair of locating projections 2154, 2164; a central pair of locating projections 2156, 2166; and an inner pair of locating projections 2158, 2168.

The outer locating projection 2154 provides a first and second outer locating projection tooth contacting surface 2155. The outer locating projection 2164 provides a first and second outer locating projection tooth contacting surface 2165. The central locating projection 2156 provides a first and second central locating projection tooth contacting surface 2157. The central locating projection 2166 provides a first and second central locating projection tooth contacting surface 2167. The inner locating projection 2158 provides a first and second inner locating projection tooth contacting surface 2159. The inner locating projection 2168 provides a first and second inner locating projection tooth contacting surface 2169.

The teeth engaging tongue compression component 2100 can be arranged comprising any of the following configurations or combinations thereof:

(a) one tooth locating projection 2154, 2156, 2158, 2164, 2166, 2168 on either the upper tongue compression arm 2150 or the lower tongue compression arm 2160;

(b) a pair of tooth/teeth locating projections extending outward from the same tongue compression arm 2050, 2060, more specifically any pair of tooth/teeth locating projections 2154, 2156, 2158 extending outward from the upper tongue compression arm 2150 or any pair of tooth/teeth locating projections 2164, 2166, 2168 extending outward from the lower tongue compression arm 2160;

(c) multiple tooth/teeth locating projections extending outward from the same tongue compression arm 2150, 2160, more specifically multiple tooth/teeth locating projections 2154, 2156, 2158 extending outward from the upper tongue compression arm 2150 or multiple tooth/teeth locating projections 2164, 2166, 2168 extending outward from the lower tongue compression arm 2160;

(d) a pair of tooth/teeth locating projections (2154, 2164); (2156, 2166); (2158, 2168), a first respective tooth/teeth locating projection (2154, 2156, 2158) of the pair of tooth/teeth locating projections (2154, 2164); (2156, 2166); (2158, 2168) extending outward from the upper tongue compression arm 2150 and a second respective tooth/teeth locating projection (2164, 2166, 2168) of the pair of tooth/teeth locating projections (2154, 2164); (2156, 2166); (2158, 2168) extending outward from the lower tongue compression arm 2160, or (e) any combination of the above.

Adjacent pairs of tooth/teeth locating projections on a same respective tongue compression arm 2150, 2160 would be suitably spaced apart from one another to receive an anticipated tooth size.

It is understood that the same function can be obtained with a teeth engaging tongue compression component 2100 having a modified design. In an alternative configuration, the tooth/teeth locating projections and the respective tongue compression arm 2150, 2160 can be formed as a single, unitary element, such as having a serpentine shape.

In use, the teeth engaging tongue compression component 2100 would be assembled to the tongue attachment subassembly 1500 in a manner as previously described for assembling of the tongue compression component 2000 onto the tongue attachment subassembly 1500. The tongue attachment subassembly 1500 would be placed upon the patient's tongue 310. As the tongue attachment subassembly 1500 is slid onto the patient's tongue 310, the pair of tongue compression arms 2150, 2160 applies a restoration and retention force to the patient's tongue 310. The convex shaped surfaces 2161 of the tongue compression arms 2150, 2160 applies a pressure to the patient's tongue 310 at a location proximate or slightly inward of a distal end of the patient's tongue 310.

Air can be extracted from within the tongue receiving cavity 1512 or the volume/space between the surface of the patient's tongue 310 and the tongue engagement surface 1520 of the tongue attachment subassembly 1500 using any suitable method. The exemplary method utilizes the air extraction valve 1540. The tongue protection insert 1570 protects the tip of the patient's tongue 310 from being drawn into the valve passageway 1543.

The application of the tongue attachment subassembly 1500 upon the patient's tongue 310 can cause the patient's tongue 310 to be drawn inward from the sides and thicken or increase in dimension between the dorsal and ventral sides of the tongue. Conversely, the teeth engaging tongue compression component 2100 applies a restoring force to the patient's tongue 310, where the compression force generated by the contacting surfaces 2161 of the pair of tongue compression arms 2150, 2160 reduces the thickness between the dorsal and ventral sides of the tongue and broadens the width of the tongue, thus restoring the patient's tongue 310 to its natural shape.

The tooth/teeth locating projections 2154, 2156, 2158, 2164, 2166, 2168 are located respective to the tongue compression component assembly clip 2132 to position the patient's tongue at a desired position within the patient's mouth respective to the patient's teeth 320, 322. The natural biting position of the patient's jaw retains the patient's teeth 320, 322 within the gap between adjacent tooth/teeth locating projections 2154, 2156, 2158, 2164, 2166, 2168. The patient's teeth 320, 322 would be restrained between two adjacent and facing locating projection tooth contacting surfaces (2155, 2157)(2157, 2159)(2165, 2167)(2167, 2169).

The position of the patient's tongue can be adjusted to optimize treatment for sleep apnea. The combination of the tongue attachment subassembly 1500 and the teeth engaging tongue compression component 2100 can include any of a number of options to modify the retained position of the patient's tongue 310 during use.

For example, several tongue compression components 2100, each teeth engaging tongue compression component 2100 having a configuration that differs from the others, can be provided to adjust the position of the patient's tongue 310.

In another example, the tongue compression component assembly clip 2132 can be adjustable respective to the tooth locating projections. The tongue compression arms 2150, 2160 can be slideably assembled to the tongue compression component assembly clip 2132, repositionably coupled to the tongue compression component assembly clip 2132, or any other suitable adjusting process.

In yet another example, a wax material can be provided upon the exposed tongue compression arm surface 2152 of each of the tongue compression arms 2150, 2160. The patient would heat the wax material, install the assembly comprising the tongue attachment subassembly 1500 and the teeth engaging tongue compression component 2100, place the patient's tongue at the desired position, than the patient would bite into the heated and softened wax. This process creates a mold of the patient's teeth 320, 322 within the wax. The wax can be supported by one or more features to isolate any flexing of the tongue compression arms 2150, 2160 from the wax formations.

Figure 59:
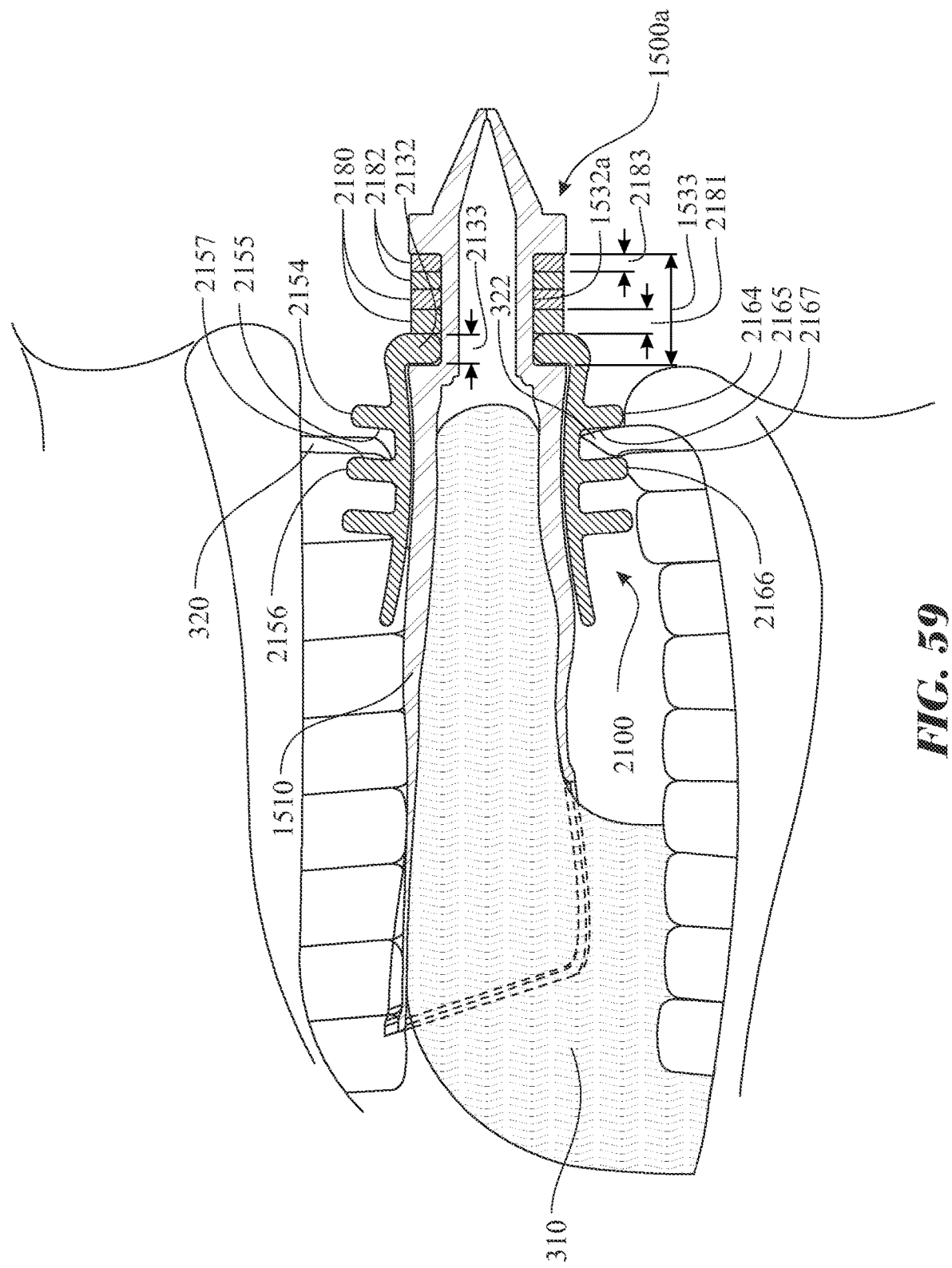
FIG. 59 presents a side sectioned view of the modified version of the tongue compression component originally introduced in FIG. 57 in conjunction with the tongue attachment subassembly and a series of spacers, the illustration demonstrating a first exemplary arrangement of spacers to located the tongue compression component.
Figure 60:
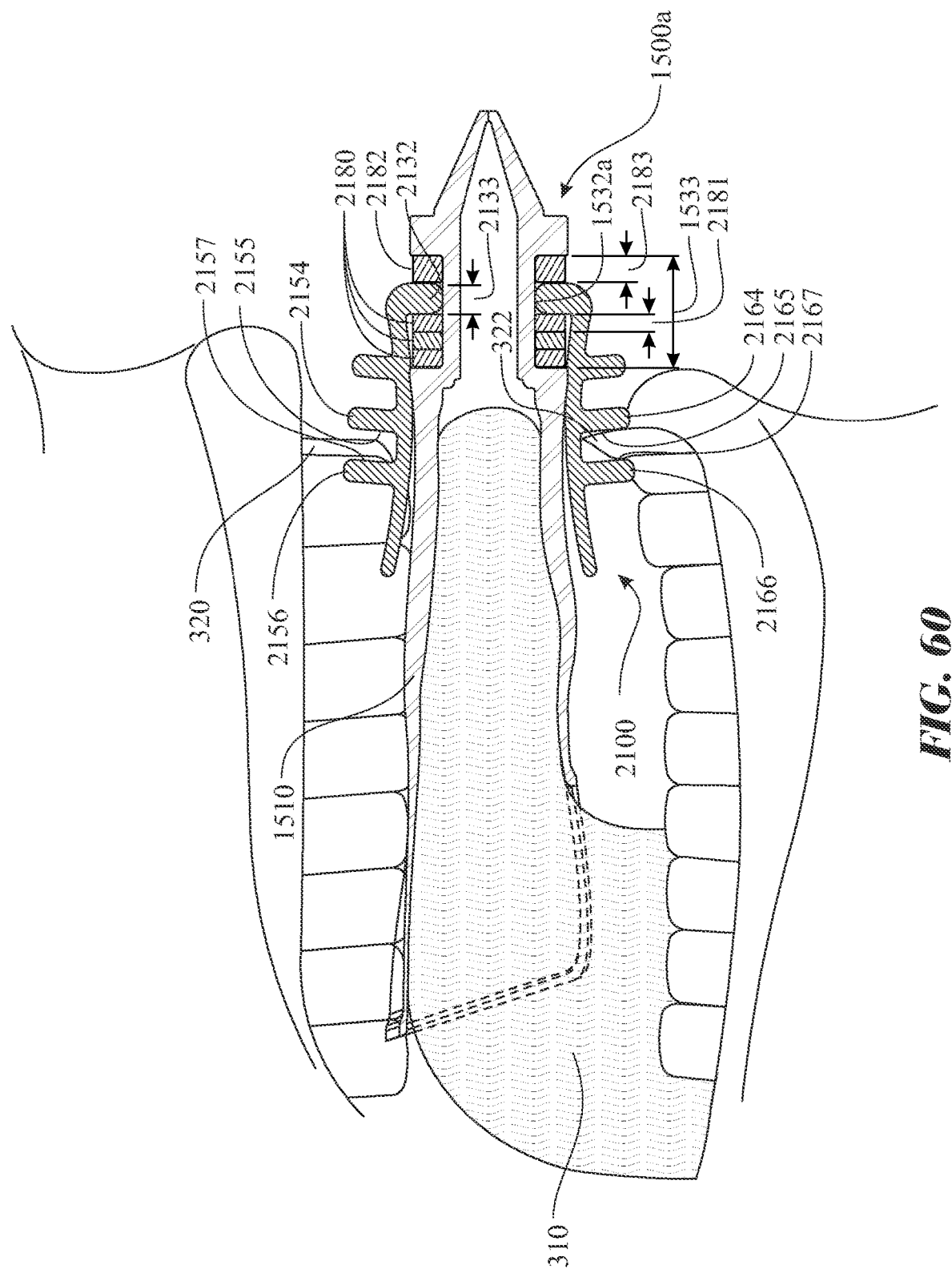
FIG. 60 presents a side sectioned view of the modified version of the tongue compression component originally introduced in FIG. 57 in conjunction with the tongue attachment subassembly and a series of spacers, the illustration demonstrating a second exemplary arrangement of spacers to located the tongue compression component.

The exemplary illustrations present a tongue compression component assembly clip 2132 having a thickness or a dimension spanning between a first flange engaging surface and a second flange engaging surface is substantially proximate a dimension spanning between a first (rearward or inner) flange surface 1534 and a second (forward or outer) flange surface 1536 defining the interlock coupling groove 1532. This arrangement can be modified to accommodate an adjustment scheme. In a modified arrangement, the thickness of the tongue compression component assembly clip 2132 can be reduced to a dimension 2133 that is shorter than the span 1533 of an interlock coupling groove 1532a or the span 1533a of the interlock coupling groove 1532a can be extended. A spacer ring 2180, 2182 having a thickness 2181, 2183 that is the difference between the thickness 2133 of the tongue compression component assembly clip 2132 and the span 1533 of the interlock coupling groove 1532a. Alternatively, the arrangement can employ a plurality of spacers 2180, 2182, where the sum of the thicknesses 2181, 2183 of the plurality of spacers 2180, 2182 equals the difference between the thickness 2133 of the tongue compression component assembly clip 2132 and the span 1533 of the interlock coupling groove 1532, as illustrated in FIGS. 59 and 60. The positioning of the teeth engaging tongue compression component 2100 is adjusted by varying a placement of the spacer 2180, 2182 or plurality of spacers 2180, 2182. For example, in one arrangement illustrated in FIG. 59, the at least one spacer 2180, 2182 can be inserted between the tongue compression component assembly clip 2132 and the forward or outer flange surface 1536 within the interlock coupling groove 1532a. This positions the teeth engaging tongue compression component 2100 rearward. In an alternative arrangement illustrated in FIG. 60, a first set comprising at least one spacer 2180, 2182 can be inserted between the tongue compression component assembly clip 2132 and the rearward or inner flange surface 1534 within the interlock coupling groove 1532 and a second set comprising at least one spacer 2180, 2182 can be inserted between the tongue compression component assembly clip 2132 and the forward or outer flange surface 1536 within the interlock coupling groove 1532. This positions the teeth engaging tongue compression component 2100 centrally within the groove 1532a. In yet another alternative arrangement (not illustrated, but well understood based upon FIGS. 59 and 60), the at least one spacer 2180, 2182 can be inserted between the tongue compression component assembly clip 2132 and the rearward or inner flange surface 1534 within the interlock coupling groove 1532. This positions the teeth engaging tongue compression component 2100 forward.

Once the assembly comprising the tongue attachment subassembly 1500 and the teeth engaging tongue compression component 2100 are properly secured in the patient's mouth, the patient can go to sleep and being treatment for sleep apnea.

Although the details presented herein, as illustrated in FIG. 58, utilize the teeth engaging tongue compression component 2100 to maintain the patient's tongue at a desired position, sleep apnea may be treated simply using the tongue compression component 2000. The uses of the combination of the tongue attachment subassembly 1500 and tongue compression component 2000 could sufficiently reposition and comfortably retain the patient's tongue in a position to provide the same affect and treatment for sleep apnea.

Figure 61:
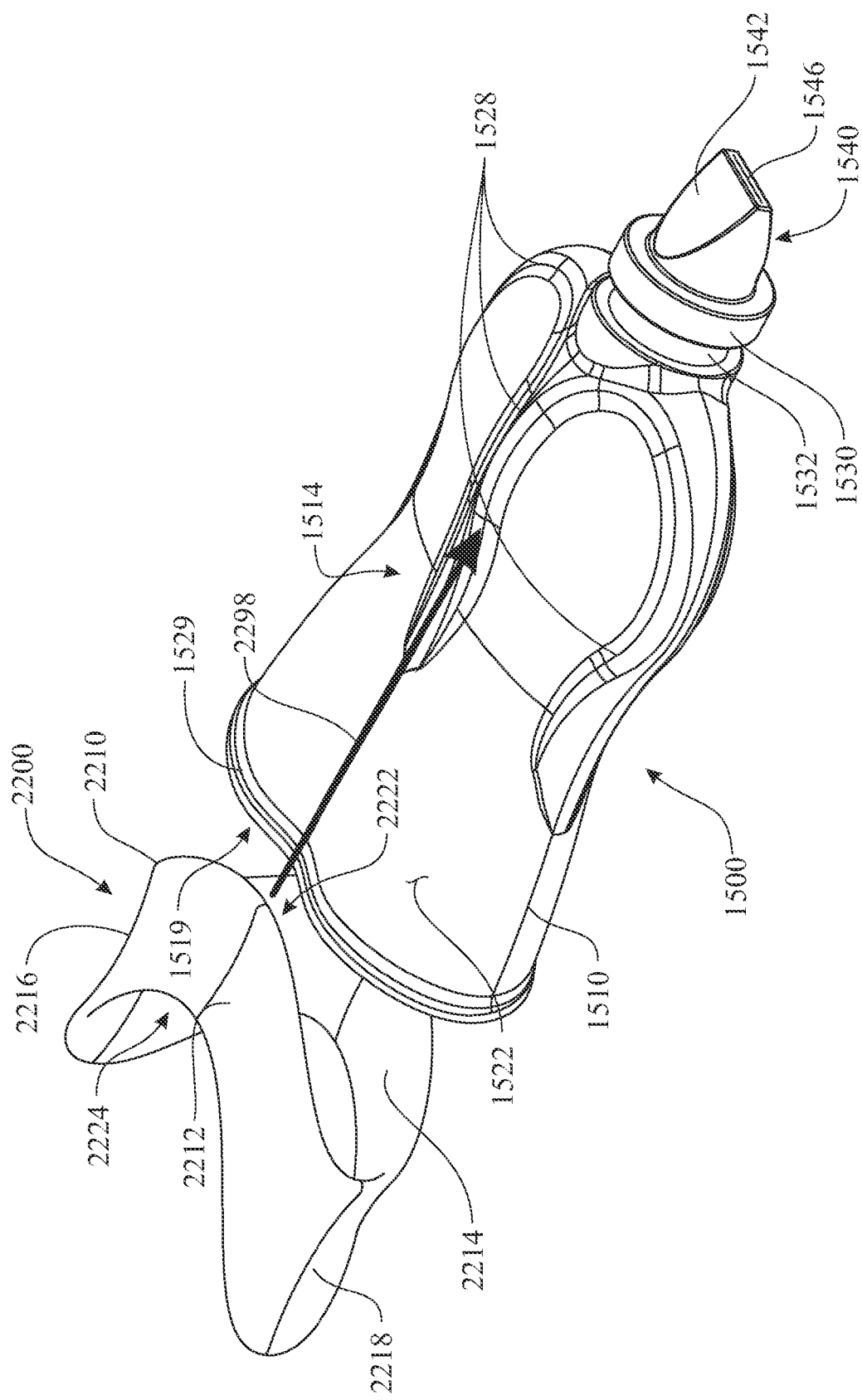
FIG. 61 presents an isometric top exploded assembly view introducing a orbital tongue shaping device for use in conjunction with the tongue attachment subassembly.
Figure 62:
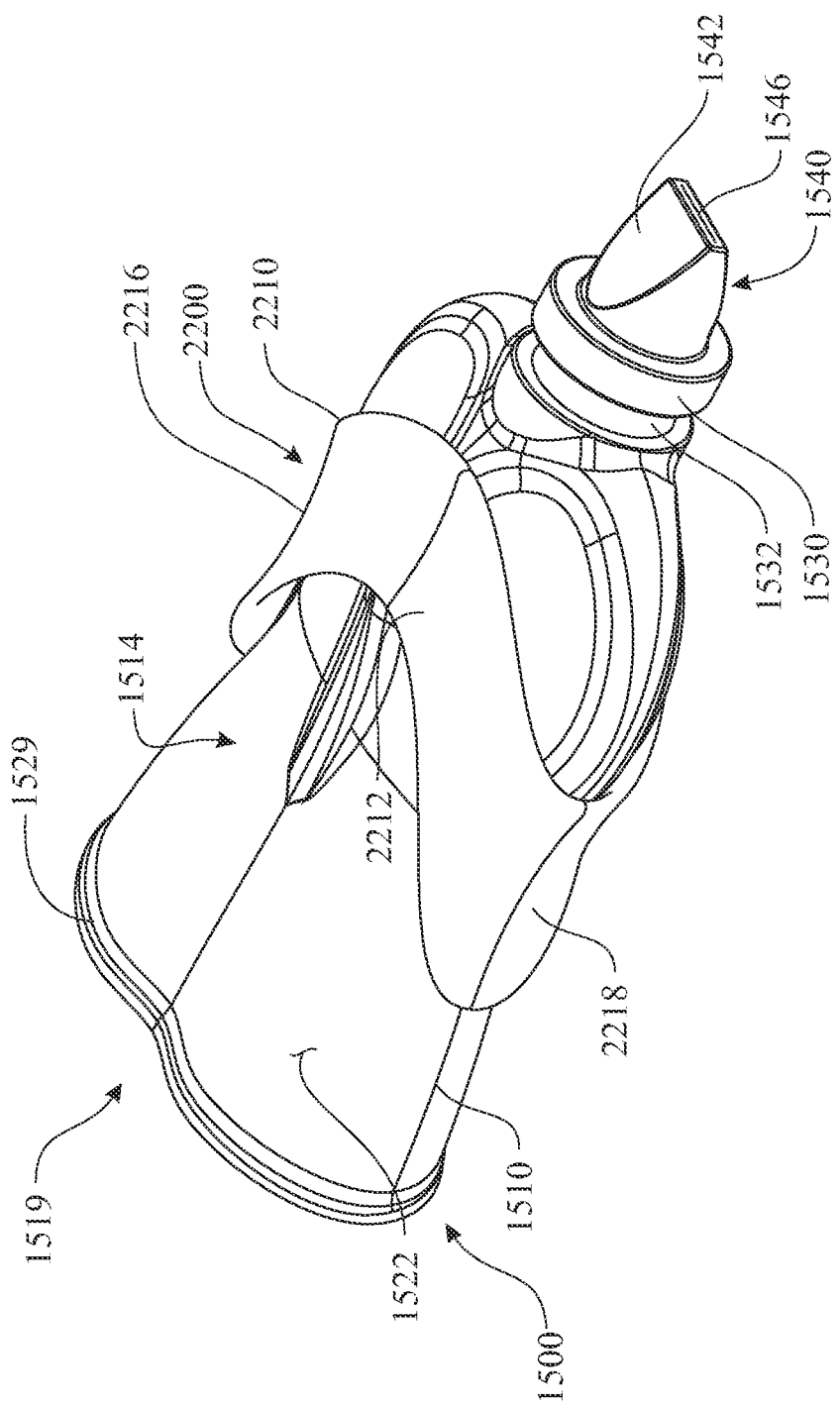
FIG. 62 presents an isometric top assembly view of the orbital tongue shaping device, introduced in FIG. 61, assembled onto the tongue attachment subassembly in preparation for use.
Figure 63:
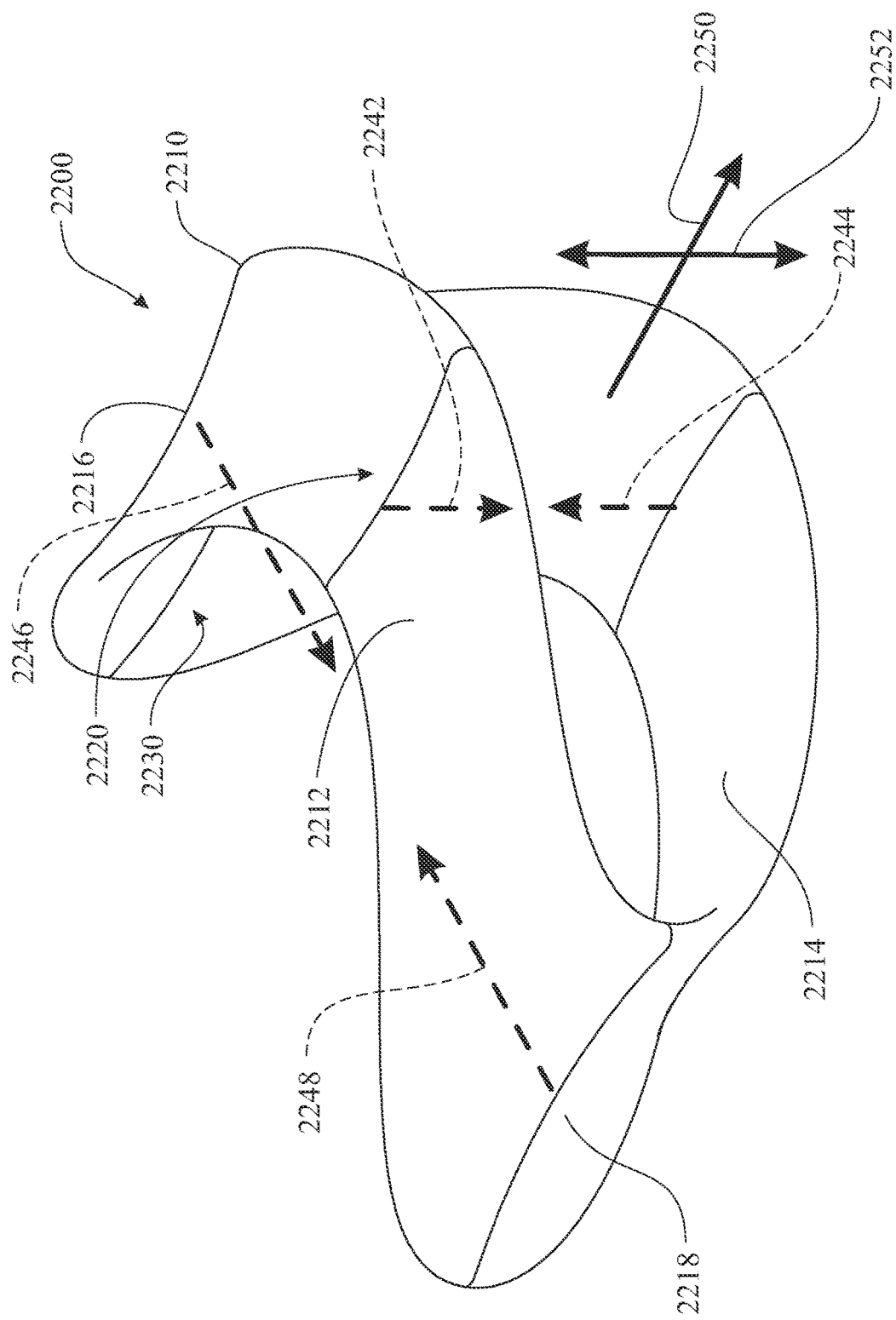
FIG. 63 presents an isometric top view of the orbital tongue shaping device, the illustration describing forces applied by the orbital tongue shaping device onto a patient's tongue and the resulting changes in a shape of the tongue.

The advantages of the tongue compression component 2000 can be adapted to another beneficial component: an orbital tongue shaping device 2200, as illustrated in FIGS. 61 through 63. The orbital tongue shaping device 2200 is designed to provide the same reshaping of the patient's tongue 310 as the tongue compression component 2000. The orbital tongue shaping device 2200 applies the reshaping forces reward of the position where the reshaping forces are applied by the tongue compression component 2000.

The orbital tongue shaping device 2200 is formed having an oval cross-sectioned shape, the section being taken along a transverse direction. The orbital tongue shaping device 2200 includes a orbital tongue shaping device body 2210, wherein the orbital tongue shaping device body 2210 can be described as having a plurality of segments, including: a orbital tongue shaping device body dorsal segment 2212 extending between and contiguous with upper portions of a orbital tongue shaping device body left side segment 2216 and a orbital tongue shaping device body right side segment 2218 and a orbital tongue shaping device body ventral segment 2214 (being similar to the orbital tongue shaping device body dorsal segment 2212) extending between and contiguous with lower portions of the orbital tongue shaping device body left side segment 2216 and the orbital tongue shaping device body right side segment 2218.

One or more of the segments 2212, 2214, 2216, 2218 can be shaped having an arch extending in along a longitudinal axis (extending between a leading edge 2222 and a trailing edge 2224). Each segment would include a concave surface on an orbital tongue shaping device body interior surface 2230 of the orbital tongue shaping device 2200. In a design where the thickness of each segment is consistent thereacross, the orbital tongue shaping device body exterior surface 2220 of each segment would have a concave shape extending between the leading edge 2222 and the reward edge or trailing edge 2224 of each respective segment 2212, 2214, 2216, 2218. The leading edge 2222 of at least one and preferably both of the orbital tongue shaping device body dorsal segment 2212 and the orbital tongue shaping device body ventral segment 2214 is shaped having a forward leaning arch, where the central portion of the leading edge 2222 is forward of each respective left and right edges thereof or extending away from a center of the orbital tongue shaping device 2200. The trailing or rearward edge 2224 of at least one and preferably both of the orbital tongue shaping device body dorsal segment 2212 and the orbital tongue shaping device body ventral segment 2214 is shaped having a forward leaning arch, where the central portion of the trailing or rearward edge 2224 is forward of each respective left and right edges thereof or extending towards the center of the orbital tongue shaping device 2200.

The orbital tongue shaping device 2200 is sized to generate or apply a dorsal tongue compression force 2242 inward from an interior surface of the orbital tongue shaping device body dorsal segment 2212, a ventral tongue compression force 2244 inward from an interior surface of the orbital tongue shaping device body ventral segment 2214, a left side tongue compression force 2246 inward from an interior surface of the orbital tongue shaping device body left side segment 2216, and a right side tongue compression force 2248 inward from an interior surface of the orbital tongue shaping device body right side segment 2218. The dorsal tongue compression force 2242 and the ventral tongue compression force 2244 are provided as equal and opposite forces. Similarly, the left side tongue compression force 2246 and the right side tongue compression force 2248 are provided as equal and opposite forces. The result of the applied forces 2242, 2244, 2246, 2248, as illustrated in FIG. 63, cause the patient's tongue to extend forward in accordance with a resulting tongue forward expansion 2250 and thicken (increase in a distance between the dorsal and ventral sides of the patient's tongue 310), in accordance with a resulting tongue thickening 2252.

The orbital tongue shaping device 2200 can be used in conjunction with the tongue attachment subassembly 1500 or used independently. When the orbital tongue shaping device 2200 is used in conjunction with the tongue attachment subassembly 1500, the orbital tongue shaping device 2200 would be slideably assembled onto the sheath 1510 of the tongue attachment subassembly 1500 in accordance with an orbital tongue shaping device assembly direction 2298, as illustrated in FIG. 61. The leading edge 2222 would be oriented towards the air extraction valve 1540 and the trailing edge 2224 would be oriented towards the sheath proximal end 1519. The tongue attachment subassembly 1500 can include or exclude the sheath shape retention feature 1528. The shape of the orbital tongue shaping device 2200 would take into considerations the inclusion or exclusion of the sheath shape retention feature 1528 on the tongue attachment subassembly 1500. Considerations for the presence of the sheath shape retention feature 1528 can include a shaping of the arches of the segments 2212, 2214, 2216, 2218, by including a recess within the respective orbital tongue shaping device body interior surface 2230 of the orbital tongue shaping device body dorsal segment 2212 and/or the orbital tongue shaping device body ventral segment 2214 to accommodate for the shape and size of the sheath shape retention feature 1528.

Since the orbital tongue shaping device 2200 is designed to provide restoration forces 2242, 2244, 2246, 2248 at a more central position on the patient's tongue, compared to the more forward position of the restoration forces applied by the tongue compression component 2000, it is understood that the tongue compression component 2000, the orbital tongue shaping device 2200, and the tongue attachment subassembly 1500 can be used together if so desired.

The exemplary embodiment of the orbital tongue shaping device 2200 illustrated herein is a separate element and slideably assembled onto the sheath 1510 of the tongue attachment subassembly 1500. The exemplary tongue attachment subassembly 1500 includes a sheath shape retention feature 1528. In an alternative arrangement, the features of the orbital tongue shaping device 2200 can be integrally formed with the sheath 1510 of the tongue attachment subassembly 1500. More specifically, the body of the sheath 1510 can be increased in thickness in a shape modeled after the orbital tongue shaping device 2200. In another alternative arrangement, a shape resembling the orbital tongue shaping device 2200 can be formed of a stiffer material on the sheath 1510 using a two shot molding process or any other suitable manufacturing process for molding a component of two different materials.

The sheath 1510 can be offered in a standard size, or available in a plurality of different sizes. A plurality of sized sheaths 1510 can be provided to an individual that would determine an optimal size for the sheath 1510 by placing several different sized sheaths 1510 onto the patient's tongue and determining fit, retention, and comfort. Once the optimal sheath 1510 or adjacent sized sheaths 1510 are identified, the optimal size can be determined. If two different sized sheaths 1510 are determined to provide the same result, a sheath 1510 can be designed using an average of the dimensions of the two identified sheaths 1510.

In an alternative process, a standard sheath 1510 can be used to determine an initial fit on the tongue 300 of the patient. If the sheath 1510 is determined to be too small or too large, a difference can be measured, estimated or any other suitable process for determining a difference between the sheath 1510 and the tongue 300 of the patient. The difference is then used to either design custom sheath 1510 or identify a suitable existing sized sheath 1510 for the specific patient. In a condition where it is determined to fabricate a custom sheath 1510, the designer would use the design of the existing sheath 1510 and scale the sheath 1510 up or down accordingly, while maintaining the dimensions of the valve and groove. This would include scaling the orbital tongue shaping device 2200 or any other component affected by the scaling process.

An exoskeleton (such as the sheath shape retention feature 1528) can be utilized with the tongue attachment subassembly 1500. The exoskeleton can be added to the sheath 1510 following fabrication or integrated into the design and fabricated in conjunction with the fabrication process of the sheath 1510. The exoskeleton can be joined to the sheath 1510 following fabrication of the sheath 1510 using any suitable joining techniques. The exoskeleton can be included in the molding process by including a thicker region defining the exoskeleton, using a two part molding process, where the exoskeleton would be fabricated of a more rigid material compared to the material of the sheath 1510, or using any other suitable fabrication process.

Figure 64:
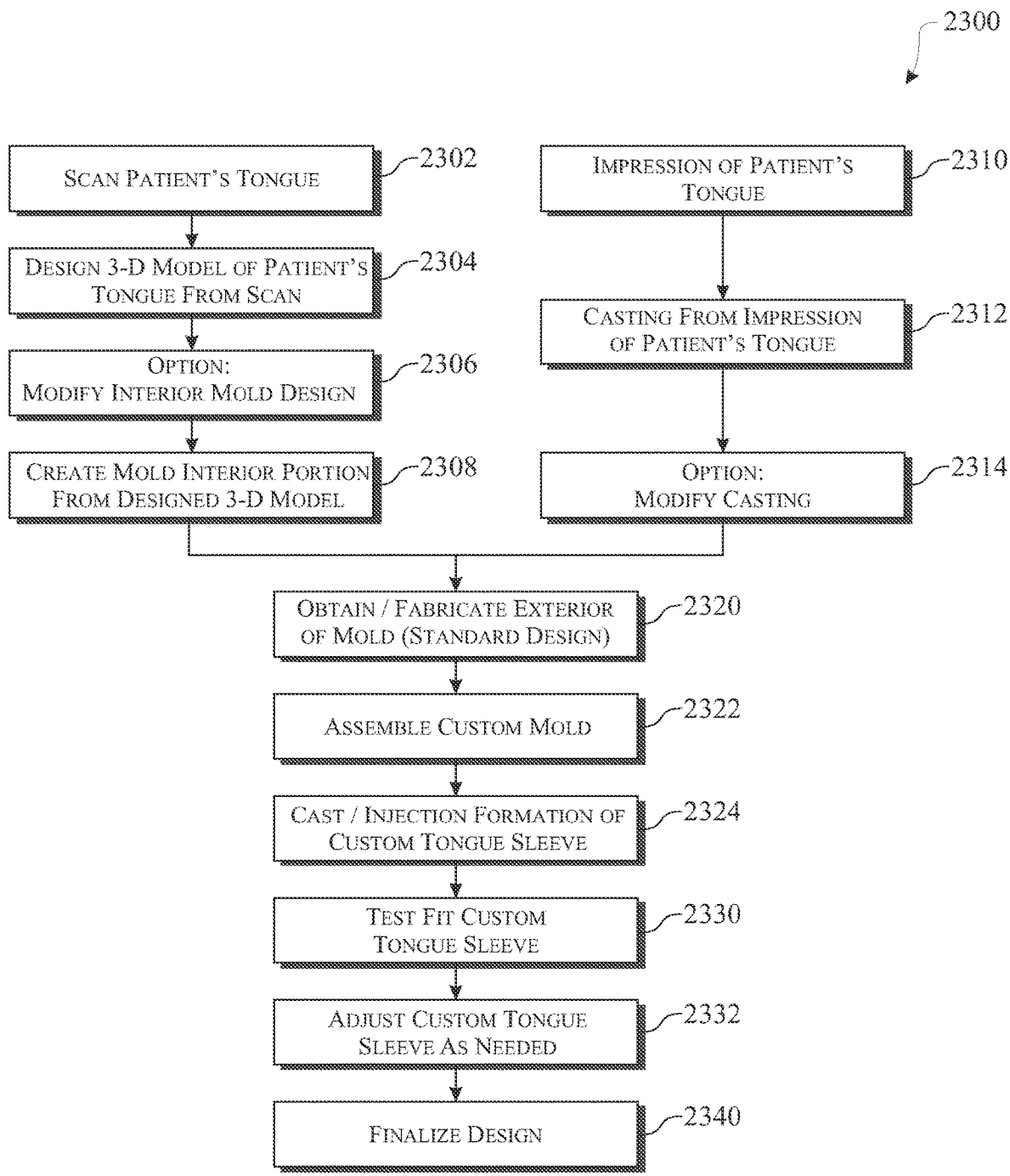
FIG. 64 presents an exemplary flow diagram presenting steps for fabrication of a custom tongue sleeve of the tongue sleeve assembly.

The tongue attachment sheath 1510 can be provided in a single size and shape and fabricated of a flexible material, thus enabling a one size fits most design. Alternatively, the tongue attachment sheath 1510 can be provided in a series of offered sizes and/or shapes and fabricated of a flexible material enabling cross over between sizes. The series of offered sizes and/or shapes enables an improved fit for most or all patients. In another option, the process for fabricating the tongue attachment sheath 1510 can be adapted to enable custom fit tongue attachment sheaths 1510. One exemplary custom tongue attachment sheath fabrication process 2300 is presented in FIG. 64. The steps described in the custom tongue attachment sheath fabrication process 2300 are representative of steps for fabrication of a custom tongue attachment sheath mold 2400, presented in FIGS. 65 and 66.

Figure 65:
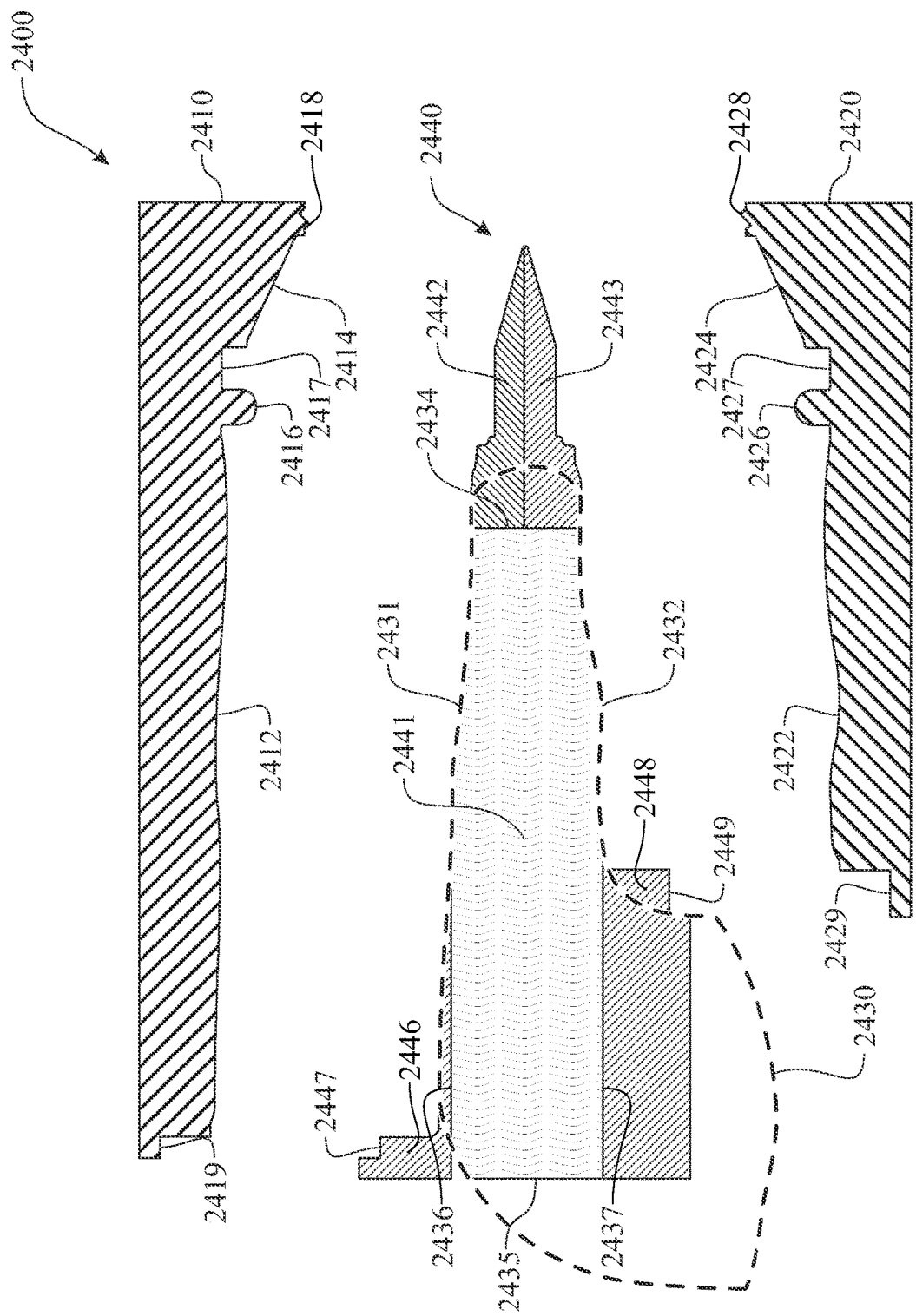
FIG. 65 presents an exploded sectioned elevation view of an exemplary mold for fabrication of the tongue sleeve.

The custom tongue attachment sheath fabrication process 2300 obtains an image of a patient's tongue 300. The image of the patient's tongue 300 can be acquired using any suitable method. The exemplary custom tongue attachment sheath fabrication process 2300 presents two (2) examples. A first example is to scan the patient's tongue 300 (step 2302). Once the patient's tongue 300 is scanned, the acquired data is converted into a three dimensional (3-D) model or an acquired tongue formation 2430 of the patient's tongue 300 (step 2304). The acquired tongue formation 2430 includes an acquired tongue formation upper surface 2431 and an acquired tongue formation lower surface 2432. The process may be enhanced from and/or require modifications to the three dimensional (3-D) model of the patient's tongue 300. The process can include an optional step of modifying the three dimensional (3-D) model of the patient's tongue 300 (step 2306). Examples of modifications that can be accomplished in step 2306 include: the three dimensional (3-D) model of the patient's tongue 300 can be modified by trimming a leading portion of the model of the tongue, forming a acquired tongue formation surface trimmed forward surface 2434; trimming a rearward portion of the model of the tongue, forming a acquired tongue formation trimmed rear surface 2435; trimming a top surface of the model of the tongue, forming a acquired tongue formation upper surface trimmed segment 2436; and trimming a bottom surface of the model of the tongue, forming a acquired tongue formation lower surface trimmed segment 2437. Additional features can be introduced into the model, such as introduction of a custom tongue attachment sheath mold upper valve interior member 2442, introduction of a custom tongue attachment sheath mold lower valve interior member 2443, introduction of a custom tongue attachment sheath mold upper rear interior member 2446, and introduction of a custom tongue attachment sheath mold lower rear interior member 2448. A custom tongue attachment sheath mold interior member upper rear registration formation 2447 can be included in the custom tongue attachment sheath mold upper rear interior member 2446 and a custom tongue attachment sheath mold interior member lower rear registration formation 2449 can be included in the custom tongue attachment sheath mold lower rear interior member 2448. The modified acquired tongue formation 2430 retains a large portion of the acquired tongue formation upper surface 2431 and a large portion of the acquired tongue formation lower surface 2432, as illustrated in FIG. 65. Details of the actual modifications are completed at the discretion of the designer.

Once the design of the three dimensional (3-D) model of the patient's tongue 300 is deemed to be acceptable, the computer generated modified three dimensional (3-D) model of the patient's tongue 300 is utilized to create a custom tongue attachment sheath mold interior member 2440 of the custom tongue attachment sheath mold 2400 (step 2308).

A second example initiates with a step of acquiring an impression of the patient's tongue 300 (step 2310). This can be accomplished using any known impression acquisition process. Commonly, alginate or polyvinylsiloxane is dispensed into a form and the form is positioned over the area of interest (in this case the patient's tongue 300). Other, softer materials, such as silicone can be used to obtain the impression. A casting would be made from the impression (step 2312), where the casting replicates the tongue. Typically, plaster or stone is poured into the hardened impression to create the casting. The casting can then be modified (step 2314) to tailor the shape of the casing to accommodate other features, such as the air extraction valve 1540, the interlock coupling flange 1530, the interlock coupling groove 1532, and any other associated feature. In the exemplary custom tongue attachment sheath mold central interior member 2441, the casting can be modified by trimming a leading portion of the casting representative of the tongue, forming a acquired tongue formation surface trimmed forward surface 2434; trimming a rearward portion of the casting representative of the tongue, forming a acquired tongue formation trimmed rear surface 2435; trimming a top surface of the casting representative of the tongue, forming a acquired tongue formation upper surface trimmed segment 2436; and trimming a bottom surface of the casting representative of the tongue, forming a acquired tongue formation lower surface trimmed segment 2437. In the exemplary custom tongue attachment sheath mold 2400, a custom tongue attachment sheath mold upper valve interior member 2442, a custom tongue attachment sheath mold lower valve interior member 2443, a custom tongue attachment sheath mold upper rear interior member 2446, and a custom tongue attachment sheath mold lower rear interior member 2448 are integrated into the shape of the casting. As above, the custom tongue attachment sheath mold interior member upper rear registration formation 2447 can be included in the custom tongue attachment sheath mold upper rear interior member 2446 and the custom tongue attachment sheath mold interior member lower rear registration formation 2449 can be included in the custom tongue attachment sheath mold lower rear interior member 2448.

There are scenarios where the patient's tongue 300 may or may not replicate the actual dimensions of the patient's tongue 300. In addition to the above examples of modifications to the casting, the custom tongue attachment sheath mold central interior member 2441 can be modified to accommodate any difference in actual dimension of the patient's tongue 300 based upon known or obtained discrepancies. This could include enlarging the casting, shrinking the casting, or any other shape modifications.

An exterior portion 2410, 2420 of the custom tongue attachment sheath mold 2400 are either fabricated or sourced from a fabricator (step 2320). In the exemplary illustration, the custom tongue attachment sheath mold upper outer member 2410 includes a custom tongue attachment sheath upper exterior mold surface 2412, a custom tongue attachment sheath upper exterior mold fill valve formation 2414, a custom tongue attachment sheath upper exterior mold groove formation 2416, and a custom tongue attachment sheath upper exterior mold flange formation 2417 to define features of the tongue attachment sleeve 1510. A custom tongue attachment sheath upper exterior mold front registration formation 2418 can be included in a formation of the custom tongue attachment sheath mold upper outer member 2410, where the custom tongue attachment sheath upper exterior mold front registration formation 2418 is located proximate the forward portion of the custom tongue attachment sheath mold 2400. A custom tongue attachment sheath upper exterior mold rear registration formation 2419 can be included in the formation of the custom tongue attachment sheath mold upper outer member 2410, where the custom tongue attachment sheath upper exterior mold rear registration formation 2419 is located proximate the rearward portion of the custom tongue attachment sheath mold 2400. Also in the exemplary illustration, the custom tongue attachment sheath mold lower outer member 2420 includes a custom tongue attachment sheath lower exterior mold surface 2422, a custom tongue attachment sheath lower exterior mold fill valve formation 2424, a custom tongue attachment sheath lower exterior mold groove formation 2426, and a custom tongue attachment sheath lower exterior mold flange formation 2427 to define features of the tongue attachment sleeve 1510. A custom tongue attachment sheath lower exterior mold front registration formation 2428 can be included in a formation of the custom tongue attachment sheath mold lower outer member 2420, where the custom tongue attachment sheath lower exterior mold front registration formation 2428 is located proximate the forward portion of the custom tongue attachment sheath mold 2400. A custom tongue attachment sheath lower exterior mold rear registration formation 2429 can be included in the formation of the custom tongue attachment sheath mold lower outer member 2420, where the custom tongue attachment sheath lower exterior mold rear registration formation 2429 is located proximate the rearward portion of the custom tongue attachment sheath mold 2400.

Figure 66:
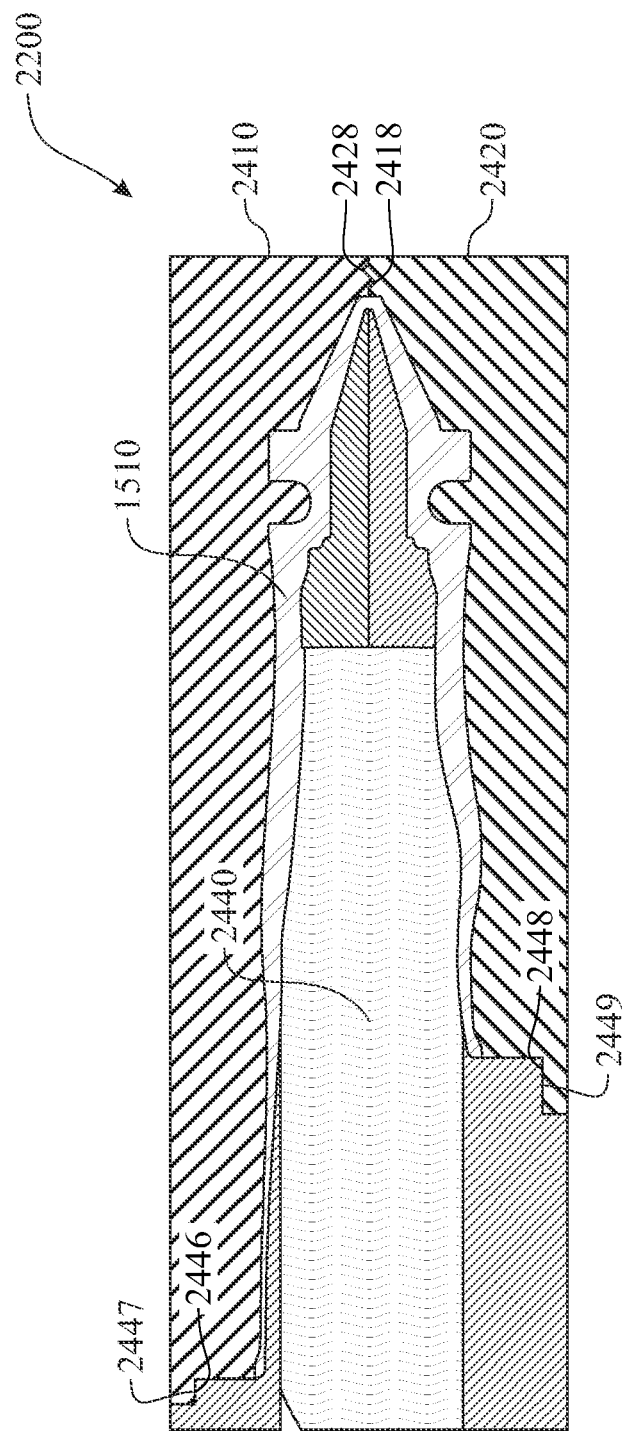
FIG. 66 presents an assembled sectioned elevation view of the exemplary mold for fabrication of the tongue sleeve, the illustration including a fabricated tongue sleeve.

The custom tongue attachment sheath mold upper outer member 2410, the custom tongue attachment sheath mold lower outer member 2420, and the custom tongue attachment sheath mold interior member 2440 are assembled together forming the custom tongue attachment sheath mold 2400 (step 2322). The assembly (step 2322) is accomplished by engaging the custom tongue attachment sheath upper exterior mold front registration formation 2418 and the custom tongue attachment sheath lower exterior mold front registration formation 2428 with one another; engaging the custom tongue attachment sheath upper exterior mold rear registration formation 2419 and the custom tongue attachment sheath mold interior member upper rear registration formation 2447 with one another; and engaging the custom tongue attachment sheath lower exterior mold rear registration formation 2429 and the custom tongue attachment sheath mold interior member lower rear registration formation 2449 with one another, as illustrated in FIG. 66. Opposed facing surfaces of the custom tongue attachment sheath mold upper outer member 2410 and the custom tongue attachment sheath mold interior member 2440 and opposed facing surfaces of the custom tongue attachment sheath mold lower outer member 2420 and the custom tongue attachment sheath mold interior member 2440 define a cavity for receiving molding material for creating the tongue attachment sleeve 1510.

Once the custom tongue attachment sheath mold 2400 is assembled, the tongue attachment sleeve 1510 is fabricated using any suitable, known molding or casting process (step 2324). The fabricated tongue attachment sleeve 1510 is processed, creating a tongue attachment sleeve 1510. The completed tongue attachment sleeve 1510 can then be test fit to the patient's tongue 300 (step 2330). The tongue attachment sleeve 1510 can be adjusted as needed to improve the fit and comfort when worn by the patient (step 2332). Once the patient feels that the tongue attachment sleeve 1510 is optimized, the tongue attachment sleeve 1510 is considered to be finalized (step 2340). Assembly of additional components to the tongue attachment sleeve 1510 to create the tongue attachment subassembly 1500 and/or additional processing of the tongue attachment sleeve 1510 can be accomplished in accordance with the assembly process.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Reference Element Descriptions

Ref. No. Description
- 100 tongue attachment subassembly
- 110 sheath
- 112 tongue receiving cavity
- 114 dorsal side
- 116 ventral side
- 117 tongue base clearance
- 118 sheath distal end
- 120 tongue engagement surface
- 122 exterior surface
- 130 sheath interlock member
- 132 interlock ridge
- 134 interlock tooth
- 136 interlock tooth receptacle
- 138 interlock base portion
- 140 air extraction valve
- 142 unidirectional valve flap
- 144 unidirectional valve seal
- 146 unidirectional valve orifice
- 150 air extraction device
- 152 air extraction bulb
- 154 air extraction pipette
- 200 maxilla attachment device
- 210 maxilla tray
- 220 maxilla tray's attachment side
- 222 maxilla tray's interlock side
- 230 tray interlock member
- 234 interlock tooth
- 236 interlock tooth receptacle
- 300 individual's tongue
- 302 tongue surface
- 304 gap
- 306 tongue base
- 310 extended tongue
- 320 maxilla (upper jaw)
- 322 mandible (lower jaw)
- 330 upper lip
- 400 sleep apnea control method flow diagram
- 402 obtain sleep apnea control device step
- 404 place tongue embracing member upon individual's tongue step
- 406 extract air from between the tongue receiving cavity of the tongue embracing member and the individual's tongue step
- 408 place maxilla attachment device onto the individual's maxilla step
- 410 extend individual's tongue forward step
- 412 engage sheath interlock member and tray interlock member together step 414 enjoy nights sleep step
416 remove vacuum from between the tongue receiving cavity and the individual's tongue step
418 remove the tongue embracing member from the individual's tongue step
420 remove maxilla attachment device from individual's maxilla step
500 tongue embracing member
510 sheath
512 tongue receiving cavity
514 dorsal side
516 ventral side
517 tongue base clearance
518 sheath distal end
530 sheath interlock member
540 air extraction valve
560 bladder exterior wall
562 bladder interior wall
564 bladder air chamber
600 tongue embracing member
610 sheath
612 tongue receiving cavity
614 dorsal side
616 ventral side
617 tongue base clearance
618 sheath distal end
620 interior wall
622 exterior wall
630 sheath interlock member
634 interlock pin
636 interlock tooth receptacle
638 interlock base portion
640 air extraction valve
650 air extraction device
652 air extraction bulb
700 tongue embracing member
710 sheath
712 tongue receiving cavity
714 dorsal side
716 ventral side
717 tongue base clearance
718 sheath distal end
720 interior surface
722 exterior surface
730 sheath interlock member
732 interlock member riser segment
734 interlock member engagement segment
736 interlock member positioning feature
740 air extraction valve
750 air extraction device
752 air extraction bulb
800 maxilla lip retention device
810 lip retention section
812 lip retention surface
820 maxilla lip retention positioning arm
822 positioning arm lateral arm
824 positioning arm riser arm
830 tray interlock member
834 interlocking member contact surface
836 interlock pin receptacle
838 interlock base portion
900 maxilla lip retention device
910 lip retention section
912 lip retention surface
930 maxilla lip retention positioning arm
932 positioning arm riser arm
934 positioning arm lateral arm
936 notched or ridged surface
950 position retaining member
952 position retaining member body
954 position retaining member body interior surface
956 position retaining member position locking element
982 interlocking member contact surface
1000 tongue embracing member
1010 sheath
1012 tongue receiving cavity
1014 dorsal side
1016 ventral side
1017 tongue base clearance
1018 sheath distal end
1020 interior surface
1022 exterior surface
1024 sheath interlock member overmolded retention feature
1030 sheath interlock member
1031 sheath interlock member base
1032 interlock member riser segment
1034 interlock member engagement segment
1036 interlock member positioning feature
1040 air extraction valve
1042 air extraction valve exterior surface
1044 air extraction valve interior surface
1046 air extraction valve seal flange
1047 air extraction valve seal flange orifice
1048 air extraction valve clearance
1050 air extraction device
1052 air extraction bulb
1054 bulb air extraction orifice
1060 bulb air extraction tube
1061 bulb air extraction tube hollow interior
1062 air extraction tube seal surface
1064 air extraction tube lead-in
1066 valve insertion stop seat
1069 valve return control magnet
1070 valve flap
1072 valve hinge pin
1074 valve operational handle
1079 valve return control magnet
1100 tongue embracing member
1110 sheath
1112 tongue receiving cavity
1114 dorsal side
1116 ventral side
1117 tongue base clearance
1118 sheath distal end
1120 interior surface
1121 sheath tongue sealing ridge
1122 exterior surface
1123 longitudinal channel groove
1124 longitudinal channel
1125 lateral channel groove
1126 lateral channel
1130 sheath interlock member
1131 sheath interlock member base
1132 interlock member riser segment
1133 sheath interlock member base longitudinal edge
1134 interlock member engagement segment
1135 sheath interlock member base lateral edge
1136 interlock member positioning feature
1139 interlock member distal end
1140 air extraction valve
1170 valve flap
1200 tongue embracing member
1210 sheath 1212 tongue receiving cavity
1214 dorsal side
1216 ventral side
1217 tongue base clearance
1218 sheath distal end
1220 interior surface
1221 sheath tongue sealing ridge
1222 exterior surface
1223 longitudinal channel groove
1224 longitudinal channel
1225 lateral channel groove
1226 lateral channel
1227 channel riser feature
1230 sheath interlock member
1231 sheath interlock member base
1232 interlock member riser segment
1233 sheath interlock member base longitudinal edge
1234 interlock member engagement segment
1235 sheath interlock member base lateral edge
1236 interlock member positioning feature
1239 interlock member distal end
1240 air extraction valve
1270 valve flap
1282 interlock member position retaining member support surface
1283 interlock member thickness wedge shaped segment
1284 interlock member locking surface projection (peak)
1286 interlock member locking surface recession (valley)
1289 position retaining member retention feature
1300 maxilla lip retention device
1310 lip retention section
1312 lip retention surface
1330 maxilla lip retention positioning arm
1332 positioning arm riser segment
1334 positioning arm lateral segment
1336 interlock member positioning feature
1350 position retaining member
1352 position retaining member body
1354 position retaining member body interior surface
1382 position retaining member support surface
1384 positioning arm locking surface projection (peak)
1386 positioning arm locking surface recession (valley)
1389 position retaining member retention feature
1430 sliding motion
1450 position retaining member sliding motion
1451 teeth disengaged configuration assembly thickness
1452 teeth engaged configuration assembly thickness
1453 teeth engaged configuration assembly wedge section thickness
1454 position retaining member internal span
1489 position retaining member retention thickness
1500 tongue attachment subassembly
1510 sheath
1512 tongue receiving cavity
1514 dorsal side
1516 ventral side
1517 tongue base clearance
1518 sheath distal end
1519 sheath proximal end
1520 tongue engagement surface
1522 exterior surface
1528 sheath shape retention feature
1529 sheath proximal edge reinforcement feature
1530 interlock coupling flange
1530a interlock coupling flange
1532 interlock coupling groove
1532a interlock coupling groove
1533 interlock coupling groove span
1534 rearward or inner flange surface
1536 forward or outer flange surface
1539 tongue insert orientation feature
1540 air extraction valve
1542 duckbill valve
1543 valve passageway
1546 duck valve slit
1570 tongue protection insert
1572 tongue protection insert tubular body
1574 tongue protection insert interior or proximal flange
1575 tongue protection insert interior flange arched surface
1576 tongue protection insert distal flange
1577 tongue protection insert tubular body vacuum passageway
1578 tongue protection insert interior flange vacuum orifice
1579 tongue protection insert orientation feature
1600 tongue position retention bracket
1610 tongue position retention bracket body
1612 tongue position retention bracket face contacting surface
1632 tongue position retention bracket assembly clip
1634 tongue position retention bracket assembly clip interior surface
1636 tongue position retention bracket assembly clip retention feature
1640 tongue position retention bracket valve guard
1700 tongue attachment subassembly
1710 sheath
1712 tongue receiving cavity
1714 dorsal side
1716 ventral side
1717 tongue base clearance
1718 sheath distal end
1719 sheath distal proximal end
1720 tongue engagement surface
1722 exterior surface
1728 sheath shape retention feature
1729 sheath proximal edge reinforcement feature
1730 interlock coupling flange
1732 interlock coupling groove
1739 tongue insert orientation feature
1743 valve passageway
1746 vacuum passageway
1754 tongue protection insert vacuum supply line
1770 tongue protection insert
1772 tongue protection insert tubular body
1773 tongue protection insert tubular vacuum tube retention barb
1774 tongue protection insert interior flange
1775 tongue protection insert interior flange arched surface
1776 tongue protection insert exterior sealing flange
1777 tongue protection insert tubular body vacuum passageway
1778 tongue protection insert interior flange vacuum orifice
1779 tongue protection insert orientation feature
1800 mask retention bracket
1810 mask retention bracket body
1812 mask contacting surface
1832 mask retention bracket assembly clip
1834 mask retention bracket assembly clip interior surface 1836 mask retention bracket assembly clip retention feature
1900 gas management mask
1910 gas management mask body
1913 gas management mask face seal
1920 gas delivery hose connection
1954 gas delivery hose
2000 tongue compression component
2032 tongue compression component assembly clip
2034 tongue compression component assembly clip interior surface
2036 tongue compression component assembly clip retention feature
2050 upper tongue compression arm
2052 exposed tongue compression arm surface
2053 tongue compression arm cantilever transition section
2060 lower tongue compression arm
2061 contacting tongue compression arm surface
2063 tongue compression arm cantilever transition section
2098 tongue compression component assembly direction
2100 teeth engaging tongue compression component
2132 tongue compression component assembly clip
2134 tongue compression component assembly clip interior surface
2136 tongue compression component assembly clip retention feature
2150 upper tongue compression arm
2152 exposed tongue compression arm surface
2153 tongue compression arm cantilever transition section
2154 outer locating projection
2155 outer locating projection tooth contacting surface
2156 central locating projection
2157 central locating projection tooth contacting surface
2158 inner locating projection
2159 inner locating projection tooth contacting surface
2160 lower tongue compression arm
2161 contacting tongue compression arm surface
2163 tongue compression arm cantilever transition section
2164 outer locating projection
2165 outer locating projection tooth contacting surface
2166 central locating projection
2167 central locating projection tooth contacting surface
2168 inner locating projection
2169 inner locating projection tooth contacting surface
2180 first spacer
2181 thickness of first spacer
2182 second spacer
2183 thickness of second spacer
2200 orbital tongue shaping device
2210 orbital tongue shaping device body
2212 orbital tongue shaping device body dorsal segment
2214 orbital tongue shaping device body ventral segment
2216 orbital tongue shaping device body left side segment
2218 orbital tongue shaping device body right side segment
2220 orbital tongue shaping device body exterior surface
2222 orbital tongue shaping device body leading edge
2224 orbital tongue shaping device body trailing edge
2230 orbital tongue shaping device body interior surface
2242 dorsal tongue compression force
2244 ventral tongue compression force
2246 left side tongue compression force
2248 right side tongue compression force
2250 resulting tongue forward expansion
2252 resulting tongue thickening
2298 orbital tongue shaping device assembly direction
2300 custom tongue attachment sheath fabrication process
2302 scan patient's tongue step
2304 design 3-D model of patient's tongue from scan step
2306 optional step of modifying interior mold design
2308 create interior mold portion from designed 3-D model step
2310 acquire impression of patient's tongue step
2312 take a casting from impression step
2314 optional step of modifying casting
2320 obtain/fabricate exterior portion of the mold step
2322 assemble custom mold step
2324 cast/injection mold fabrication of custom tongue attachment sheath step
2330 test fit custom tongue attachment sheath step
2332 adjust custom tongue attachment sheath as needed step
2340 finalize design step
2400 custom tongue attachment sheath mold
2410 custom tongue attachment sheath mold upper outer member
2412 custom tongue attachment sheath upper exterior mold surface
2414 custom tongue attachment sheath upper exterior mold fill valve formation
2416 custom tongue attachment sheath upper exterior mold groove formation
2417 custom tongue attachment sheath upper exterior mold flange formation
2418 custom tongue attachment sheath upper exterior mold front registration formation
2419 custom tongue attachment sheath upper exterior mold rear registration formation
2420 custom tongue attachment sheath mold lower outer member
2422 custom tongue attachment sheath lower exterior mold surface
2424 custom tongue attachment sheath lower exterior mold fill valve formation
2426 custom tongue attachment sheath lower exterior mold groove formation
2427 custom tongue attachment sheath lower exterior mold flange formation
2428 custom tongue attachment sheath lower exterior mold front registration formation
2429 custom tongue attachment sheath lower exterior mold rear registration formation
2430 acquired tongue formation
2431 acquired tongue formation upper surface
2432 acquired tongue formation lower surface
2434 acquired tongue formation surface trimmed forward surface
2435 acquired tongue formation trimmed rear surface
2436 acquired tongue formation upper surface trimmed segment
2437 acquired tongue formation lower surface trimmed segment
2440 custom tongue attachment sheath mold interior member
2441 custom tongue attachment sheath mold central interior member
2442 custom tongue attachment sheath mold upper valve interior member 2443 custom tongue attachment sheath mold lower valve interior member
2446 custom tongue attachment sheath mold upper rear interior member
2447 custom tongue attachment sheath mold interior member upper rear registration formation
2448 custom tongue attachment sheath mold lower rear interior member
2449 custom tongue attachment sheath mold interior member lower rear registration formation

What is claimed is:

1. A method of using a tongue attachment assembly for retention of an accessory, the method comprising steps of:
   placing a tongue attachment sheath of the tongue attachment assembly onto a tongue of an intended subject, the tongue attachment assembly comprising an air extraction tubular passageway extending forward from a distal end of the tongue attachment sheath and an interlock coupling formation formed about a portion of the air extraction tubular passageway;
   securing the tongue attachment sheath to the tongue of the intended subject by drawing a vacuum between the tongue attachment sheath and the tongue of the intended subject;
   securing the accessory to the tongue attachment assembly by assembling a tongue position retention bracket assembly formation of the accessory to the interlock coupling formation using a movement in a radial direction,
   wherein the tongue position retention bracket assembly formation is circumferential in shape following a contour of a circumference of over 180 degrees of the interlock coupling formation creating a self retaining interface therebetween.

2. The method as recited in claim 1, wherein the interlock coupling formation is an interlock coupling groove and the tongue position retention bracket assembly formation is a tongue position retention bracket assembly clip, the method further comprising a step of:
   securing the accessory to the tongue attachment assembly by assembling the tongue position retention bracket assembly clip of the accessory to the interlock coupling groove using a movement in the radial direction.

3. The method as recited in claim 1, the method further comprising steps of:
   obtaining a formation of the tongue of the intended subject; and
   using the obtained formation of the tongue of the intended subject to fabricate the tongue attachment sheath.

4. The method as recited in claim 1, the method further comprising a step of:
   providing a reinforcement element to the tongue attachment sheath, wherein the reinforcement element is one of:
   (a) assembled to the tongue attachment sheath, or
   (b) integral with the tongue attachment sheath.

5. The method as recited in claim 1, the method further comprising steps of:
   determining which sized tongue attachment sheath is optimal by placing different tongue attachment sheaths from a group of multiple sized tongue attachment sheaths,
   placing the tongue attachment sheath that is determined to have the optimal size upon the tongue of the intended subject.

6. The method as recited in claim 1, the method further comprising steps of:
   obtaining a formation of the tongue; and
   utilizing the obtained formation of the tongue to define a shape of an interior surface of the tongue attachment sheath.

7. The method as recited in claim 6, the method further comprising steps of:
   wherein the formation of the tongue is obtained by at least one of:
   (a) taking an impression of the tongue of the intended subject, and
   (b) taking a scan of the tongue of the intended subject.

8. The method as recited in claim 1, the method further comprising at least one of the following steps:
   (a) taking an impression of the intended subject, and
   (b) taking a scan of the intended subject.

9. The method as recited in claim 1, the method further comprising at least one of the following:
   (a) employing the accessory to manipulate the tongue,
   (b) employing the accessory for treatment for snoring, and
   (c) employing the accessory for treatment for sleep apnea.

10. The method as recited in claim 1, the method further comprising at least one of the following:
    (a) employing the accessory to provide aid to a medical professional during a medical procedure,
    (b) employing the accessory for securing of a mask, and
    (c) securing of a gas delivery system.

11. A method of using a tongue attachment assembly for retention of an accessory, the method comprising steps of:
    placing a tongue attachment sheath of the tongue attachment assembly onto a tongue of an intended subject, the tongue attachment assembly comprising an air extraction valve extending forward from a distal end of the tongue attachment sheath and an interlock coupling formation formed about a portion of the air extraction valve;
    securing the tongue attachment sheath to the tongue of the intended subject by drawing a vacuum between the tongue attachment sheath and the tongue of the intended subject;
    securing the accessory to the tongue attachment assembly by assembling a tongue position retention bracket assembly formation of the accessory to the interlock coupling formation using a movement in a radial direction,
    wherein the tongue position retention bracket assembly formation is circumferential in shape following a contour of a circumference of over 180 degrees of the interlock coupling formation creating a self retaining interface therebetween.

12. The method as recited in claim 11, wherein the interlock coupling formation is an interlock coupling groove and the tongue position retention bracket assembly formation is a tongue position retention bracket assembly clip, the method further comprising a step of:
    securing the accessory to the tongue attachment assembly by assembling the tongue position retention bracket assembly clip of the accessory to the interlock coupling groove using a movement in the radial direction.

13. The method as recited in claim 11, the method further comprising steps of:
    obtaining a formation of the tongue of the intended subject; and
    using the obtained formation of the tongue of the intended subject to fabricate the tongue attachment sheath.

14. The method as recited in claim 11, the method further comprising a step of:
   providing a reinforcement element to the tongue attachment sheath, wherein the reinforcement element is one of:
   (a) assembled to the tongue attachment sheath, or
   (b) integral with the tongue attachment sheath.

15. The method as recited in claim 11, the method further comprising steps of:
   determining which sized tongue attachment sheath is optimal by placing different tongue attachment sheaths from a group of multiple sized tongue attachment sheaths,
   placing the tongue attachment sheath that is determined to have the optimal size upon the tongue of the intended subject.

16. The method as recited in claim 11, the method further comprising steps of:
   obtaining a formation of the tongue; and
   utilizing the obtained formation of the tongue to define a shape of an interior surface of the tongue attachment sheath.

17. The method as recited in claim 16, the method further comprising steps of:
   wherein the formation of the tongue is obtained by at least one of:
   (a) taking an impression of the tongue of the intended subject, and
   (b) taking a scan of the tongue of the intended subject.

18. The method as recited in claim 11, the method further comprising at least one of the following steps:
   (a) taking an impression of the intended subject, and
   (b) taking a scan of the intended subject.

19. The method as recited in claim 11, the method further comprising at least one of the following:
   (a) employing the accessory to manipulate the tongue,
   (b) employing the accessory for treatment for snoring, and
   (c) employing the accessory for treatment for sleep apnea.

20. The method as recited in claim 11, the method further comprising at least one of the following:
   (a) employing the accessory to provide aid to a medical professional during a medical procedure,
   (b) employing the accessory for securing of a mask, and
   (c) securing of a gas delivery system.

21. A method of using a tongue attachment assembly for retention of an accessory, the method comprising steps of:
   placing a tongue attachment sheath of the tongue attachment assembly onto a tongue of an intended subject, the tongue attachment assembly comprising an air extraction tubular passageway extending forward from a distal end of the tongue attachment sheath and an interlock coupling formation formed about a portion of the air extraction tubular passageway;
   determining which sized tongue attachment sheath is optimal by placing different tongue attachment sheaths from a group of multiple sized tongue attachment sheaths;
   placing the tongue attachment sheath that is determined to have the optimal size upon the tongue of the intended subject;
   securing the tongue attachment sheath to the tongue of the intended subject by drawing a vacuum between the tongue attachment sheath and the tongue of the intended subject; and
   securing the accessory to the tongue attachment assembly by assembling a tongue position retention bracket assembly formation of the accessory to the interlock coupling formation using a movement in a radial direction.

\* \* \* \* \*